US012433156B2

United States Patent
Galán García et al.

(10) Patent No.: US 12,433,156 B2
(45) Date of Patent: Sep. 30, 2025

(54) TRIAZINE COMPOUNDS SUBSTITUTED WITH BULKY GROUPS

(71) Applicant: NOVALED GMBH, Dresden (DE)

(72) Inventors: Elena Galán García, Dresden (DE); Benjamin Schulze, Dresden (DE); Julien Frey, Dresden (DE)

(73) Assignee: Novaled GmbH, Dresden (DE)

( * ) Notice: Subject to any disclaimer, the term of this patent is extended or adjusted under 35 U.S.C. 154(b) by 291 days.

(21) Appl. No.: 17/622,724

(22) PCT Filed: Jun. 24, 2020

(86) PCT No.: PCT/EP2020/067731
§ 371 (c)(1),
(2) Date: Dec. 24, 2021

(87) PCT Pub. No.: WO2020/260406
PCT Pub. Date: Dec. 30, 2020

(65) Prior Publication Data
US 2022/0263029 A1  Aug. 18, 2022

(30) Foreign Application Priority Data

Jun. 25, 2019 (EP) .................................... 19182224

(51) Int. Cl.
*C09K 11/06* (2006.01)
*C07D 405/04* (2006.01)
(Continued)

(52) U.S. Cl.
CPC ......... *H10K 85/654* (2023.02); *C07D 405/04* (2013.01); *C09K 11/06* (2013.01);
(Continued)

(58) Field of Classification Search
CPC ............... H10K 85/654; H10K 85/615; H10K 85/6574; H10K 50/16; H10K 50/165;
(Continued)

(56) References Cited

U.S. PATENT DOCUMENTS

2019/0214570 A1  7/2019 Inayama et al.
2020/0227644 A1*  7/2020 Lee ....................... C07D 251/24

FOREIGN PATENT DOCUMENTS

KR  20170111387 A  10/2017
KR  20180093354 A  8/2018
(Continued)

OTHER PUBLICATIONS

PCT "International Search Report and Written Opinion" App. No. PCT/EP2020/067731, Aug. 17, 2020 mailed , 11 pages.
(Continued)

*Primary Examiner* — Robert S Jones, Jr.
*Assistant Examiner* — Jaison P Thomas
(74) *Attorney, Agent, or Firm* — Eversheds Sutherland (US) LLP

(57) ABSTRACT

The present invention relates to a triazine compound according to formula (I), wherein L=phenylene or naphthylene and, wherein $G^1$ has the formula (2), wherein $G^1$ of formula (2) is linked to formula (1) to one position, selected from the positions marked by formulae (A), (B), and (C) and the compound is suitable for use as a layer material for electronic devices, and to an organic semiconductor layer comprising at least one compound according to formula (1), as well as to an organic electronic device comprising at least one organic semiconductor layer, and a method of manufacturing the same.

(Continued)

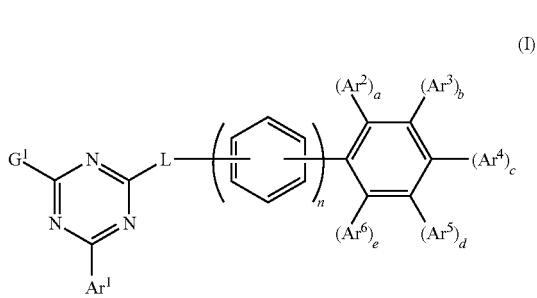

(I)

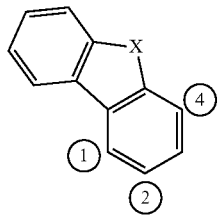

(2)

① (A)
② (B)
④ (C)

19 Claims, 2 Drawing Sheets

(51) Int. Cl.
  *H10K 85/60* (2023.01)
  *H10K 50/16* (2023.01)
(52) U.S. Cl.
  CPC ....... *H10K 85/615* (2023.02); *H10K 85/6574* (2023.02); *C09K 2211/1018* (2013.01); *H10K 50/16* (2023.02)
(58) Field of Classification Search
  CPC .... H10K 50/171; H10K 85/30; C07D 405/04; C07D 405/14; C09K 11/06; C09K 2211/1018
  See application file for complete search history.

(56) References Cited

FOREIGN PATENT DOCUMENTS

| | | | |
|---|---|---|---|
| KR | 20190086347 A | 7/2019 | |
| KR | 20200067500 A | 6/2020 | |
| WO | 2018215355 A1 | 11/2018 | |
| WO | WO-2019022458 A1 * | 1/2019 | ........... C07D 213/16 |
| WO | 2020032424 A1 | 2/2020 | |
| WO | WO-2020032428 A1 * | 2/2020 | ......... H01L 51/0071 |
| WO | 2020130726 A1 | 6/2020 | |
| WO | WO-2021029598 A1 * | 2/2021 | |

OTHER PUBLICATIONS

Communication pursuant to Article 94(3) EPC issued in European application No. 20734204.9, dated Mar. 20, 2023, 6 pages.
Communication pursuant to Article 94(3) EPC issued in European application No. 19182224.6, dated Dec. 9, 2021.

* cited by examiner

TRIAZINE COMPOUNDS SUBSTITUTED WITH BULKY GROUPS

CROSS REFERENCE TO RELATED APPLICATIONS

This application is a U.S. national stage application of PCT/EP2020/067731, filed Jun. 24, 2020, which claims priority to European Application No. 19182224.6, filed Jun. 25, 2019. The content of these applications is incorporated herein by reference.

TECHNICAL FIELD

The present invention relates to triazine compounds, in particular to triazine compounds substituted with bulky groups, suitable for use as a layer material for electronic devices, and relates to an organic semiconductor layer comprising at least one compound thereof, as well as to an organic electronic device comprising at least one organic semiconductor layer, and a method of manufacturing the same.

BACKGROUND ART

Organic electronic devices, such as organic light-emitting diodes OLEDs, which are self-emitting devices, have a wide viewing angle, excellent contrast, quick response, high brightness, excellent operating voltage characteristics, and color reproduction. A typical OLED comprises an anode, a hole transport layer HTL, an emission layer EML, an electron transport layer ETL, and a cathode, which are sequentially stacked on a substrate. In this regard, the HTL, the EML, and the ETL are thin films formed from organic compounds.

When a voltage is applied to the anode and the cathode, holes injected from the anode move to the EML, via the HTL, and electrons injected from the cathode move to the EML, via the ETL. The holes and electrons recombine in the EML to generate excitons. When the excitons drop from an excited state to a ground state, light is emitted. The injection and flow of holes and electrons should be balanced, so that an OLED having the above-described structure has excellent efficiency and/or a long lifetime.

Performance of an organic light emitting diode may be affected by characteristics of the organic semiconductor layer, and among them, may be affected by characteristics of an organic material of the organic semiconductor layer.

Particularly, development of an organic material being capable of increasing electron mobility and simultaneously increasing electrochemical stability is needed so that the organic electronic device, such as an organic light emitting diode, may be applied to a large-size flat panel display.

Further, development of an organic material being capable to have an extended life span at higher current density and thereby at higher brightness is needed.

There remains a need to improve performance of organic semiconductor layers, organic semiconductor materials, as well as organic electronic devices thereof, in particular to achieve increased lifetime at higher current density and have a higher efficiency through improving the characteristics of the triazine compounds comprised therein.

There is a need for alternative organic semiconductor materials and organic semiconductor layers as well as organic electronic devices having increased lifetime at higher current density, and/or improved efficiency at low operating voltage.

In particular there is a need for alternative compounds having increased lifetime at higher current density as well as improved efficiency, and at the same time keeping the operating voltage and thereby the power consumption low to deliver long battery life for example mobile electronic devices.

DISCLOSURE

An aspect of the present invention provides a triazine compound according to formula I:

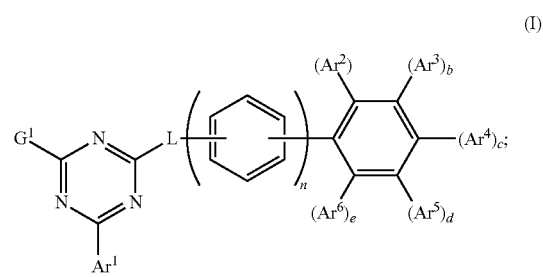

(I)

wherein formula I for L=phenylene and formula I is represented by formula 1:

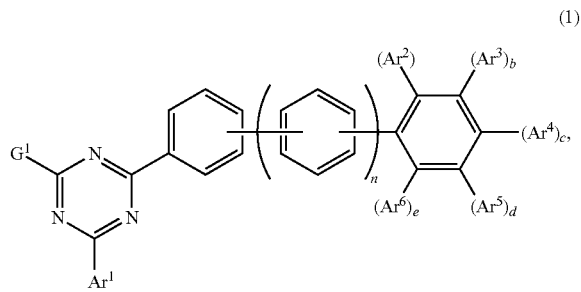

(1)

and wherein formula I for L=naphthylene and formula I is represented by formula 1a:

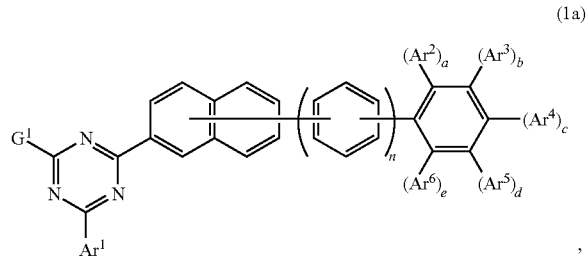

(1a)

, wherein
G$^1$ has the formula 2:

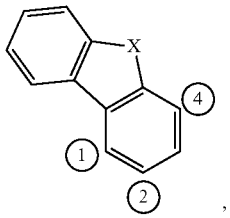

wherein
G$^1$ of formula 2 is linked to formula 1 to one position, selected from the positions marked by "①, ②, and ④";
X is O, S or Se;
a, b, c, d, e are selected from 0 or 1, wherein 2≤a+b+c+d+e≤5;
n is selected from 0, 1 or 2,
Ar$^1$ is selected from H, C$_1$ to C$_{16}$ alkyl, substituted or unsubstituted C$_6$ to C$_{40}$ aryl, substituted or unsubstituted C$_3$ to C$_{40}$ heteroaryl, wherein
the substituents of the substituted C$_6$ to C$_{40}$ aryl and substituted C$_3$ to C$_{40}$ heteroaryl are selected from C$_1$ to C$_{16}$ alkyl, C$_1$ to C$_{16}$ alkoxy, C$_3$ to C$_{16}$ branched alkyl, C$_3$ to C$_{16}$ cyclic alkyl, C$_3$ to C$_{16}$ branched alkoxy, C$_3$ to C$_{16}$ cyclic alkoxy, partially or perfluorinated C$_1$ to C$_{16}$ alkyl, partially or perfluorinated C$_1$ to C$_{16}$ alkoxy, partially or perdeuterated C$_1$ to C$_{16}$ alkyl, partially or perdeuterated C$_1$ to C$_{16}$ alkoxy, C$_6$ to C$_{24}$ aryl, C$_3$ to C$_{25}$ heteroaryl, —PX(R$^1$)$_2$, D, F or CN, wherein
R$^1$ is independently selected from C$_1$ to C$_{16}$ alkyl, C$_1$ to C$_{16}$ alkoxy, partially or perfluorinated C$_1$ to C$_{16}$ alkyl, partially or perfluorinated C$_1$ to C$_{16}$ alkoxy, partially or perdeuterated C$_1$ to C$_{16}$ alkyl, partially or perdeuterated C$_1$ to C$_{16}$ alkoxy, C$_6$ to C$_{18}$ aryl, C$_3$ to C$_{25}$ heteroaryl;
Ar$^2$, Ar$^3$, Ar$^4$, Ar$^5$ and Ar$^6$ are independently selected from substituted or unsubstituted C$_6$ to C$_{12}$ aryl or substituted or unsubstituted C$_4$ to C$_{10}$ heteroaryl, wherein
the substituent of the substituted C$_6$ to C$_{12}$ aryl or substituted C$_4$ to C$_{10}$ heteroaryl is selected from C$_1$ to C$_6$ alkyl, C$_1$ to C$_6$ alkoxy, partially or perdeuterated C$_1$ to C$_6$ alkyl, partially or perdeuterated C$_1$ to C$_6$ alkoxy, partially or perfluorinated C$_1$ to C$_6$ alkyl, partially or perfluorinated C$_1$ to C$_6$ alkoxy, D, F, or CN According to one embodiment a triazine compound according to formula 1 is provided:

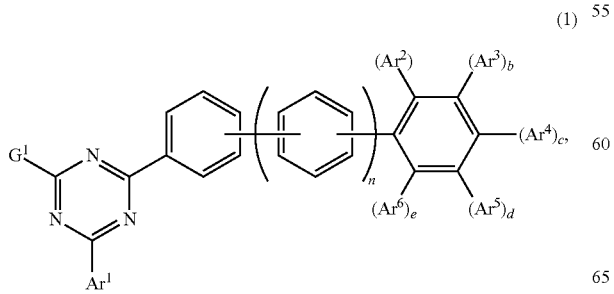

wherein
G$^1$ has the formula 2:

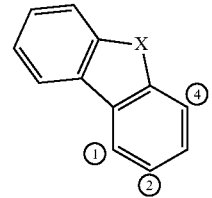

wherein
G$^1$ of formula 2 is linked to formula 1 to one position, selected from the positions marked by "①, ②, and ④";
X is O, S or Se;
a, b, c, d, e are selected from 0 or 1, wherein 2≤a+b+c+d+e≤5;
n is selected from 0, 1 or 2,
Ar$^1$ is selected from H, C$_1$ to C$_{16}$ alkyl, substituted or unsubstituted C$_6$ to C$_{40}$ aryl, substituted or unsubstituted C$_3$ to C$_{40}$ heteroaryl, wherein
the substituents of the substituted C$_6$ to C$_{40}$ aryl and substituted C$_3$ to C$_{40}$ heteroaryl are selected from C$_1$ to C$_{16}$ alkyl, C$_1$ to C$_{16}$ alkoxy, C$_3$ to C$_{16}$ branched alkyl, C$_3$ to C$_{16}$ cyclic alkyl, C$_3$ to C$_{16}$ branched alkoxy, C$_3$ to C$_{16}$ cyclic alkoxy, partially or perfluorinated C$_1$ to C$_{16}$ alkyl, partially or perfluorinated C$_1$ to C$_{16}$ alkoxy, partially or perdeuterated C$_1$ to C$_{16}$ alkyl, partially or perdeuterated C$_1$ to C$_{16}$ alkoxy, C$_6$ to C$_{24}$ aryl, C$_3$ to C$_{25}$ heteroaryl, —PX(R$^1$)$_2$, D, F or CN, wherein
R$^1$ is independently selected from C$_1$ to C$_{16}$ alkyl, C$_1$ to C$_{16}$ alkoxy, partially or perfluorinated C$_1$ to C$_{16}$ alkyl, partially or perfluorinated C$_1$ to C$_{16}$ alkoxy, partially or perdeuterated C$_1$ to C$_{16}$ alkyl, partially or perdeuterated C$_1$ to C$_{16}$ alkoxy, C$_6$ to C$_{18}$ aryl, C$_3$ to C$_{25}$ heteroaryl;
Ar$^2$, Ar$^3$, Ar$^4$, Ar$^5$ and Ar$^6$ are independently selected from substituted or unsubstituted C$_6$ to C$_{12}$ aryl or substituted or unsubstituted C$_4$ to C$_{10}$ heteroaryl, wherein
the substituent of the substituted C$_6$ to C$_{12}$ aryl or substituted C$_4$ to C$_{10}$ heteroaryl is selected from C$_1$ to C$_6$ alkyl, C$_1$ to C$_6$ alkoxy, partially or perdeuterated C$_1$ to C$_6$ alkyl, partially or perdeuterated C$_1$ to C$_6$ alkoxy, partially or perfluorinated C$_1$ to C$_6$ alkyl, partially or perfluorinated C$_1$ to C$_6$ alkoxy, D, F, or CN.

Hetero atoms if not otherwise stated can be individually selected from N, O, S, B, Si, P, Se, preferably from N, O and S and more preferred is N.

If not otherwise stated H can represent hydrogen or deuterium.

According to one embodiment of the triazine compound of formula 1 or 1a:

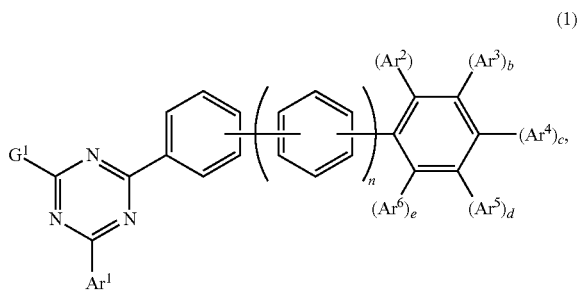

(1)

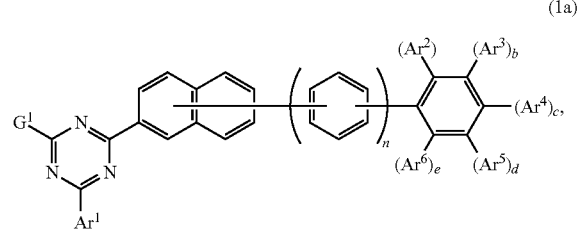

(1a)

wherein
G¹ has the formula 2:

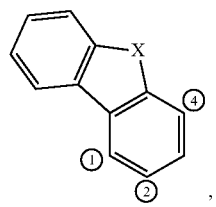

(2)

wherein
G¹ of formula 2 is linked to formula 1 to one position, selected from the positions marked by "①, ②, and ④";
X may be O, S or Se;
a, b, c, d, e may be selected from 0 or 1, wherein $2 \leq a+b+c+d+e \leq 5$;
n may be selected from 0, 1 or 2;
$Ar^1$ may be selected from substituted or unsubstituted $C_6$ to $C_{36}$ aryl, substituted or unsubstituted $C_3$ to $C_{35}$ heteroaryl, wherein
  the substituents of the substituted $C_6$ to $C_{36}$ aryl and substituted $C_3$ to $C_{35}$ heteroaryl may be selected from H, $C_1$ to $C_{16}$ alkyl, $C_1$ to $C_{16}$ alkoxy, $C_3$ to $C_{16}$ branched alkyl, $C_3$ to $C_{16}$ cyclic alkyl, $C_3$ to $C_{16}$ branched alkoxy, $C_3$ to $C_{16}$ cyclic alkoxy, partially or perfluorinated $C_1$ to $C_{16}$ alkyl, partially or perfluorinated $C_1$ to $C_{16}$ alkoxy, partially or perdeuterated $C_1$ to $C_{16}$ alkyl, partially or perdeuterated $C_1$ to $C_{16}$ alkoxy, $C_6$ to $C_{24}$ aryl, $C_3$ to $C_{25}$ heteroaryl, —PX$(R^1)_2$, D, F or CN, wherein
    $R^1$ may be independently selected from $C_1$ to $C_{16}$ alkyl, $C_1$ to $C_{16}$ alkoxy, partially or perfluorinated $C_1$ to $C_{16}$ alkyl, partially or perfluorinated $C_1$ to $C_{16}$ alkoxy, partially or perdeuterated $C_1$ to $C_{16}$ alkyl, partially or perdeuterated $C_1$ to $C_{16}$ alkoxy, $C_6$ to $C_{18}$ aryl, $C_3$ to $C_{25}$ heteroaryl;
$Ar^2$, $Ar^3$, $Ar^4$, $Ar^5$ and $Ar^6$ are independently selected from substituted or unsubstituted $C_6$ to $C_{12}$ aryl or substituted or unsubstituted $C_4$ to $C_{10}$ heteroaryl, wherein
  the substituent of the substituted $C_6$ to $C_{12}$ aryl or substituted $C_4$ to $C_{10}$ heteroaryl may be selected from $C_1$ to $C_6$ alkyl, $C_1$ to $C_6$ alkoxy, partially or perdeuterated $C_1$ to $C_6$ alkyl, partially or perdeuterated $C_1$ to $C_6$ alkoxy, partially or perfluorinated $C_1$ to $C_6$ alkyl, partially or perfluorinated $C_1$ to $C_6$ alkoxy, D, F, or CN.

According to one embodiment of the triazine compound of formula 1 or 1a:

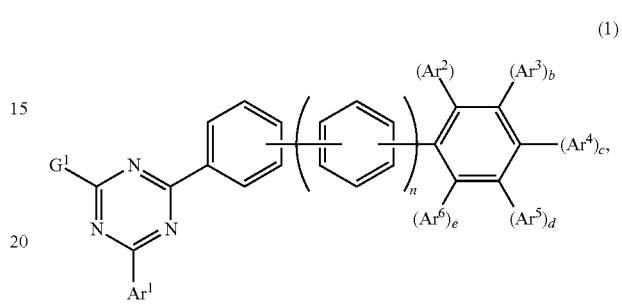

(1)

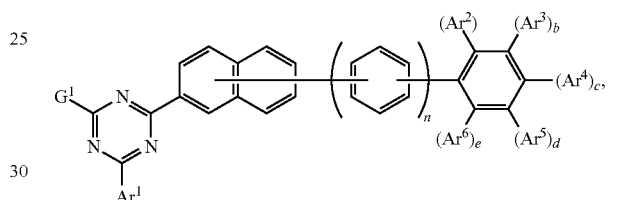
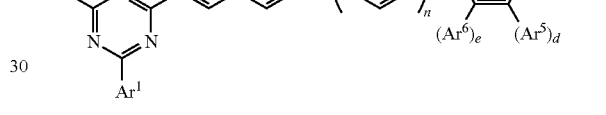

(1a)

wherein
G¹ has the formula 2:

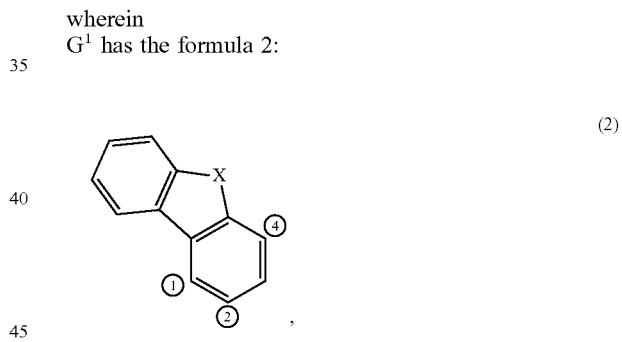

(2)

wherein
G¹ of formula 2 is linked to formula 1 to one position, selected from the positions marked by "①, ②, and ④";
X may be O, S or Se;
a, b, c, d, e may be selected from 0 or 1, wherein $2 \leq a+b+c+d+e \leq 5$;
n may be selected from 0, 1 or 2;
$Ar^1$ may be selected from substituted or unsubstituted $C_6$ to $C_{36}$ aryl, substituted or unsubstituted $C_3$ to $C_{35}$ heteroaryl, wherein
  the substituents of the substituted $C_6$ to $C_{36}$ aryl and substituted $C_3$ to $C_{35}$ heteroaryl may be selected from H, $C_1$ to $C_{16}$ alkyl, $C_1$ to $C_{16}$ alkoxy, $C_3$ to $C_{16}$ branched alkyl, $C_3$ to $C_{16}$ cyclic alkyl, $C_3$ to $C_{16}$ branched alkoxy, $C_3$ to $C_{16}$ cyclic alkoxy, partially or perfluorinated $C_1$ to $C_{16}$ alkyl, partially or perfluorinated $C_1$ to $C_{16}$ alkoxy, partially or perdeuterated $C_1$ to $C_{16}$ alkyl, partially or perdeuterated $C_1$ to $C_{16}$ alkoxy, $C_6$ to $C_{24}$ aryl, $C_3$ to $C_{25}$ heteroaryl, —PX$(R^1)_2$, D, F or CN, wherein $R^1$ may be independently selected from $C_1$ to $C_{16}$ alkyl, $C_1$ to $C_{16}$ alkoxy, partially or perfluorinated $C_1$ to $C_{16}$ alkyl, partially or perfluorinated $C_1$ to $C_{16}$ alkoxy, partially or perdeuterated $C_1$ to $C_{16}$ alkyl, partially or perdeuterated $C_1$ to $C_{16}$ alkoxy, $C_6$ to $C_{18}$ aryl, $C_3$ to $C_{25}$ heteroaryl;

$Ar^2, Ar^3, Ar^4, Ar^5$ and $Ar^6$ are independently selected from substituted or unsubstituted $C_6$ to $C_{12}$ aryl or substituted or unsubstituted $C_4$ to $C_{10}$ heteroaryl, wherein the substituent of the substituted $C_6$ to $C_{12}$ aryl or substituted $C_4$ to $C_{10}$ heteroaryl may be selected from $C_1$ to $C_6$ alkyl, $C_1$ to $C_6$ alkoxy, partially or perdeuterated $C_1$ to $C_6$ alkyl, partially or perdeuterated $C_1$ to $C_6$ alkoxy, partially or perfluorinated $C_1$ to $C_6$ alkyl, partially or perfluorinated $C_1$ to $C_6$ alkoxy, D, F, or CN;

and wherein $Ar^1$ comprises at least one $—PX(R^1)_2$ substituent.

According to one embodiment of the triazine compound of formula 1 or 1a, wherein $Ar^1$ is free of an $—PX(R^1)_2$ substituent.

According to one embodiment of the triazine compound of formula 1 or 1a:

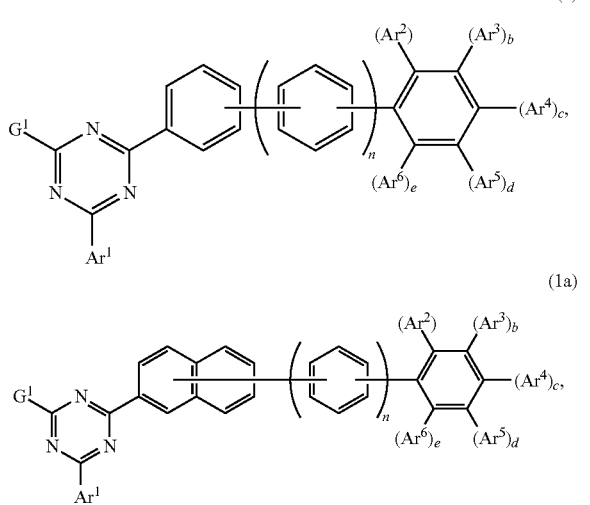

wherein
$G^1$ has the formula 2:

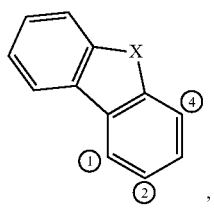

wherein
$G^1$ of formula 2 is linked to formula 1 to one position, selected from the positions marked by "①, ②, and ④";
X may be O, S or Se;
a, b, c, d, e may be selected from 0 or 1, wherein $2 \leq a+b+c+d+e \leq 5$;
n may be 0 or 1;

$Ar^1$ may be selected from unsubstituted $C_6$ to $C_{12}$ aryl;
$Ar^2, Ar^3, Ar^4, Ar^5$ and $Ar^6$ are independently selected from unsubstituted $C_6$ to $C_{12}$ aryl.

According to one embodiment of the triazine compound of formula 1, $G^1$ has the formula 2:

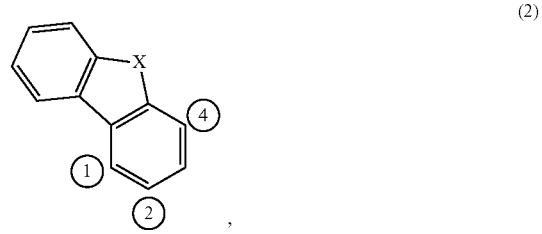

and wherein $G^1$ of formula 2 is linked to formula 1 at the position marked by "①", or "②", or "④"; preferably $G^1$ of formula 2 is linked to formula 1 at the position marked by "①", or "④"; further preferred $G^1$ of formula 2 is linked to formula 1 at the position marked by "①"; in addition preferred $G^1$ of formula 2 is linked to formula 1 at the position marked by "②"; and also preferred $G^1$ of formula 2 is linked to formula 1 at the position marked by "④".

According to one embodiment of the triazine compound of formula 1 or 1a:

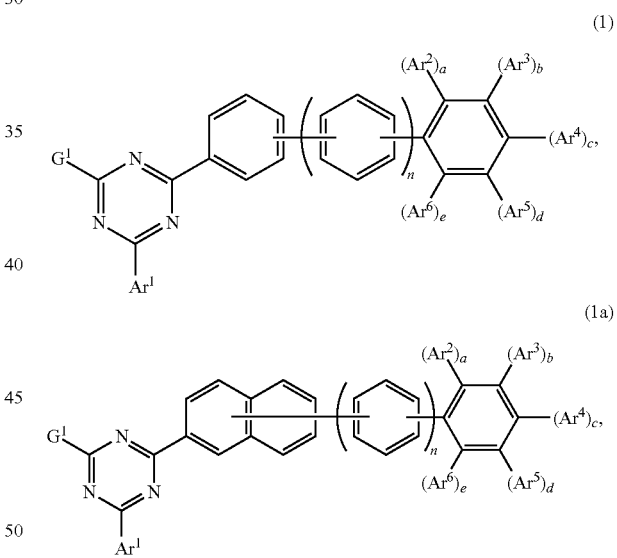

wherein
$G^1$ has the formula 2:

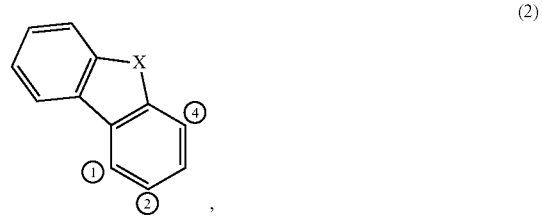

wherein
G¹ of formula 2 is linked to formula 1 to at least one position, two positions or three positions, preferably to one position, at the positions marked by "①, ②, and ④";
X may be O, S or Se;
a, b, c, d, e may be selected from 0 or 1, wherein $2 \leq a+b+c+d+e \leq 5$;
n may be selected from 0, 1 or 2,
Ar¹ may be selected from $C_1$ to $C_{16}$ alkyl, unsubstituted $C_6$ to $C_{40}$ aryl, unsubstituted $C_3$ to $C_{40}$ heteroaryl;
Ar², Ar³, Ar⁴, Ar⁵ and Ar⁶ are independently selected from unsubstituted $C_6$ to $C_{12}$ aryl or unsubstituted $C_4$ to $C_{10}$ heteroaryl; wherein
the hetero atom may be individually selected from N, O, S, B, Si, P, Se, preferably from N, O and S, and more preferred is N.

According to another embodiment of the triazine compound of formula 1 or 1a, wherein X of formula 2 may be selected from O or S.

According to another embodiment of the triazine compound of formula 1 or 1a, wherein X of formula 2 is O.

According to another embodiment of the triazine compound of formula 1 or 1a, wherein
Ar¹ may be selected from $C_1$ to $C_{12}$ alkyl, substituted or unsubstituted $C_6$ to $C_{24}$ aryl or substituted or unsubstituted $C_3$ to $C_{36}$ heteroaryl, wherein
the substituents of the substituted $C_6$ to $C_{24}$ aryl and substituted $C_3$ to $C_{36}$ heteroaryl may be selected from $C_1$ to $C_{12}$ alkyl, $C_1$ to $C_{12}$ alkoxy, $C_3$ to $C_{16}$ branched alkyl, $C_3$ to $C_{16}$ cyclic alkyl, $C_3$ to $C_{16}$ branched alkoxy, $C_3$ to $C_{16}$ cyclic alkoxy, partially or perfluorinated $C_1$ to $C_{12}$ alkyl, partially or perfluorinated $C_1$ to $C_{16}$ alkoxy, partially or perdeuterated $C_1$ to $C_{12}$ alkyl, partially or perdeuterated $C_1$ to $C_{16}$ alkoxy, $C_6$ to $C_{24}$ aryl, $C_3$ to $C_{25}$ heteroaryl, D, F or CN, preferably from $C_1$ to $C_{12}$ alkyl.

According to the present invention the term "substituted or unsubstituted $C_3$ to $C_{40}$ heteroaryl" may comprises a substituted or unsubstituted dibenzofurane, a substituted or unsubstituted dibenzothiophene, substituted or unsubstituted annelated heteroaryl, substituted or unsubstituted non-annelated heteroaryl, unsubstituted or substituted hetero arylene and unsubstituted or substituted carbazole groups.

According to the present invention for Ar¹ the term "substituted or unsubstituted $C_3$ to $C_{40}$ heteroaryl" comprises a group selected from substituted or unsubstituted dibenzofurane, a substituted or unsubstituted dibenzothiophene, substituted or unsubstituted annelated heteroaryl, substituted or unsubstituted non-annelated heteroaryl, unsubstituted or substituted hetero arylene and unsubstituted or substituted carbazole.

According to one embodiment Ar¹ may represented by an unsubstituted $C_3$ to $C_{40}$ heteroaryl, preferably an unsubstituted $C_3$ to $C_{40}$ heteroaryl group selected from dibenzofurane, dibenzothiophene, annelated heteroaryl, hetero arylene groups and carbazole groups.

According to one embodiment Ar¹, wherein the substituted or unsubstituted $C_6$ to $C_{24}$ aryl or substituted or unsubstituted $C_3$ to $C_{36}$ heteroaryl may be selected from phenyl, naphtyl, diphenyl or dibenzofurane.

According to one embodiment, the triazine compound according to formula I, wherein Ar¹ may be selected from phenyl, naphtyl, diphenyl or dibenzofurane; L is phenylene or naphtylene; a, b, c, d, e are selected from 0 or 1, wherein $2 \leq a+b+c+d+e \leq 5$, Ar² to Ar⁶ are phenyl; G=is dibenzofuran and n=1.

According to another embodiment of the triazine compound of formula 1 or 1a, wherein Ar¹ may be selected from H, unsubstituted $C_6$ to $C_{24}$ aryl, preferably a $C_6$ or $C_{12}$ aryl.

According to another embodiment of the triazine compound of formula 1 or 1a, wherein Ar¹ may be independently selected from B1 to B3, B3a, B4 to B77, wherein a) B1 to B6 are substituted or unsubstituted non-heteroaryl groups:

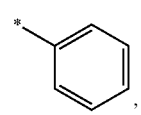
B1

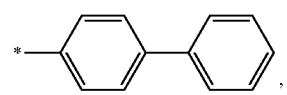
B2

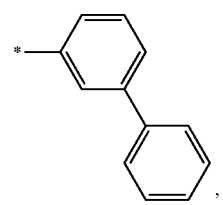
B3

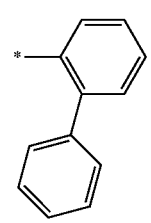
B3a

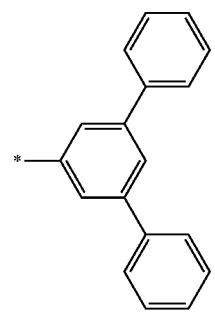
B4

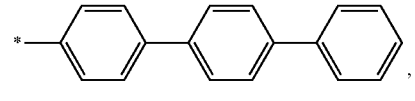
B5

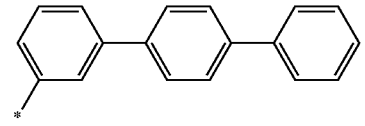
B6 or b) B7 to B23 are substituted or unsubstituted annelated non-heteroaryl groups:

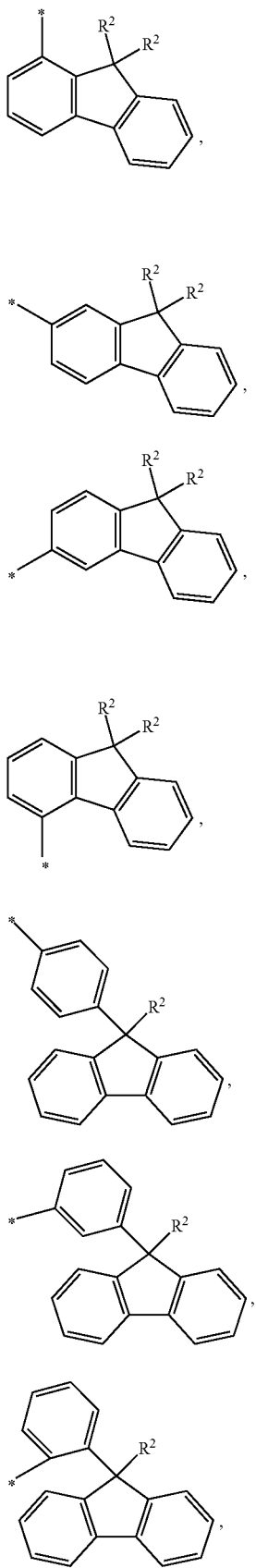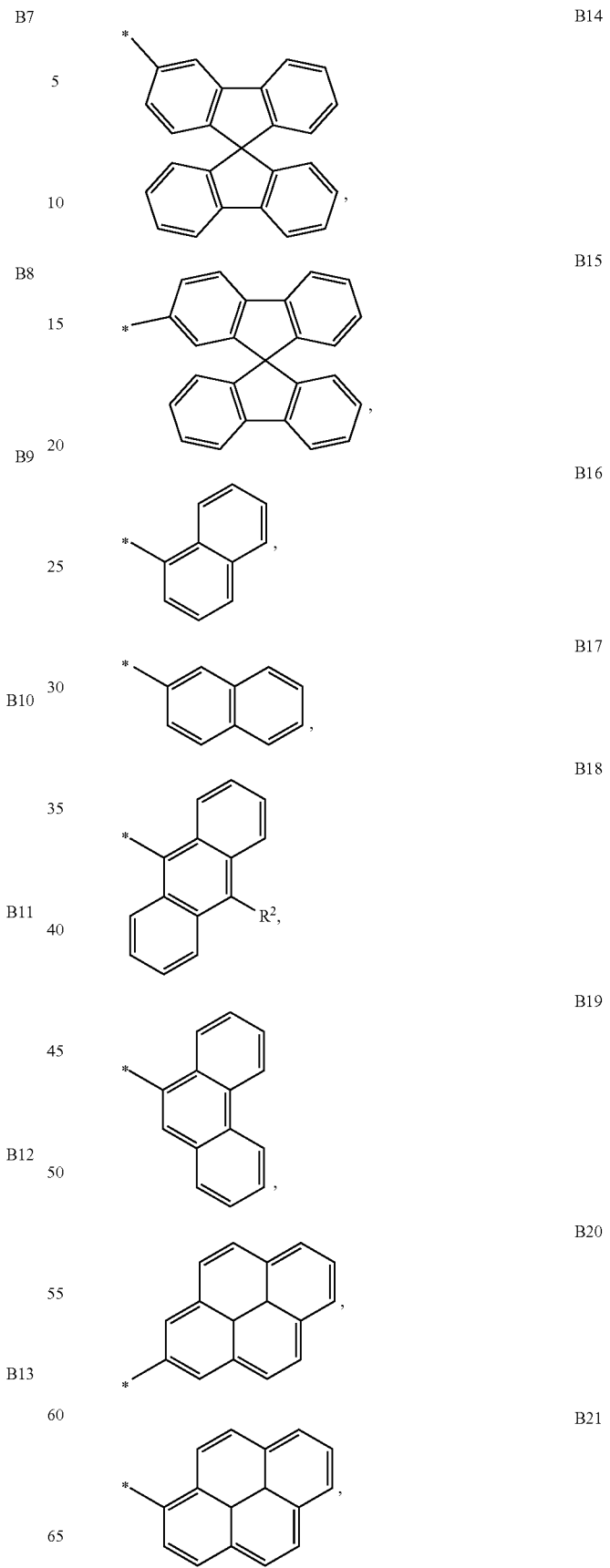

-continued
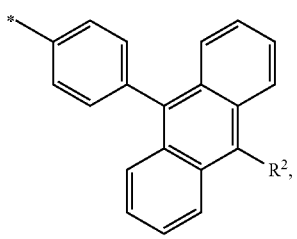
B22
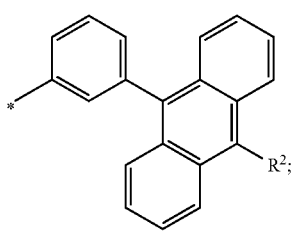
B23
or
c) B24 to B31 are dibenzofurane/dibenzothiophene group:
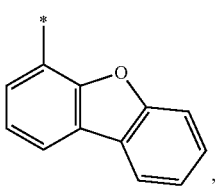
B24
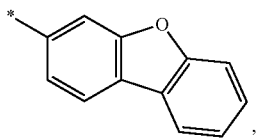
B25
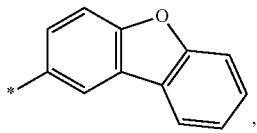
B26
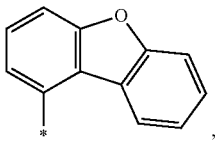
B27
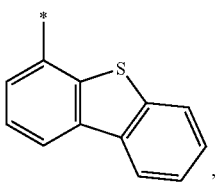
B28
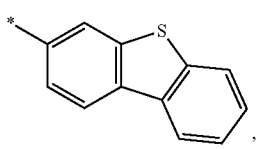
B29
-continued
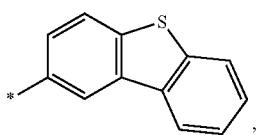
B30
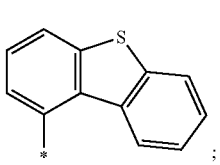
B31
or
d) B32 to B34 are unsubstituted pyridine groups:
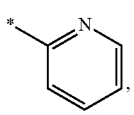
B32
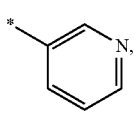
B33
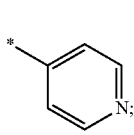
B34
or
e) B35 to B62 are unsubstituted or substituted hetero arylene groups:
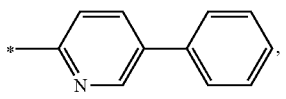
B35
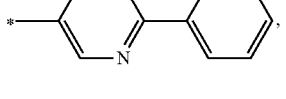
B36
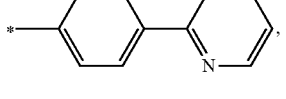
B37
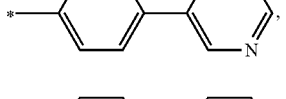
B38
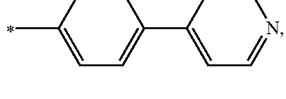
B39

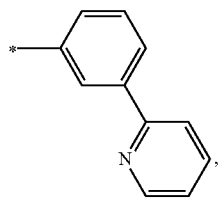 B40
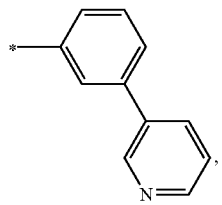 B41
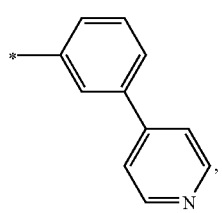 B42
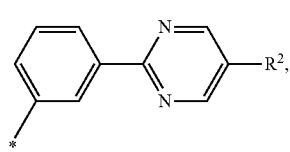 B43
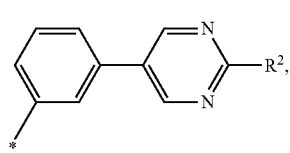 B44
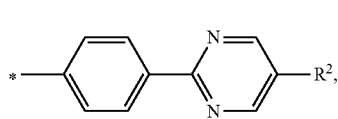 B45
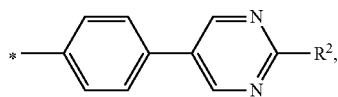 B46
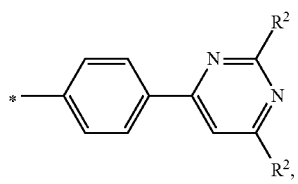 B47
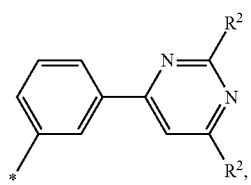 B48
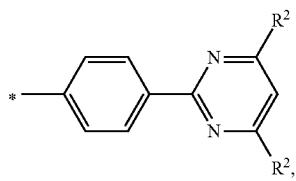 B49
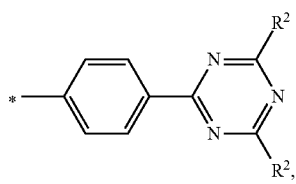 B50
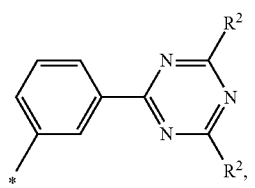 B51
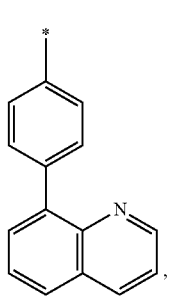 B52
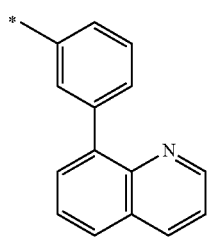 B53
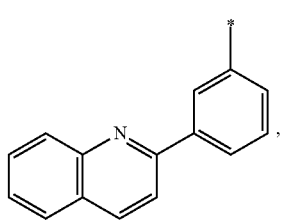 B54
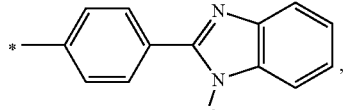 B55
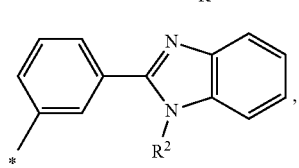 B56

-continued
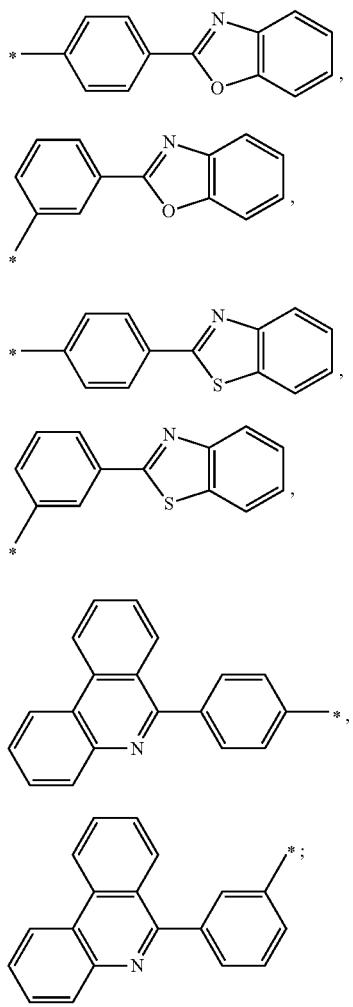
B57
B58
B59
B60
B61
B62
or
f) B63 to B65 unsubstituted annelated hetero arylene groups:
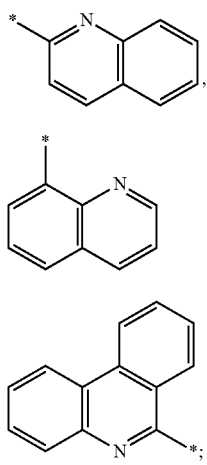
B63
B64
B65
or
g) B66 and B67 are nitrile substituted phenyl groups
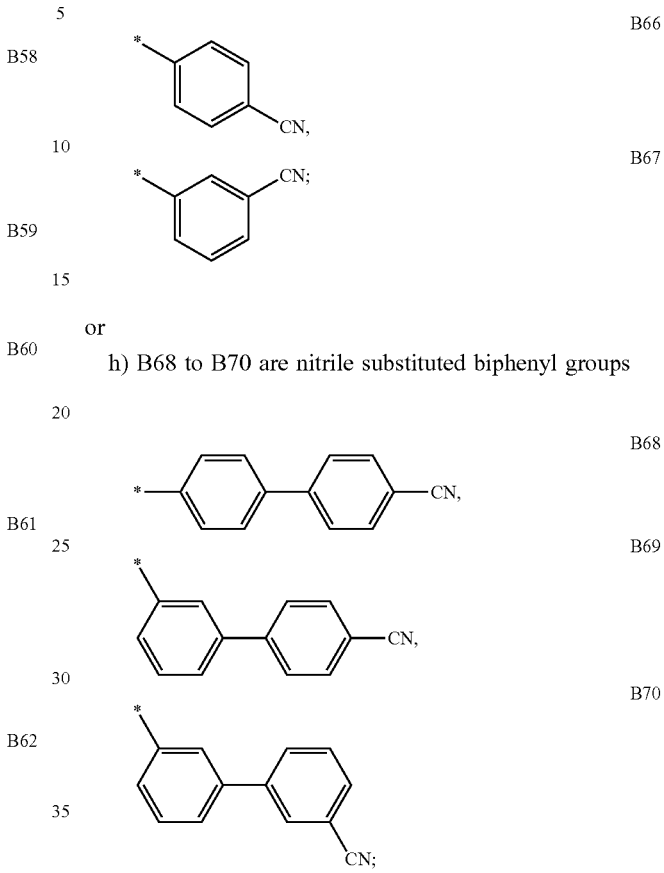
B66
B67
or
h) B68 to B70 are nitrile substituted biphenyl groups
B68
B69
B70
or
i) B71 to B77 are carbazole groups
B71
B72
B73

-continued

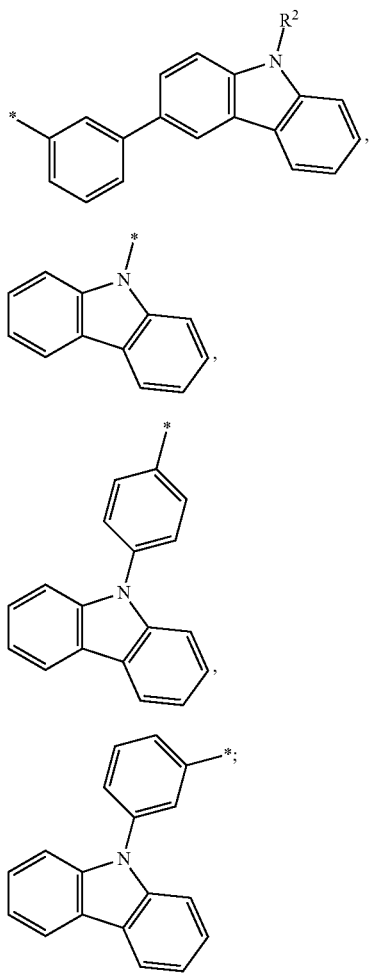

B74

B75

B76

B77 wherein
the substituent $R^2$ may be independently selected from H, $C_1$ to $C_{16}$ alkyl, partially or perfluorinated $C_1$ to $C_{16}$ alkyl, partially or perdeuterated $C_1$ to $C_{16}$ alkyl, $C_1$ to $C_{16}$ alkoxy, $C_3$ to $C_{16}$ branched alkyl, $C_3$ to $C_{16}$ cyclic alkyl, $C_3$ to $C_{16}$ branched alkoxy, $C_3$ to $C_{16}$ cyclic alkoxy, $C_6$ to $C_{24}$ aryl and $C_3$ to $C_{25}$ heteroaryl.

In another embodiment, $Ar^1$ may be selected from B1 to B6 and B16 to B23, preferably from B1 to B6, B16 to B17 and B19.

According to another embodiment of the triazine compound of formula 1 or 1a, wherein $Ar^1$ may be independently selected from structures C1 to C5:

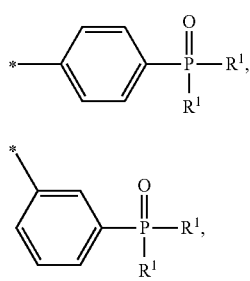

C1

C2

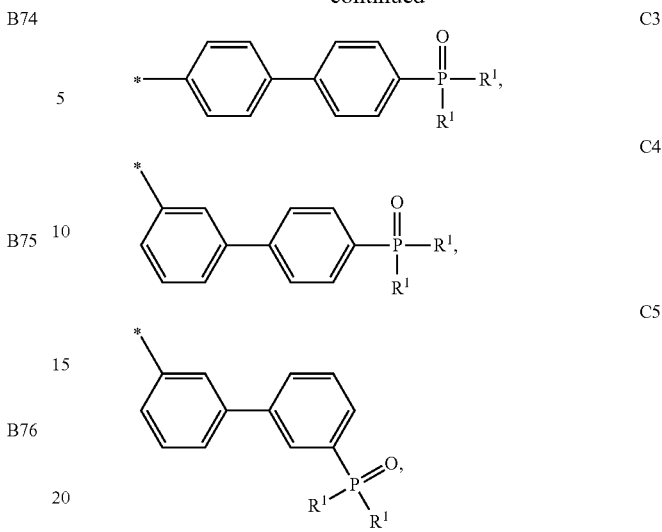

C3

C4

C5 wherein
$R^1$ is independently selected from $C_1$ to $C_{16}$ alkyl, $C_1$ to $C_{16}$ alkoxy, partially or perfluorinated $C_1$ to $C_{16}$ alkyl, partially or perfluorinated $C_1$ to $C_{16}$ alkoxy, partially or perdeuterated $C_1$ to $C_{16}$ alkyl, partially or perdeuterated $C_1$ to $C_{16}$ alkoxy, $C_6$ to $C_{18}$ aryl, $C_3$ to $C_{25}$ heteroaryl.

Preferably, $R^1$ may be independently selected from $C_1$ to $C_8$ alkyl, $C_1$ to $C_8$ alkoxy, partially or perfluorinated $C_1$ to $C_8$ alkyl, partially or perfluorinated $C_1$ to $C_8$ alkoxy, partially or perdeuterated $C_1$ to $C_8$ alkyl, partially or perdeuterated $C_1$ to $C_8$ alkoxy, $C_6$ to $C_{12}$ aryl, $C_3$ to $C_{20}$ heteroaryl.

Further preferred, $R^1$ may be independently selected from $C_1$ to $C_8$ alkyl, partially or perdeuterated $C_1$ to $C_8$ alkyl, partially or perdeuterated $C_1$ to $C_8$ alkoxy, $C_6$ to $C_{12}$ aryl, $C_3$ to $C_{20}$ heteroaryl.

More preferred, $R^1$ may be phenyl or $C_1$ to C4 alkyl, even more preferred phenyl or methyl.

According to another embodiment of the triazine compound of formula 1 or 1a,
wherein
at least one to at most three substituents of $Ar^2$, $Ar^3$, $Ar^5$ and $Ar^6$ are independently selected from unsubstituted $C_6$ to $C_{12}$ aryl or unsubstituted $C_4$ to $C_{10}$ heteroaryl.

According to another embodiment of the triazine compound of formula 1 or 1a, wherein at least one to at most three substituents of $Ar^2$, $Ar^3$, $Ar^5$ and $Ar^6$ are independently selected from unsubstituted $C_6$ to $C_{12}$ aryl.

According to another embodiment of the triazine compound of formula 1 or 1a, wherein at least one to at most three substituents of $Ar^2$, $Ar^3$, $Ar^5$ and $Ar^6$ are independently selected from phenyl, biphenyl, naphthyl, pyridyl, quinolinyl, quinazolinyl; preferably at least one $Ar^2$, $Ar^3$, $Ar^5$ and $Ar^6$ may be selected from phenyl; more preferably at least two $Ar^2$, $Ar^3$, $Ar^5$ and $Ar^6$ may be selected from phenyl; also preferred at least three of $Ar^2$, $Ar^3$, $Ar^5$ and $Ar^6$ may be selected from phenyl.

According to another embodiment of the triazine compound of formula 1 or 1a, wherein at least one to at most three substituents of $Ar^2$, $Ar^3$, $Ar^5$ and $Ar^6$ are independently selected from phenyl, biphenyl, naphthyl, pyridyl, quinolinyl, quinazolinyl.

According to another embodiment of the triazine compound of formula 1 or 1a, wherein at least one to at most three substituents of $Ar^2$, $Ar^3$, $Ar^5$ and $Ar^6$ are independently selected from phenyl.

According to another embodiment of the triazine compound of formula 1 or 1a, wherein two or three of Ar2, Ar3, Ar5, Ar6 may be selected from phenyl.

According to another embodiment of the triazine compound of formula 1 or 1a, wherein $Ar^4$ may be selected from unsubstituted $C_6$ to $C_{12}$ aryl or unsubstituted $C_4$ to $C_{10}$ heteroaryl.

According to another embodiment of the triazine compound of formula 1 or 1a, wherein $Ar^4$ may be selected from unsubstituted $C_6$ to $C_{12}$ aryl.

According to another embodiment of the triazine compound of formula 1 or 1a, wherein $Ar^4$ may be selected from phenyl, biphenyl, naphthyl, pyridyl, quinolinyl, quinazolinyl.

According to another embodiment of the triazine compound of formula 1 or 1a, wherein $Ar^4$ may be phenyl.

According to another embodiment of the triazine compound of formula 1 or 1a, wherein $Ar^4$ are independently selected from unsubstituted $C_6$ to $C_{12}$ aryl or unsubstituted $C_4$ to $C_{10}$ heteroaryl; preferably $Ar^4$ are independently selected from phenyl, biphenyl, naphthyl, pyridyl, quinolinyl, quinazolinyl; further preferred $Ar^4$ is selected from phenyl; or $Ar^3$ and/or $Ar^4$ are independently selected from unsubstituted $C_6$ to $C_{12}$ aryl, unsubstituted $C_4$ to $C_{10}$ heteroaryl and phenyl, preferably phenyl.

According to another embodiment of the triazine compound of formula 1 or 1a,
wherein
three of $Ar^2$, $Ar^3$, $Ar^5$, $Ar^6$ and in addition $Ar^4$ may be selected from phenyl.

According to another embodiment of the triazine compound of formula 1 or 1a, wherein n=0 or 1, preferably n=0. According to another embodiment of the triazine compound of formula 1 or 1a, wherein n=0. According to another embodiment of the triazine compound of formula 1 or 1a, wherein n=1. According to another embodiment of the triazine compound of formula 1 or 1a, wherein n=2.

According to another embodiment of the triazine compound of formula 1 or 1a, wherein
a=1, and at least one of b, c, d and e is 1; or
b=1, and at least one of a, c, d and e is 1; or
c=1, and at least one of a, b, d and e is 1; or
d=1, and at least one of a, b, c and e is 1; or
e=1, and at least one of a, b, c and d is 1; or
a=1, and at least two of b, c, d and e are 1; or
b=1, and at least two of a, c, d and e are 1; or
c=1, and at least two of a, b, d and e are 1; or
d=1, and at least two of a, b, c and e are 1; or
e=1, and at least two of a, b, c and d are 1; or
a=1, and at least three of b, c, d and e are 1; or
b=1, and at least three of a, c, d and e are 1; or
c=1, and at least three of a, b, d and e are 1; or
d=1, and at least three of a, b, c and e are 1; or
e=1, and at least three of a, b, c and d are 1; or
a, b, c, d and e are 1; with the provision that a, b, c, d or e if not otherwise stated is 0.

According to another embodiment of the triazine compound of formula 1 or 1a, wherein a and e are 1; or b and e are 1; or c and e are 1; or d and e are 1; with the provision that a, b, c, d or e if not otherwise stated is 0.

According to another embodiment of the triazine compound of formula 1 or 1a, wherein a and d are 1; or b and d are 1; or c and d are 1; with the provision that a, b, c, d or e if not otherwise stated is 0.

According to another embodiment of the triazine compound of formula 1 or 1a, wherein a and c are 1; or b and c are 1; or c and e are 1; with the provision that a, b, c, d or e if not otherwise stated is 0.

According to another embodiment of the triazine compound of formula 1 or 1a, wherein a and b are 1; or c and b are 1; or d and b are 1; with the provision that a, b, c, d or e if not otherwise stated is 0.

According to another embodiment of the triazine compound of formula 1 or 1a, wherein a, b and e are 1; or a, b and d are 1; or a, b and c are 1; with the provision that a, b, c, d or e if not otherwise stated is 0.

According to another embodiment of the triazine compound of formula 1 or 1a, wherein b, c and e are 1; or b, c and d are 1; with the provision that a, b, c, d or e if not otherwise stated is 0.

According to another embodiment of the triazine compound of formula 1 or 1a, wherein c, d and e are 1; or c, d and a are 1; with the provision that a, b, c, d or e if not otherwise stated is 0.

According to another embodiment of the triazine compound of formula 1 or 1a, wherein a, b, c and d are 1; or a, b, c and e are 1; or b, c, d and e are 1; or a, b, d and e are 1; with the provision that a, b, c, d or e if not otherwise stated is 0.

According to another embodiment of the triazine compound of formula 1 or 1a, the triazine compound may be selected from D1 to D36:

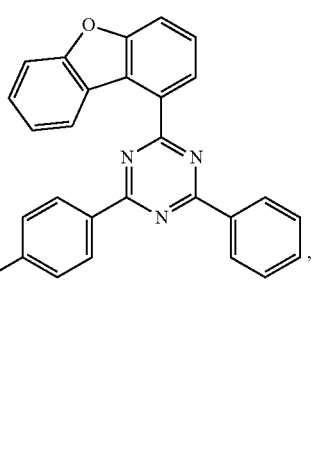

D1

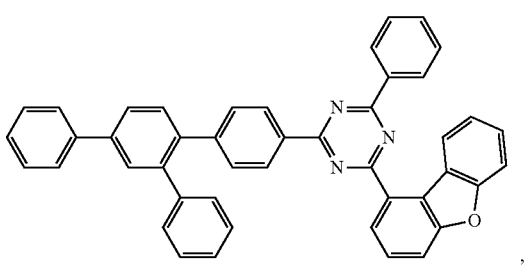

D2

-continued
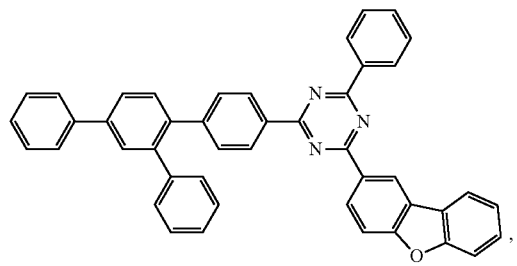
D3
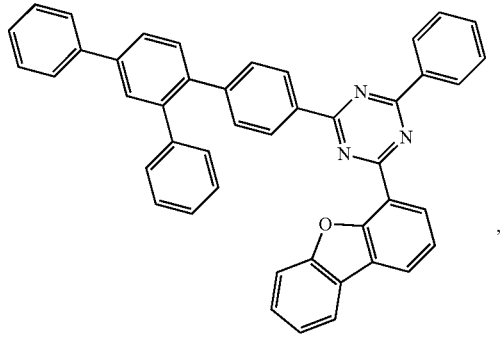
D4
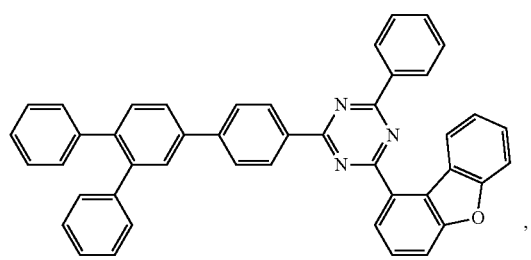
D5
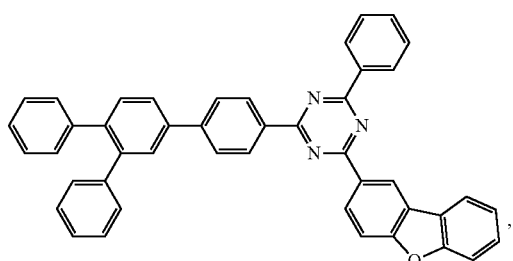
D6
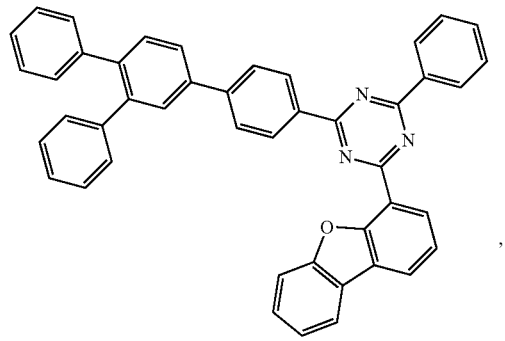
D7
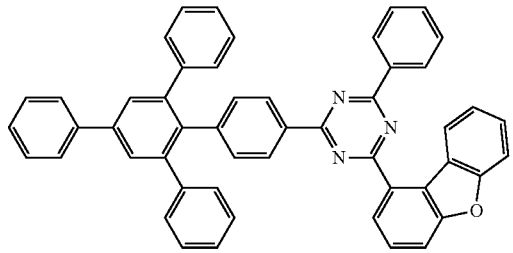
D8
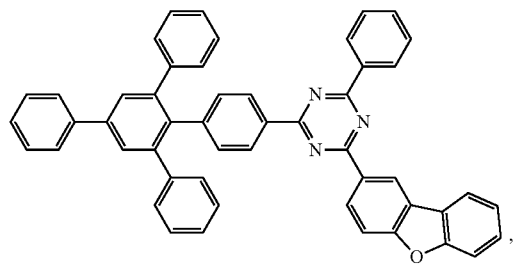
D9
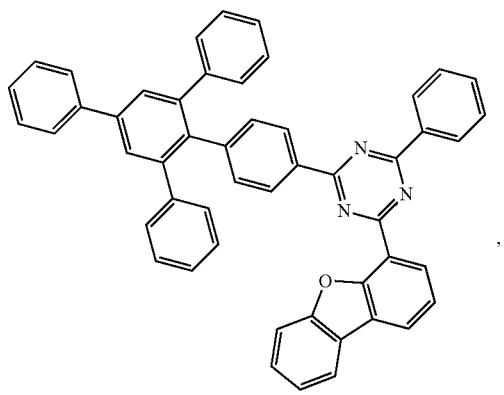
D10

-continued
D11
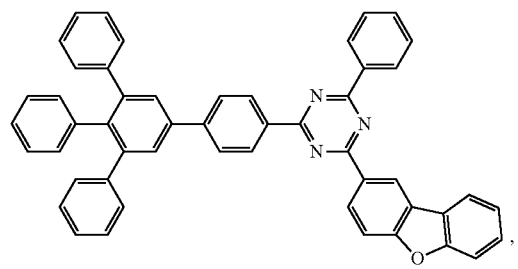
D12
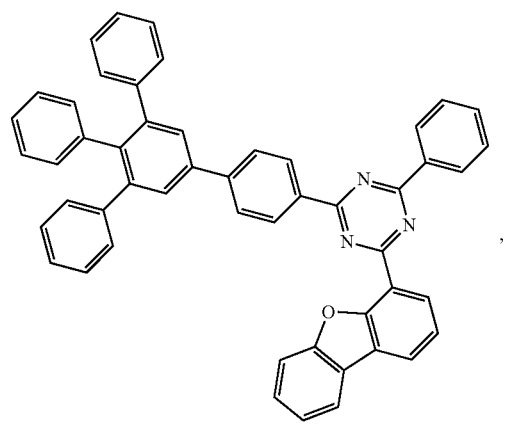
D13
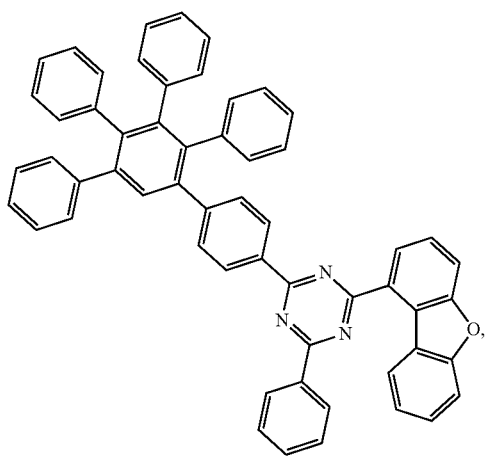
D14
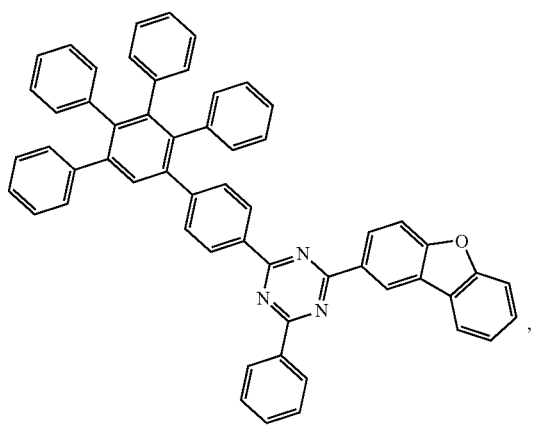
D15
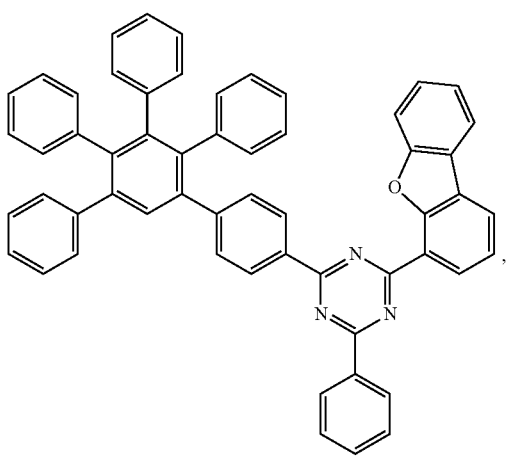
D16
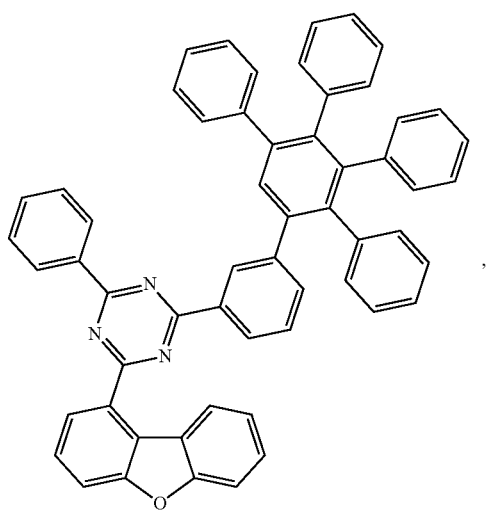

-continued
D17
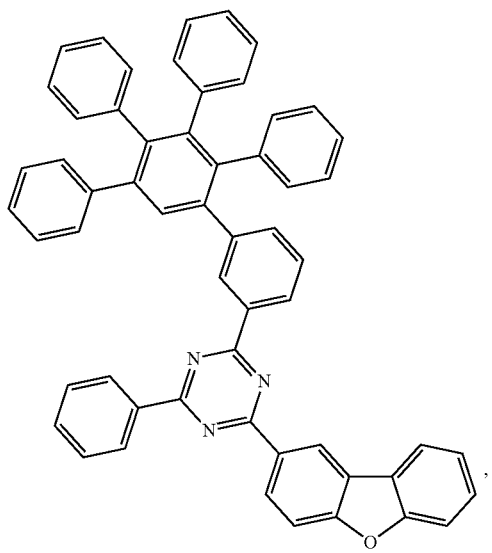
D18
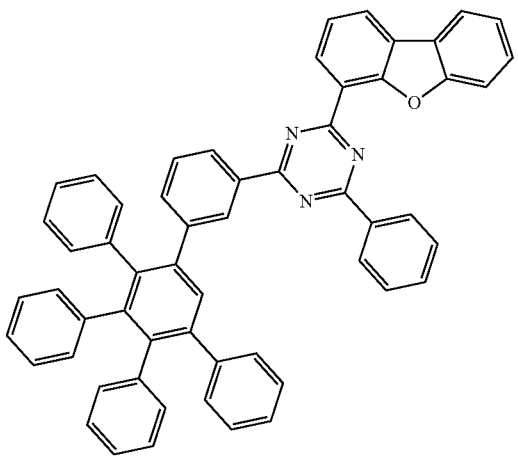
D19
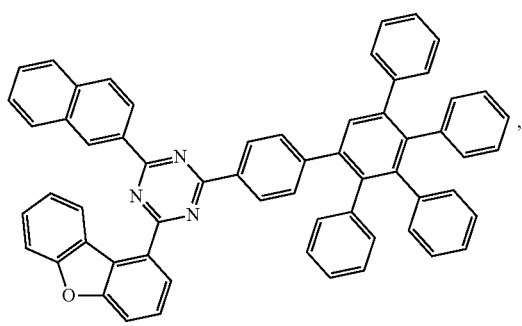
D20
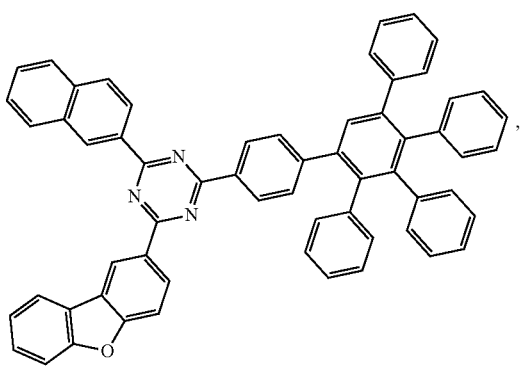
D21
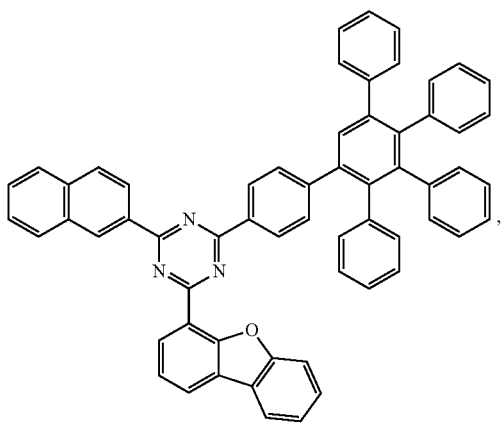
D22
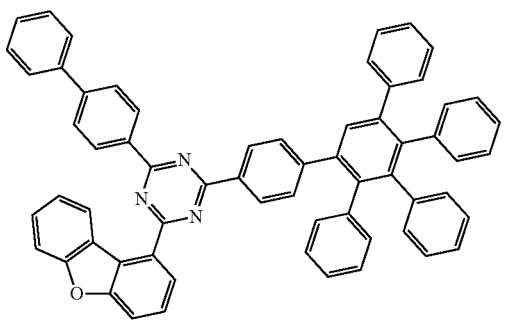

-continued
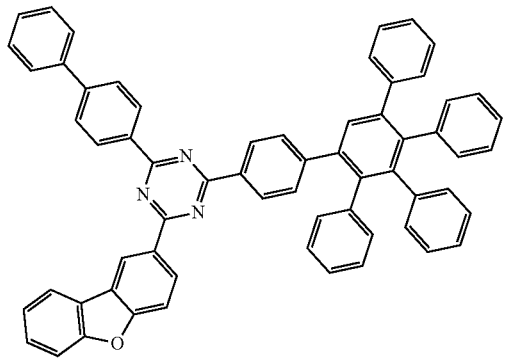
D23
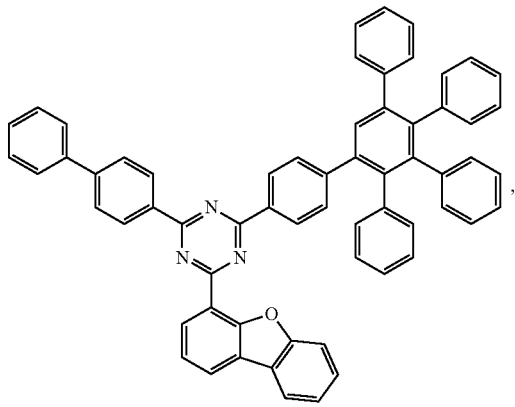
D24
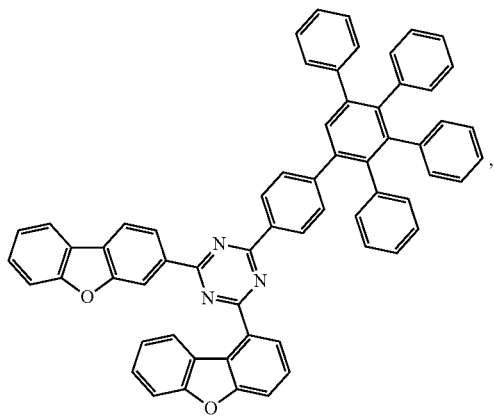
D25
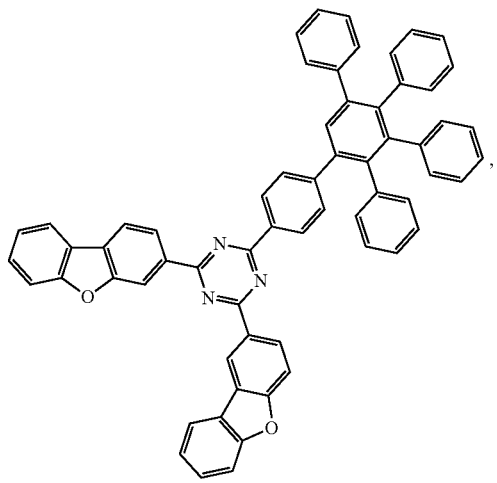
D26
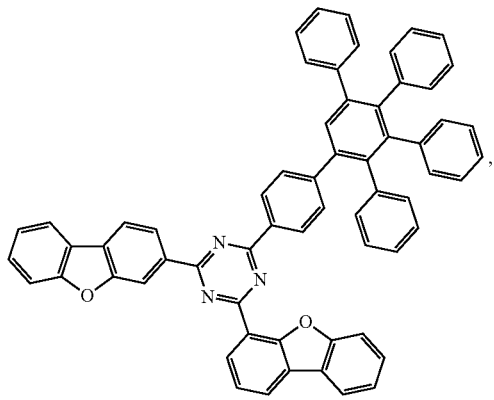
D27
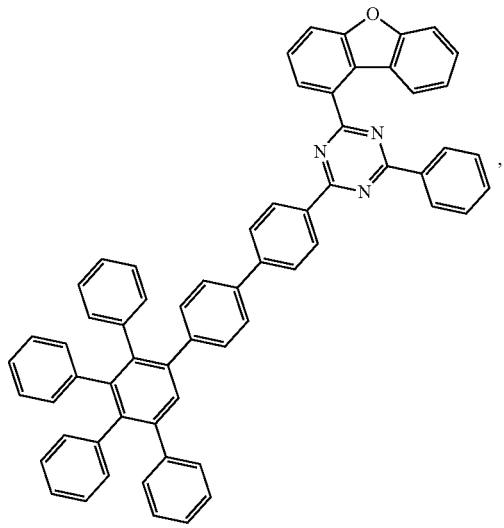
D28

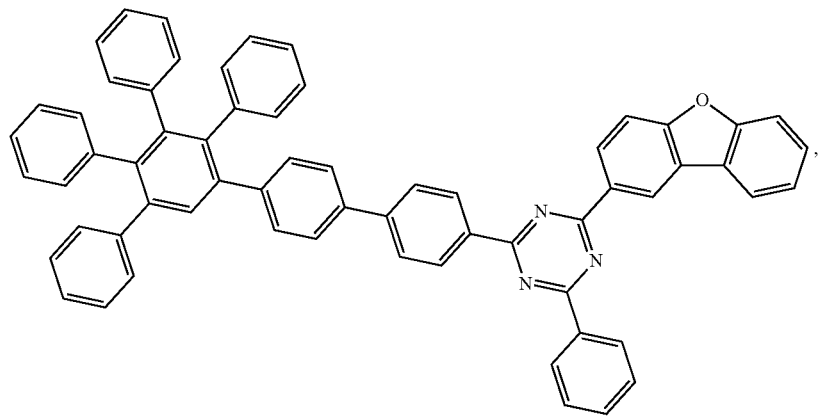
D29
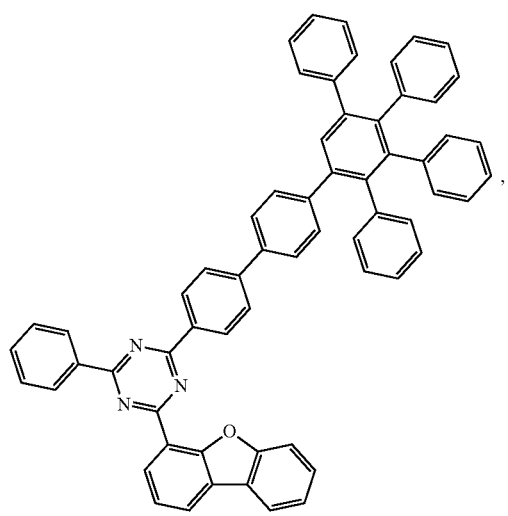
D30
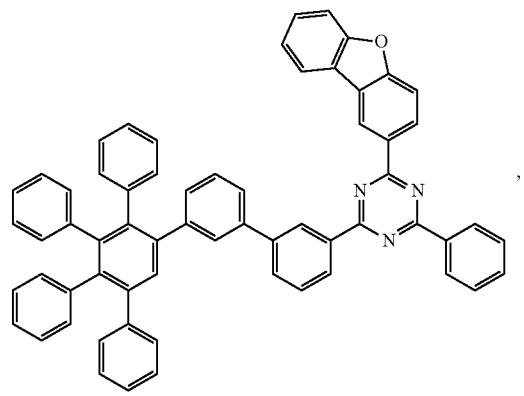
D31
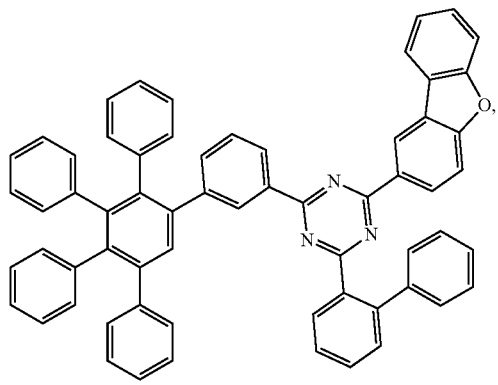
D32
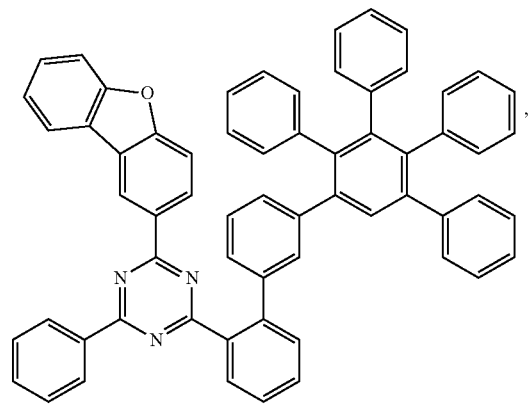
D33

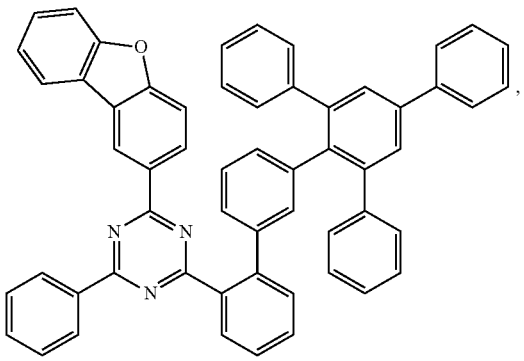 D34

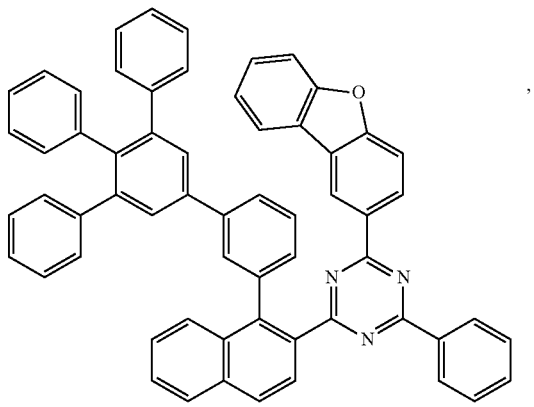 D35

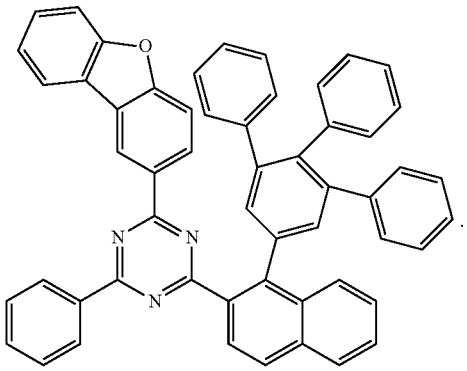 D36

According to an aspect the triazine compound of formula 1 and/or 1a can be used as a matrix material for a dopant material.

According to an aspect the triazine compound of formula 1 and/or 1a can be used as a layer material. According to an aspect the layer material can be an organic semiconductor layer. According to an aspect the layer material can be a charge generation layer. According to an aspect the organic semiconductor layer can be comprised in a p-n junction. According to an aspect the organic semiconductor layer comprises the compound of formula 1 and/or 1a as a first matrix material. According to an aspect the organic semiconductor layer consists of a compound of formula 1 and/or 1a.

According to an aspect the organic semiconductor layer does not contain a dopant or an additive. According to an aspect the organic semiconductor layer contains a dopant or an additive.

According to an aspect the layer material can be an organic semiconductor layer, which is used for an organic electronic device. For example, the organic electronic device can be an OLED or there like.

The triazine compounds represented by formula 1 and/or 1a have strong electron transport characteristics to increase charge mobility and/or stability and thereby to improve luminance efficiency, voltage characteristics, and/or lifetime characteristics.

The triazine compounds represented by formula 1 and/or 1a have high electron mobility and a low operating voltage.

The triazine compounds represented by formula 1 and 1a and an organic semiconductor layer consisting or comprising of triazine compound of formula 1 and 1a may be non-emissive.

In the context of the present specification the term "essentially non-emissive" or "non-emitting" means that the contribution of the triazine compound or layer to the visible emission spectrum from the device is less than 10%, preferably less than 5% relative to the visible emission spectrum. The visible emission spectrum is an emission spectrum with a wavelength of about ≥380 nm to about ≤780 nm.

Preferably, the organic semiconductor layer comprising the triazine compound of formula 1 and 1a is essentially non-emissive or non-emitting.

The term "free of", "does not contain", "does not comprise" does not exclude impurities which may be present in the triazine compounds prior to deposition. Impurities have no technical effect with respect to the object achieved by the present invention.

The operating voltage, also named U, is measured in Volt (V) at 10 milliAmpere per square centimeter (mA/cm2).

The candela per Ampere efficiency, also named cd/A efficiency, is measured in candela per ampere at 10 milli-Ampere per square centimeter (mA/cm2).

The external quantum efficiency, also named EQE, is measured in percent (%).

The color space is described by coordinates CIE-x and CIE-y (International Commission on Illumination 1931). For blue emission the CIE-y is of particular importance. A smaller CIE-y denotes a deeper blue color.

The highest occupied molecular orbital, also named HOMO, and lowest unoccupied molecular orbital, also named LUMO, are measured in electron volt (eV).

The rate onset temperature is measured in ° C. and describes the VTE source temperature at which measurable evaporation of a compound commences at a pressure of less than $10^{-5}$ mbar.

The term "OLED", "organic light emitting diode", "organic light emitting device", "organic optoelectronic device" and "organic light-emitting diode" are simultaneously used and have the same meaning.

The term "transition metal" means and comprises any element in the d-block of the periodic table, which comprises groups 3 to 12 elements on the periodic table.

The term "group III to VI metal" means and comprises any metal in groups III to VI of the periodic table.

As used herein, "weight percent", "wt.-%", "percent by weight", "% by weight", and variations thereof refer to a composition, component, substance or agent as the weight of that composition, component, substance or agent of the respective electron transport layer divided by the total weight of the composition thereof and multiplied by 100. It is understood that the total weight percent amount of all components, substances or agents of the respective electron transport layer are selected such that it does not exceed 100 wt.-%.

As used herein, "volume percent", "vol.-%", "percent by volume", "% by volume", and variations thereof refer to an elemental metal, a composition, component, substance or agent as the volume of that elemental metal, component, substance or agent of the respective electron transport layer divided by the total volume of the respective electron transport layer thereof and multiplied by 100. It is understood that the total volume percent amount of all elemental metal, components, substances or agents of the respective cathode electrode layer are selected such that it does not exceed 100 vol.-%.

All numeric values are herein assumed to be modified by the term "about", whether or not explicitly indicated. As used herein, the term "about" refers to variation in the numerical quantity that can occur.

Whether or not modified by the term "about", the claims include equivalents to the quantities.

It should be noted that, as used in this specification and the appended claims, the singular forms "a", "an", and "the" include plural referents unless the content clearly dictates otherwise.

It should be noted that, as used in this specification and the appended claims, "*" if not otherwise defined indicates the chemical bonding position.

The anode electrode and cathode electrode may be described as anode electrode/cathode electrode or anode electrode/cathode electrode or anode electrode layer/cathode electrode layer.

According to another aspect, an organic optoelectronic device comprises an anode layer and a cathode layer facing each other and at least one organic semiconductor layer between the anode layer and the cathode layer, wherein the organic semiconductor layer comprises or consists of the triazine compound of formula 1 and/or 1a.

According to yet another aspect, a display device comprising the organic electronic device, which can be an organic optoelectronic device, is provided.

In the present specification, when a definition is not otherwise provided, an "alkyl group" may refer to an aliphatic hydrocarbon group. The alkyl group may refer to "a saturated alkyl group" without any double bond or triple bond. The alkyl group may be a linear, cyclic or branched alkyl group.

The term "alkyl group" includes $C_1$ to $C_{16}$ alkyl, $C_3$ to $C_{16}$ branched alkyl, and $C_3$ to $C_{16}$ cyclic alkyl.

The alkyl group may be a $C_1$ to $C_{16}$ alkyl group, or preferably a $C_1$ to $C_{12}$ alkyl group. More specifically, the alkyl group may be a $C_1$ to $C_{14}$ alkyl group, or preferably a $C_1$ to $C_{10}$ alkyl group or a $C_1$ to $C_6$ alkyl group. For example, a $C_1$ to $C_4$ alkyl group comprises 1 to 4 carbons in alkyl chain, and may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a tert-butyl group, a pentyl group, a hexyl group, a cyclopropyl group, a cyclobutyl group, a cyclopentyl group, a cyclohexyl group, and the like.

In the present specification $R^1$ of $—PX(R^1)_2$ can be independently selected from $C_1$ to $C_{16}$ alkyl, $C_1$ to $C_{16}$ alkoxy, partially or perfluorinated $C_1$ to $C_{16}$ alkyl, partially or perfluorinated $C_1$ to $C_{16}$ alkoxy, partially or perdeuterated $C_1$ to $C_{16}$ alkyl, partially or perdeuterated $C_1$ to $C_{16}$ alkoxy, $C_6$ to $C_{18}$ aryl, $C_3$ to $C_{25}$ heteroaryl, that means that both substituents of $R^1$ can be same or different selected, preferably both $R^1$ of $—PX(R^1)_2$ are selected the same.

In the present specification "arylene group" may refer to a group comprising at least one hydrocarbon aromatic moiety, and all the elements of the hydrocarbon aromatic moiety may have p-orbitals which form conjugation, for example a phenyl group, a naphthyl group, an anthracenyl group, a phenanthrenyl group, a pyrenyl group, a fluorenyl group and the like.

The term "heteroarylene" may refer to aromatic heterocycles with at least one heteroatom, and all the elements of the hydrocarbon heteroaromatic moiety may have p-orbitals which form conjugation. The heteroatom may be selected from N, O, S, B, Si, P, Se, preferably from N, O and S.

A heteroarylene ring may comprise at least 1 to 3 heteroatoms. Preferably a heteroarylene ring may comprise at least 1 to 3 heteroatoms individually selected from N, S and/or O.

Further preferred in addition to the triazine group of formula 1 and 1a, formula 1 and 1a comprises at least one additional heteroaryl/ene ring may comprise at least 1 to 3 N-atoms, or at least 1 to 2-N atoms or at least one N-atom.

According to another preferred embodiment the triazine compound according to formula 1 and/or 1a may comprise:
at least 6 to 25 aromatic rings, preferably at least 7 to 22 aromatic rings, further preferred at least 8 to 20 aromatic rings, in addition preferred at least 9 to 15 aromatic rings and more preferred at least 10 to 14 aromatic rings; wherein
at least 2 to 5, preferably 3 to 4 or 2 to 3, are heteroaromatic rings.

According to one embodiment the triazine compound according to formula 1 and/or 1a:
comprises at least about 6 to about 20 aromatic rings, preferably at least about 7 to about 18 aromatic rings, further preferred at least about 9 to about 16 aromatic rings, in addition preferred at least about 10 to about 15 aromatic rings and more preferred at least about 11 to about 14 aromatic rings; and/or
the triazine compound of formula 1 and/or 1a comprises at least about 2 to about 6, preferably about 3 to about 5 or about 2 to about 4, hetero aromatic rings, wherein the hetero atoms can be selected from N, O, S; and/or
comprises at least one fluorene ring and at least one hetero-fluorene ring, wherein the hetero atoms can be selected from N, O, S; and/or
comprises at least one triazine ring, or at least two triazine rings.

According to a further preferred embodiment the triazine compound of formula 1 and/or 1a comprises at least 2 to 7, preferably 2 to 5, or 2 to 3 hetero aromatic rings.

According to a further preferred embodiment the triazine compound of formula 1 and/or 1a comprises at least 2 to 7, preferably 2 to 5, or 2 to 3 hetero aromatic rings, wherein at least one of the aromatic rings is a five member hetero aromatic ring.

According to a further preferred embodiment the triazine compound of formula 1 and/or 1a comprises at least 3 to 7, preferably 3 to 6, or 3 to 5 hetero aromatic rings, wherein at least two of the hetero aromatic rings are five member hetero-aromatic-rings.

According to one embodiment the triazine compound according to formula 1 and/or 1a may comprise at least 6 to 12 non-hetero aromatic rings and 2 to 3 hetero aromatic rings.

According to one preferred embodiment the triazine compound according to formula 1 and/or 1a may comprise at least 7 to 12 non-hetero aromatic rings and 2 to 5 hetero aromatic rings.

According to one preferred embodiment the triazine compound according to formula 1 and/or 1a may comprise at least 7 to 11 non-hetero aromatic rings and 2 to 3 hetero aromatic rings.

According to another embodiment of formula 1 and/or 1a, wherein for $Ar^2$, $Ar^3$, $Ar^4$, $Ar^5$ and/or $Ar^6$ at least one heteroarylene group is selected from pyridinyl, quinolinyl or quinazolinyl.

Melting Point

The melting point (mp) is determined as peak temperatures from the DSC curves of the above TGA-DSC measurement or from separate DSC measurements (Mettler Toledo DSC822e, heating of samples from room temperature to completeness of melting with heating rate 10 K/min under a stream of pure nitrogen. Sample amounts of 4 to 6 mg are placed in a 40 μL Mettler Toledo aluminum pan with lid, a <1 mm hole is pierced into the lid).

According to another embodiment the triazine compound of formula 1 and/or 1a may have a melting point of about ≥170° C. and about ≤380° C., preferably about ≥180° C. and about ≤370° C., further preferred about ≥190° C. and about ≤360° C., in addition preferred about ≥200° C. and about ≤350° C., also preferred about ≥200° C. and about ≤340° C.

Glass Transition Temperature

The glass transition temperature is measured under nitrogen and using a heating rate of 10 K per min in a Mettler Toledo DSC 822e differential scanning calorimeter as described in DIN EN ISO 11357, published in March 2010.

According to another embodiment the triazine compound of formula 1 and/or 1a may have a glass transition temperature Tg of about ≥115° C. and about ≤380° C., preferably about ≥120° C. and about ≤350° C., further preferred about ≥120° C. and about ≤320° C., in addition preferred about ≥120° C. and about ≤200° C. and also preferred about ≥125° C. and about ≤180° C.

According to another embodiment the triazine compound of formula 1 and/or 1a may have a glass transition temperature Tg of about ≥110° C. and about ≤200° C.

Rate Onset Temperature

The rate onset temperature is determined by loading 100 mg compound into a VTE source. The VTE source is heated at a constant rate of 15 K/min at a pressure of less than $10^{-5}$ mbar and the temperature inside the source measured with a thermocouple. Evaporation of the compound is detected with a QCM detector which detects deposition of the compound on the quartz crystal of the detector. The deposition rate on the quartz crystal is measured in Angstrom per second. To determine the rate onset temperature, the deposition rate is plotted against the VTE source temperature. The rate onset is the temperature at which noticeable deposition on the QCM detector occurs. For accurate results, the VTE source is heated and cooled three time and only results from the second and third run are used to determine the rate onset temperature.

To achieve good control over the evaporation rate of an organic compound, the rate onset temperature may be in the range of 200 to 255° C. If the rate onset temperature is below 200° C. the evaporation may be too rapid and therefore difficult to control. If the rate onset temperature is above 255° C. the evaporation rate may be too low which may result in low takt time and decomposition of the organic compound in VTE source may occur due to prolonged exposure to elevated temperatures.

The rate onset temperature is an indirect measure of the volatility of a compound. The higher the rate onset temperature the lower is the volatility of a compound.

According to another embodiment the triazine compound of formula 1 and/or 1a may have a rate onset temperature $T_{RO}$ of about ≥200° C. and about ≤350° C., preferably about ≥210° C. and about ≤350° C., further preferred about ≥230° C. and about ≤320° C., in addition preferred about ≥230° C. and about ≤300° C.

Dipole Moment

The dipole moment $|\vec{\mu}|$ of a molecule containing N atoms is given by:

$$\vec{\mu} = \sum_{i}^{N} q_i \vec{r}_i$$

$$|\vec{\mu}| = \sqrt{\mu_x^2 + \mu_y^2 + \mu_z^2}$$

where $q_i$ and $\vec{r}_i$ are the partial charge and position of atom i in the molecule.

The dipole moment is determined by a semi-empirical molecular orbital method. The geometries of the molecular structures are optimized using the hybrid functional B3LYP with the 6-31G* basis set in the gas phase as implemented in the program package TURBOMOLE V6.5 (TURBOMOLE GmbH, Litzenhardtstrasse 19, 76135 Karlsruhe, Germany). If more than one conformation is viable, the conformation with the lowest total energy is selected to determine the bond lengths of the molecules.

According to one embodiment the triazine compounds according to formula 1 and/or 1a may have a dipole moment (Debye) in the range from about ≥0.1 to about ≤6.00, preferably from about ≥0.0.15 to about ≤5.60.

The range of the dipole moment (max-min) is the maximum dipole moment value minus the minimum dipole moment value for the different possible molecular orientations of the same compound. The range of the dipole moment of a compound of formula (1) may be between 0 and 1 Debye, preferably between 0 and 0.5 Debye.

The range of the dipole moment of a compound of formula (1) wherein $G^1$ of formula 2 is linked to formula 1 and/or 1a at the position marked by "①" may be between 0 and 1 Debye, preferably between 0 and 0.5 Debye.

The range of the dipole moment of a compound of formula (1) wherein $G^1$ of formula 2 is linked to formula 1 and/or 1a at the position marked by "④"; may be between 0 and 1 Debye, preferably between 0 and 0.5 Debye.

Calculated HOMO and LUMO

The HOMO and LUMO are calculated with the program package TURBOMOLE V6.5. The optimized geometries and the HOMO and LUMO energy levels of the molecular structures are determined by applying the hybrid functional B3LYP with a 6-31G* basis set in the gas phase. If more than one conformation is viable, the conformation with the lowest total energy is selected.

According to one embodiment the triazine compounds according to formula 1 and/or 1a may have a LUMO energy level (eV), in the absolute scale taking vacuum energy level as zero, computed by the TURBOMOLE V6.5 program package using hybrid functional B3LYP and Gaussian 6-31G* basis set, in the range from about—2.00 eV to about—1.60 eV, preferably from about—1.99 eV to about—1.61 eV, further preferred from about—1.98 eV to about—1.62 eV, also preferred from about—1.97 eV to about—1.63 eV, in addition preferred from about—1.96 eV to about—1.64 eV, or further preferred about -1.95 eV to about—1.67 eV.

Reduction Potential

The reduction potential is determined by cyclic voltammetry with potenioststic device Metrohm PGSTAT30 and software Metrohm Autolab GPES at room temperature. The redox potentials given at particular compounds were measured in an argon de-aerated, dry 0.1M THE solution of the tested substance, under argon atmosphere, with 0.1M tetrabutylammonium hexafluorophosphate supporting electrolyte, between platinum working electrodes and with an Ag/AgCl pseudo-standard electrode (Metrohm Silver rod electrode), consisting of a silver wire covered by silver chloride and immersed directly in the measured solution, with the scan rate 100 mV/s. The first run was done in the broadest range of the potential set on the working electrodes, and the range was then adjusted within subsequent runs appropriately. The final three runs were done with the addition of ferrocene (in 0.1M concentration) as the standard. The average of potentials corresponding to cathodic and anodic peak of the studied compound, after subtraction of the average of cathodic and anodic potentials observed for the standard Fc+/Fc redox couple, afforded finally the values reported above. All studied compounds as well as the reported comparative compounds showed well-defined reversible electrochemical behaviour.

Technical Effect

Surprisingly, it was found that the triazine compounds of formula 1 and/or 1a and the inventive organic electronic devices solve the problem underlying the present invention by being superior over the organic electroluminescent devices and compounds known in the art, in particular with respect to cd/A efficiency, also referred to as current efficiency and to lifetime. At the same time the operating voltage is kept at a similar or even improved level which is important for reducing power consumption and increasing battery life, for example of a mobile display device. High cd/A efficiency is important for high efficiency and thereby increased battery life of a mobile device, for example a mobile display device. Long lifetime at high current density is important for the longevity of a device which is run at high brightness.

It was additional surprisingly found that the calculated LUMO level of triazine compounds of formula 1 and/or 1a is significantly more negative than the LUMO of the state of the art.

The inventors have surprisingly found that particular good performance can be achieved when using the organic electroluminescent device as a fluorescent blue device.

The specific arrangements mentioned herein as preferred were found to be particularly advantageous.

Likewise, some compounds falling within the scope of the broadest definition of the present invention have surprisingly be found to be particularly well performing with respect to the mentioned property of cd/A efficiency and/or lifetime. These compounds are discussed herein to be particularly preferred.

Further an organic optoelectronic device having high efficiency and/or long lifetime may be realized.

Anode

A material for the anode may be a metal or a metal oxide, or an organic material, preferably a material with work function above about 4.8 eV, more preferably above about 5.1 eV, most preferably above about 5.3 eV. Preferred metals are noble metals like Pt, Au or Ag, preferred metal oxides are transparent metal oxides like ITO or IZO which may be advantageously used in bottom-emitting OLEDs having a reflective cathode.

In devices comprising a transparent metal oxide anode or a reflective metal anode, the anode may have a thickness from about 50 nm to about 100 nm, whereas semitransparent metal anodes may be as thin as from about 5 nm to about 15 nm, and non-transparent metal anodes may have a thickness from about 15 nm to about 150 nm.

Hole Injection Layer (HIL)

The hole injection layer may improve interface properties between the anode and an organic material used for the hole transport layer, and is applied on a non-planarized anode and thus may planarize the surface of the anode. For example, the hole injection layer may include a material having a median value of the energy level of its highest occupied molecular orbital (HOMO) between the work function of the anode material and the energy level of the HOMO of the hole transport layer, in order to adjust a difference between the work function of the anode and the energy level of the HOMO of the hole transport layer.

When the hole transport region comprises a hole injection layer 36, the hole injection layer may be formed on the anode by any of a variety of methods, for example, vacuum deposition, spin coating, casting, Langmuir-Blodgett (LB) method, or the like.

When hole injection layer is formed using vacuum deposition, vacuum deposition conditions may vary depending on the material that is used to form the hole injection layer, and the desired structure and thermal properties of the hole injection layer to be formed and for example, vacuum deposition may be performed at a temperature of about 100° C. to about 500° C., a pressure of about $10^{-6}$ Pa to about $10^{-1}$ Pa, and a deposition rate of about 0.1 to about 10 nm/sec, but the deposition conditions are not limited thereto.

When the hole injection layer is formed using spin coating, the coating conditions may vary depending on the material that is used to form the hole injection layer, and the desired structure and thermal properties of the hole injection layer to be formed. For example, the coating rate may be in the range of about 2000 rpm to about 5000 rpm, and a temperature at which heat treatment is performed to remove a solvent after coating may be in a range of about 80° C. to about 200° C., but the coating conditions are not limited thereto.

The hole injection layer may further comprise a p-dopant to improve conductivity and/or hole injection from the anode.

p-Dopant

In another aspect, the p-dopant may be homogeneously dispersed in the hole injection layer.

In another aspect, the p-dopant may be present in the hole injection layer in a higher concentration closer to the anode and in a lower concentration closer to the cathode.

The p-dopant may be one of a quinone derivative or a radialene compound but not limited thereto. Non-limiting examples of the p-dopant are quinone derivatives such as tetracyanoquinonedimethane (TCNQ), 2,3,5,6-tetrafluoro-tetracyano-1,4-benzoquinonedimethane (F4-TCNQ), 4,4', 4"-((1E,1'E,1"E)-cyclopropane-1,2,3-triylidenetris(cyanomethanylylidene))-tris(2,3,5,6-tetrafluorobenzonitrile).

According to another embodiment, the device comprising a triazine compound of formula 1 and/or 1a may further comprise a layer comprising a radialene compound and/or a quinodimethane compound.

In another embodiment, the radialene compound and/or the quinodimethane compound may be substituted with one or more halogen atoms and/or with one or more electron withdrawing groups. Electron withdrawing groups can be selected from nitrile groups, halogenated alkyl groups, alternatively from perhalogenated alkyl groups, alternatively from perfluorinated alkyl groups. Other examples of electron withdrawing groups may be acyl, sulfonyl groups or phosphoryl groups.

Alternatively, acyl groups, sulfonyl groups and/or phosphoryl groups may comprise halogenated and/or perhalogenated hydrocarbyl. In one embodiment, the perhalogenated hydrocarbyl may be a perfluorinated hydrocarbyl. Examples of a perfluorinated hydrocarbyl can be perfluormethyl, perfluorethyl, perfluorpropyl, perfluorisopropyl, perfluorobutyl, perfluorophenyl, perfluorotolyl; examples of sulfonyl groups comprising a halogenated hydrocarbyl may be trifluoromethylsulfonyl, pentafluoroethylsulfonyl, pentafluorophenylsulfonyl, heptafluoropropylsufonyl, nonafluorobutylsulfonyl, and like.

In one embodiment, the radialene and/or the quinodimethane compound may be comprised in a hole injection, hole transporting and/or a hole generation layer.

In one embodiment, the radialene compound may have formula (XX) and/or the quinodimethane compound may have formula (XXIa) or (XXIb):

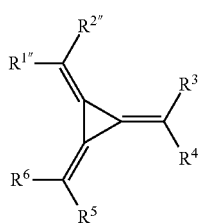

(XX)

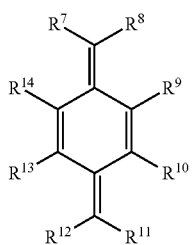

(XXIa)

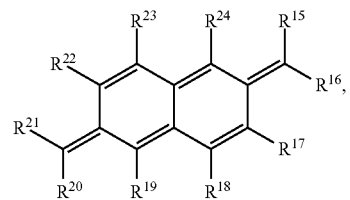

(XXIb)

wherein $R^{1''}$, $R^{2''}$, $R^3$, $R^4$, $R^1$, $R^6$, $R^7$, $R^8$, $R^{11}$, $R^2$, $R^5$, $R^{16}$, $R^{20}$, $R^{21}$ are independently selected from an electron withdrawing groups and $R^9$, $R^{10}$, $R^{13}$, $R^{14}$, $R^{17}$, $R^{18}$, $R^{19}$, $R^{22}$, $R^{23}$ and $R^{24}$ are independently selected from H, halogen and electron withdrawing groups. Electron withdrawing group that can be suitable used are above mentioned.

Hole Transport Layer (HTL)

Conditions for forming the hole transport layer and the electron blocking layer may be defined based on the above-described formation conditions for the hole injection layer.

A thickness of the hole transport part of the charge transport region may be from about 10 nm to about 1000 nm, for example, about 10 nm to about 100 nm. When the hole transport part of the charge transport region comprises the hole injection layer and the hole transport layer, a thickness of the hole injection layer may be from about 10 nm to about 1000 nm, for example about 10 nm to about 100 nm and a thickness of the hole transport layer may be from about 5 nm to about 200 nm, for example about 10 nm to about 150 nm. When the thicknesses of the hole transport part of the charge transport region, the HIL, and the HTL are within these ranges, satisfactory hole transport characteristics may be obtained without a substantial increase in operating voltage.

Hole transport matrix materials used in the hole transport region are not particularly limited. Preferred are covalent compounds comprising a conjugated system of at least 6 delocalized electrons, preferably organic compounds comprising at least one aromatic ring, more preferably organic compounds comprising at least two aromatic rings, even more preferably organic compounds comprising at least three aromatic rings, most preferably organic compounds comprising at least four aromatic rings. Typical examples of hole transport matrix materials which are widely used in hole transport layers are polycyclic aromatic hydrocarbons, triarylene amine compounds and heterocyclic aromatic compounds. Suitable ranges of frontier orbital energy levels of hole transport matrices useful in various layer of the hole transport region are well-known. In terms of the redox potential of the redox couple HTL matrix/cation radical of the HTL matrix, the preferred values (if measured for example by cyclic voltammetry against ferrocene/ferrocenium redox couple as reference) may be in the range 0.0-1.0 V, more preferably in the range 0.2-0.7 V, even more preferably in the range 0.3-0.5 V.

Buffer Layer

The hole transport part of the charge transport region may further include a buffer layer.

Buffer layer that can be suitable used are disclosed in U.S. Pat. Nos. 6,140,763, 6,614,176 and in US2016/248022.

The buffer layer may compensate for an optical resonance distance of light according to a wavelength of the light emitted from the EML, and thus may increase efficiency.

Emission Layer (EML)

The emission layer may be formed on the hole transport region by using vacuum deposition, spin coating, casting, LB method, or the like. When the emission layer is formed using vacuum deposition or spin coating, the conditions for deposition and coating may be similar to those for the formation of the hole injection layer, though the conditions for the deposition and coating may vary depending on the material that is used to form the emission layer. The emission layer may include an emitter host (EML host) and an emitter dopant (further only emitter).

A thickness of the emission layer may be about 100 Å to about 1000 Å, for example about 200 Å to about 600 Å. When the thickness of the emission layer is within these ranges, the emission layer may have improved emission characteristics without a substantial increase in operating voltage.

Emitter Host

According to another embodiment, the emission layer comprises a compound of formula 1 and/or 1a as emitter host.

The emitter host compound has at least three aromatic rings, which are independently selected from carbocyclic rings and heterocyclic rings.

Other compounds that can be used as the emitter host is an anthracene matrix compound represented by formula 400 below:

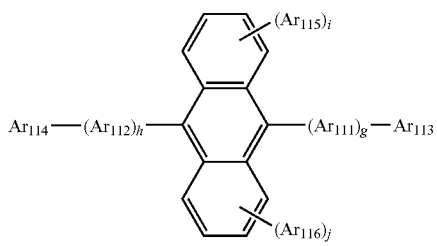

Formula 400

In formula 400, $Ar_{111}$ and $Ar_{112}$ may be each independently a substituted or unsubstituted $C_6$-$C_{60}$ arylene group; $Ar_{113}$ to $Ar_{116}$ may be each independently a substituted or unsubstituted $C_1$-$C_{10}$ alkyl group or a substituted or unsubstituted $C_6$-$C_{60}$ arylene group; and g, h, i, and j may be each independently an integer from 0 to 4.

In some embodiments, $Ar_{111}$ and $Ar_{112}$ in formula 400 may be each independently one of a phenylene group, a naphthalene group, a phenanthrenylene group, or a pyrenylene group; or a phenylene group, a naphthalene group, a phenanthrenylene group, a fluorenyl group, or a pyrenylene group, each substituted with at least one of a phenyl group, a naphthyl group, or an anthryl group.

In formula 400, g, h, i, and j may be each independently an integer of 0, 1, or 2.

In formula 400, $Ar_{113}$ to $Ar_{116}$ may be each independently one of

- a $C_1$-$C_{10}$ alkyl group substituted with at least one of a phenyl group, a naphthyl group, or an anthryl group;
- a phenyl group, a naphthyl group, an anthryl group, a pyrenyl group, a phenanthrenyl group, or a fluorenyl group;
- a phenyl group, a naphthyl group, an anthryl group, a pyrenyl group, a phenanthrenyl group, or a fluorenyl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a pyrenyl group, a phenanthrenyl group, or a fluorenyl group

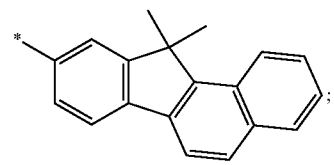 [SMILES: *c1ccc2c(c1)C(C)(C)c1c-2ccc2ccccc12]

or formulas 7 or 8

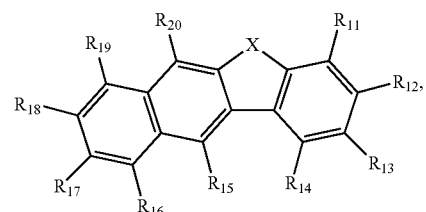

(7)

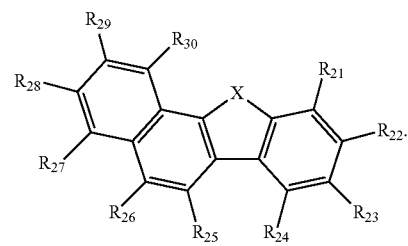

(8)

Wherein in the formulas 7 and 8, X is selected form an oxygen atom and a sulfur atom, but embodiments of the invention are not limited thereto.

In the formula 7, any one of $R_{11}$ to $R_{14}$ is used for bonding to $Ar_{111}$. $R_{11}$ to $R_{14}$ that are not used for bonding to $Ar_{111}$ and $R_{15}$ to $R_{20}$ are the same as $R_1$ to $R_8$.

In the formula 8, any one of $R_{21}$ to $R_{24}$ is used for bonding to $Ar_{111}$. $R_{21}$ to $R_{24}$ that are not used for bonding to $Ar_{111}$ and $R_{25}$ to $R_{30}$ are the same as $R_1$ to $R_8$.

Preferably, the EML host comprises between one and three heteroatoms selected from the group consisting of N, O or S. More preferred the EML host comprises one heteroatom selected from S or O.

Emitter Dopant

The dopant is mixed in a small amount to cause light emission, and may be generally a material such as a metal complex that emits light by multiple excitation into a triplet or more. The dopant may be, for example an inorganic, organic, or organic/inorganic compound, and one or more kinds thereof may be used.

The emitter may be a red, green, or blue emitter.

The dopant may be a fluorescent dopant, for example ter-fluorene, the structures are shown below. 4.4'-bis(4-diphenyl amiostyryl)biphenyl (DPAVBI, 2,5,8,11-tetra-tert-butyl perylene (TBPe), and Compound 8 below are examples of fluorescent blue dopants.

Compound 8

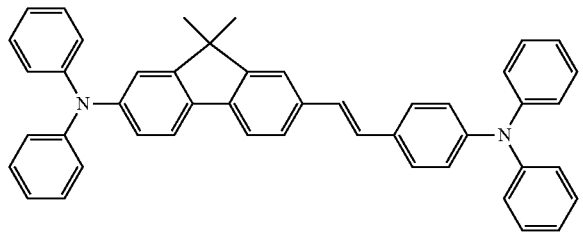

The dopant may be a phosphorescent dopant, and examples of the phosphorescent dopant may be an organic metal compound comprising Ir, Pt, Os, Ti, Zr, Hf, Eu, Tb, Tm, Fe, Co, Ni, Ru, Rh, Pd, or a combination thereof. The phosphorescent dopant may be, for example a compound represented by formula Z, but is not limited thereto:

$J_2MX$ (Z).

In formula Z, M is a metal, and J and X are the same or different, and are a ligand to form a complex compound with M.

The M may be, for example Ir, Pt, Os, Ti, Zr, Hf, Eu, Tb, Tm, Fe, Co, Ni, Ru, Rh, Pd or a combination thereof, and the J and X may be, for example a bidendate ligand.

One or more emission layers may be arranged between the anode and the cathode. To increase overall performance, two or more emission layers may be present.

Charge Generation Layer

A charge generation layer (also named CGL) may be arranged between the first and the second emission layer, and second and third emission layer, if present. Typically, the CGL comprises a n-type charge generation layer (also named n-CGL or electron generation layer) and a p-type charge generation layer (also named p-CGL or hole generation layer). An interlayer may be arranged between the n-type CGL and the p-type CGL.

In one aspect, the n-type CGL may comprise a triazine compound of formula 1 and/or 1a. The n-type CGL further comprises a metal, metal salt or organic metal complex, preferably a metal. The metal may be selected from an alkali, alkaline earth or rare earth metal.

The p-type CGL may comprise a dipyrazino[2,3-f:2',3'-h]quinoxaline, a quinone compound or a radialene compound, preferably dipyrazino[2,3-f:2',3'-h]quinoxaline-2,3,6,7,10,11-hexacarbonitrile or a compound or formula (XX) and/or a compound of formula (XXIa) or (XXIb).

In another aspect, the n-type and p-type CGL are in direct contact.

Electron Transport Layer (ETL)

According to another embodiment, the organic semiconductor layer that comprises a triazine compound of formula 1 and/or 1a is an electron transport layer. In another embodiment the electron transport layer may consist of triazine compound of formula 1 and/or 1a.

For example, an organic light emitting diode according to an embodiment of the present invention comprises at least one electron transport layer, and in this case, the electron transport layer comprises triazine compound of formula 1 and/or 1a, or preferably of at least one compound of formulae D1 to D30.

In another embodiment, the organic electronic device comprises an electron transport region of a stack of organic layers formed by two or more electron transport layers, wherein at least one electron transport layer comprises a triazine compound of formula 1 and/or 1a.

The electron transport layer may include one or two or more different electron transport compounds.

According to another embodiment, a second electron transport layer comprises at least one compound of formula 1 and/or 1a according to the invention and a first electron transport layer comprises a matrix compound, which is selected different to the triazine compound of formula 1 and/or 1a according to the invention, and may be selected from:

an anthracene based compound or a hetero substituted anthracene based compound, preferably 2-(4-(9,10-di(naphthalen-2-yl)anthracene-2-yl)phenyl)-1-phenyl-1H-benzo[d]imidazole and/or N4,N4"-di(naphthalen-1-yl)-N4,N4"-diphenyl-[1,1':4',1"-terphenyl]-4,4"-diamine.

According to another embodiment, a first electron transport layer comprises at least one compound of formula 1 and/or 1a according to the invention and a second electron transport layer comprises a matrix compound, which is selected different to the triazine compound of formula 1 and/or 1a according to the invention, and may be selected from:

a phosphine oxide based compound, preferably (3-(dibenzo[c,h]acridin-7-yl)phenyl)diphenylphosphine oxide and/or phenyl bis(3-(pyren-1-yl)phenyl)phosphine oxide and/or 3-Phenyl-3H-benzo[b]dinaphtho[2,1-d:1',2'-f]phosphepine-3-oxide; or a substituted phenanthroline compound, preferably 2,4,7,9-tetraphenyl-1,10-phenanthroline or 2,9-di(biphenyl-4-yl)-4,7-diphenyl-1,10-phenanthroline.

According to another embodiment a first electron transport layer comprises at least one compound of formula 1 and/or 1a according to the invention and a second electron transport layer comprises a matrix compound, which is selected different to the triazine compound of formula 1 and/or 1a according to the invention, and may be selected from a phosphine oxide based compound, preferably (3-(dibenzo[c,h]acridin-7-yl)phenyl)diphenylphosphine oxide and/or phenyl bis(3-(pyren-1-yl)phenyl)phosphine oxide and/or 3-Phenyl-3H-benzo[b]dinaphtho[2,1-d:1',2'-f]phosphepine-3-oxide.

According to another embodiment, a first and a second electron transport layers comprise triazine compound of formula 1 and/or 1a, wherein the triazine compound of formula 1 and/or 1a is not selected the same.

The thickness of the first electron transport layer may be from about 0.5 nm to about 100 nm, for example about 2 nm to about 40 nm. When the thickness of the first electron transport layer is within these ranges, the first electron transport layer may have improved electron transport ability without a substantial increase in operating voltage.

A thickness of an optional second electron transport layer may be about 1 nm to about 100 nm, for example about 2 nm to about 20 nm. When the thickness of the electron transport layer is within these ranges, the electron transport layer may have satisfactory electron transporting ability without a substantial increase in operating voltage.

The organic semiconductor layer may further comprise at least one second component. The at least one second component may be a metal, metal salt, a metal complex, or at least one second matrix material. The metal may be selected from alkali, alkali earth or transition metal, and the transition metal may be selected from rare earth metals. The metal salt may be selected from the salt of an alkali metal, the salt of an alkaline earth metal or the salt of a rare earth metal. The alkali metal salt may be selected from the group comprising LiF, LiCl, LiBr or LiI, and preferably LiF. The metal complex may be an organic alkali metal complex, preferably alkali metal complex, more preferably LiQ or alkali borate and is essentially non-emissive The electron transport layer may further preferably comprise a monovalent or divalent metal halide or an organic monovalent or divalent metal complex, preferably an alkali halide and/or alkali organic complex.

According to another embodiment, the first and second electron transport layers comprise triazine compound of formula 1 and/or 1a, wherein the second electron transport layer further comprises an alkali halide and/or alkali organic complex.

Alkali Halide

Alkali halides, also known as alkali metal halides, are the family of inorganic compounds with the chemical formula MX, where M is an alkali metal and X is a halogen.

M can be selected from Li, Na, Potassium, Rubidium and Cesium.

X can be selected from F, Cl, Br and J.

According to various embodiments of the present invention a lithium halide may be preferred. The lithium halide can be selected from the group comprising LiF, LiCl, LiBr and LiJ. However, most preferred is LiF.

The alkali halide is essentially non-emissive or non-emissive.

Alkali Organic Complex

The alkali organic complex comprises an alkali metal and at least one organic ligand. The alkali metal is preferably selected from lithium.

According to various embodiments of the present invention the organic ligand of the lithium organic complex is a quinolate, a borate, a phenolate, a pyridinolate or a Schiff base ligand;

preferably the lithium quinolate complex has the formula III, IV or V:

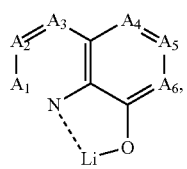

(III)

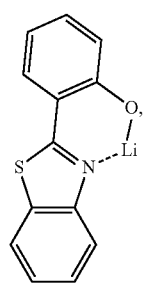

(IV)

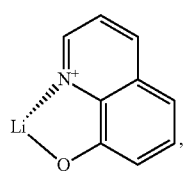

(V)

wherein
A$_1$ to A$_6$ are same or independently selected from CH, CR, N and 0;
R is same or independently selected from hydrogen, halogen, alkyl or arylene or heteroarylene with 1 to 20 carbon atoms; and more preferred A1 to A6 are CH;
preferably the borate based organic ligand is a tetra(1H-pyrazol-1-yl)borate;
preferably the phenolate is a 2-(pyridin-2-yl)phenolate, a 2-(diphenylphosphoryl)phenolate, an imidazol phenolates, or 2-(pyridin-2-yl)phenolate and more preferred 2-(1-phenyl-1H-benzo[d]imidazol-2-yl)phenolate;
preferably the pyridinolate is a 2-(diphenylphosphoryl) pyridin-3-olate.

According to various embodiments of the present invention the organic ligand of the alkali organic complex, preferably of a lithium organic complex, can be a quinolate. Quinolates that can be suitable used are disclosed in WO 2013079217 A1 and incorporated by reference.

According to various embodiments of the present invention the organic ligand of the lithium organic complex can be a borate based organic ligand, Preferably the lithium organic complex is a lithium tetra(1H-pyrazol-1-yl)borate. Borate based organic ligands that can be suitable used are disclosed in WO 2013079676 A1 and incorporated by reference.

According to various embodiments of the present invention the organic ligand of the lithium organic complex can be a phenolate ligand, Preferably the lithium organic complex is a lithium 2-(diphenylphosphoryl)phenolate. Phenolate ligands that can be suitable used are disclosed in WO 2013079678 A1 and incorporated by reference.

Further, phenolate ligands can be selected from the group of pyridinolate, preferably 2-(diphenylphosphoryl)pyridin-3-olate. Pyridine phenolate ligands that can be suitable used are disclosed in JP 2008195623 and incorporated by reference.

In addition, phenolate ligands can be selected from the group of imidazol phenolates, preferably 2-(1-phenyl-1H-benzo[d]imidazol-2-yl)phenolate. Imidazol phenolate ligands that can be suitable used are disclosed in JP 2001291593 and incorporated by reference.

Also, phenolate ligands can be selected from the group of oxazol phenolates, preferably 2-(benzo[d]oxazol-2-yl)phenolate. Oxazol phenolate ligands that can be suitable used are disclosed in US 20030165711 and incorporated by reference.

The alkali organic complex may be essentially non-emissive.

Electron Injection Layer (EIL)

According to another aspect of the invention, the organic electroluminescent device may further comprise an electron injection layer between the electron transport layer (first-ETL) and the cathode.

The electron injection layer (EIL) may facilitate injection of electrons from the cathode.

According to another aspect of the invention, the electron injection layer comprises:
(i) an electropositive metal selected from alkali metals, alkaline earth metals and rare earth metals in substantially elemental form, preferably selected from Li, Na, K, Rb, Cs, Mg, Ca, Sr, Ba, Eu and Yb, more preferably from Li, Na, Mg, Ca, Sr and Yb, even more preferably from Li and Yb, most preferably Yb; and/or
(ii) an alkali metal complex and/or alkali metal salt, preferably the Li complex and/or salt, more preferably a Li quinolinolate, even more preferably a lithium 8-hydroxyquinolinolate, most preferably the alkali metal salt and/or complex of the second electron transport layer (second-ETL) is identical with the alkali metal salt and/or complex of the injection layer.

The electron injection layer may include at least one selected from LiF, NaCl, CsF, $Li_2O$, and BaO.

A thickness of the EIL may be from about 0.1 nm to about 10 nm, or about 0.3 nm to about 9 nm. When the thickness of the electron injection layer is within these ranges, the electron injection layer may have satisfactory electron injection ability without a substantial increase in operating voltage.

The electron injection layer may comprise a triazine compound of formula 1 and/or 1a.

Cathode

A material for the cathode may be a metal, an alloy, or an electrically conductive compound that have a low work function, or a combination thereof. Specific examples of the material for the cathode may be lithium (Li), magnesium (Mg), aluminum (Al), aluminum-lithium (Al—Li), calcium (Ca), magnesium-indium (Mg—In), magnesium-silver (Mg—Ag), silver (Ag) etc. In order to manufacture a top-emission light-emitting device having a reflective anode deposited on a substrate, the cathode may be formed as a light-transmissive electrode from, for example, indium tin oxide (ITO), indium zinc oxide (IZO) or silver (Ag).

In devices comprising a transparent metal oxide cathode or a reflective metal cathode, the cathode may have a thickness from about 50 nm to about 100 nm, whereas semitransparent metal cathodes may be as thin as from about 5 nm to about 15 nm.

Substrate

A substrate may be further disposed under the anode or on the cathode. The substrate may be a substrate that is used in a general organic light emitting diode and may be a glass substrate or a transparent plastic substrate with strong mechanical strength, thermal stability, transparency, surface smoothness, ease of handling, and water resistance.

Hereinafter, the embodiments are illustrated in more detail with reference to examples. However, the present disclosure is not limited to the following examples.

DESCRIPTION OF THE DRAWINGS

These and/or other aspects and advantages of the present invention will become apparent and more readily appreciated from the following description of the exemplary embodiments, taken in conjunction with the accompanying drawings, of which.

Figure 1:
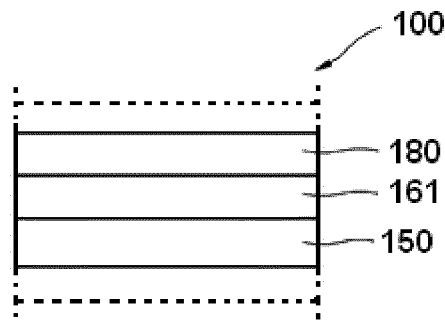
FIG. 1 is a schematic sectional view of an organic light-emitting diode (OLED), according to an exemplary embodiment of the present invention with an emission layer, one electron transport layer and an electron injection layer.

Reference will now be made in detail to the exemplary aspects, examples of which are illustrated in the accompanying drawings, wherein like reference numerals refer to the like elements throughout. The exemplary embodiments are described below, in order to explain the aspects, by referring to the figures.

Herein, when a first element is referred to as being formed or disposed "on" a second element, the first element can be disposed directly on the second element, or one or more other elements may be disposed there between. When a first element is referred to as being formed or disposed "directly on" a second element, no other elements are disposed there between.

The term "contacting sandwiched" refers to an arrangement of three layers whereby the layer in the middle is in direct contact with the two adjacent layers.

The organic light emitting diodes according to an embodiment of the present invention may include a hole transport region; an emission layer; and a first electron transport layer comprising a compound according to formula 1 and/or 1a.

FIG. 1 is a schematic sectional view of an organic light-emitting diode 100, according to an exemplary embodiment of the present invention. The OLED 100 comprises an emission layer 150, an electron transport layer (ETL) 161 comprising triazine compound of formula 1 and/or 1a and an electron injection layer 180, whereby the first electron transport layer 161 is disposed directly on the emission layer 150 and the electron injection layer 180 is disposed directly on the first electron transport layer 161.

Figure 2:
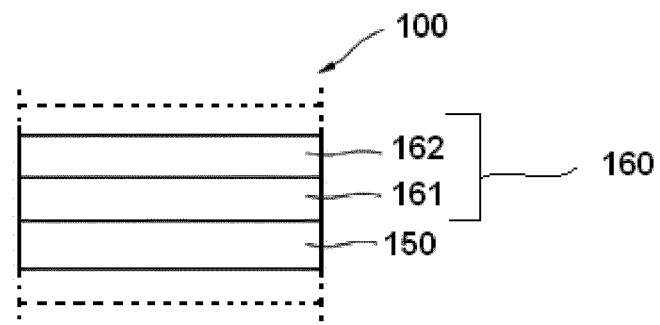
FIG. 2 is a schematic sectional view of an organic light-emitting diode (OLED), according to an exemplary embodiment of the present invention with an emission layer and two electron transport layers.

FIG. 2 is a schematic sectional view of an organic light-emitting diode 100, according to an exemplary embodiment of the present invention. The OLED 100 comprises an emission layer 150 and an electron transport layer stack (ETL) 160 comprising a first electron transport layer 161 comprising triazine compound of formula 1 and/or 1a and a second electron transport layer 162, whereby the second electron transport layer 162 is disposed directly on the first electron transport layer 161. Alternatively, the electron transport layer stack (ETL) 160 comprises a first electron transport layer 161 and a second electron transport layer 162 comprising a triazine compound of formula 1 and/or 1a, whereby the second electron transport layer 162 is disposed directly on the first electron transport layer 161.

Figure 3:
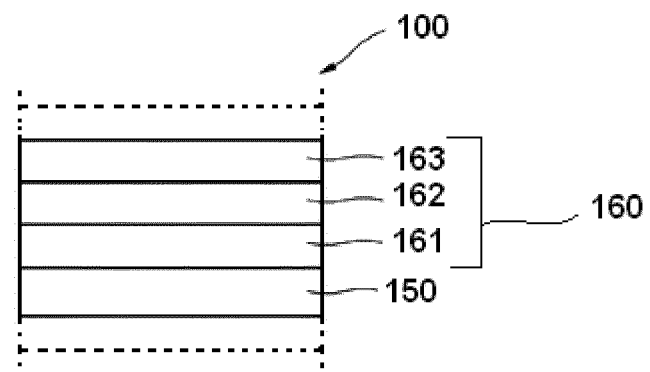
FIG. 3 is a schematic sectional view of an OLED, according to an exemplary embodiment of the present invention with an emission layer and three electron transport layers.

FIG. 3 is a schematic sectional view of an organic light-emitting diode 100, according to an exemplary embodiment of the present invention. The OLED 100 comprises an emission layer 150 and an electron transport layer stack (ETL) 160 comprising a first electron transport layer 161 that comprises triazine compound of formula 1 and/or 1a, a second electron transport layer 162 that comprises triazine compound of formula 1 and/or 1a but different to the triazine compound of the first electron transport layer, and a third electron transport layer 163, whereby the second electron transport layer 162 is disposed directly on the first electron transport layer 161 and the third electron transport layer 163 is disposed directly on the first electron transport layer 162.

Figure 4:
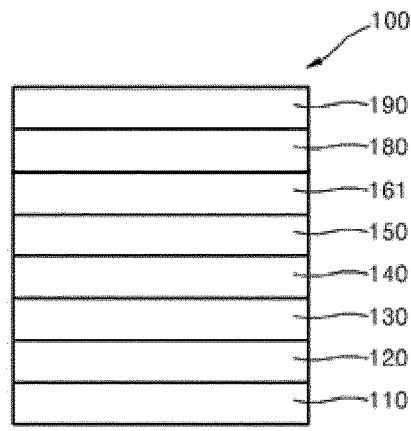
FIG. 4 is a schematic sectional view of an organic light-emitting diode (OLED), according to an exemplary embodiment of the present invention with an emission layer and one electron transport layer.

FIG. 4 is a schematic sectional view of an organic light-emitting diode 100, according to an exemplary embodiment of the present invention. The OLED 100 comprises a substrate 110, a first anode electrode 120, a hole injection layer (HIL) 130, a hole transport layer (HTL) 140, an emission layer (EML) 150, one first electron transport layer (ETL) 161, an electron injection layer (EIL) 180, and a cathode electrode 190. The first electron transport layer (ETL) 161 comprises triazine compound of formula 1 and/or 1a and optionally an alkali halide or alkali organic complex. The electron transport layer (ETL) 161 is formed directly on the EML 150.

Figure 5:
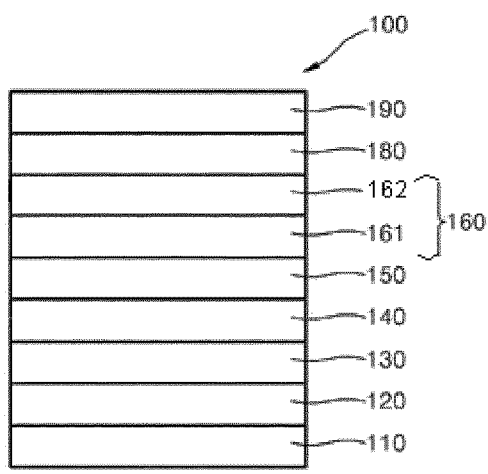
FIG. 5 is a schematic sectional view of an organic light-emitting diode (OLED), according to an exemplary embodiment of the present invention with an emission layer and two electron transport layers.

FIG. 5 is a schematic sectional view of an organic light-emitting diode 100, according to an exemplary embodiment of the present invention. The OLED 100 comprises a substrate 110, a first anode electrode 120, a hole injection layer (HIL) 130, a hole transport layer (HTL) 140, an emission layer (EML) 150, an electron transport layer stack (ETL) 160, an electron injection layer (EIL) 180, and a cathode electrode 190. The electron transport layer (ETL) 160 comprises a first electron transport layer 161 and a second electron transport layer 162, wherein the first electron transport layer is arranged near to the anode (120) and the second electron transport layer is arranged near to the cathode (190). The first and/or the second electron transport layer comprise triazine compound of formula 1 and/or 1a and optionally an alkali halide or alkali organic complex.

Figure 6:
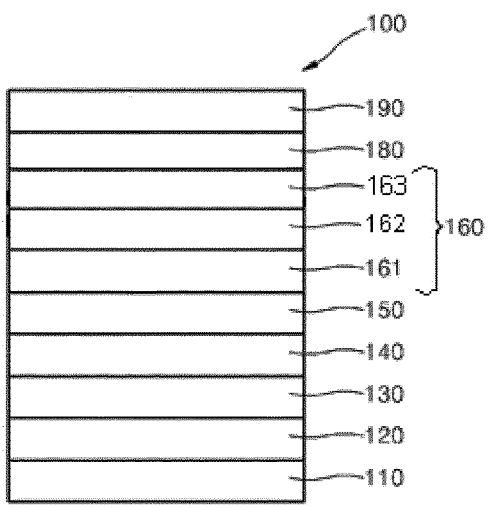
FIG. 6 is a schematic sectional view of an OLED, according to an exemplary embodiment of the present invention with an emission layer and three electron transport layers.

FIG. 6 is a schematic sectional view of an organic light-emitting diode 100, according to an exemplary embodiment of the present invention. The OLED 100 comprises a substrate 110, a first anode electrode 120, a hole injection layer (HIL) 130, a hole transport layer (HTL) 140, an emission layer (EML) 150, an electron transport layer stack (ETL) 160, an electron injection layer (EIL) 180, and a second cathode electrode 190. The electron transport layer stack (ETL) 160 comprises a first electron transport layer 161, a second electron transport layer 162 and a third electron transport layer 163. The first electron transport layer 161 is formed directly on the emission layer (EML) 150. The first, second and/or third electron transport layer comprise triazine compound of formula 1 and/or 1a that is different for each layer, and optionally an alkali halide or alkali organic complex.

Organic Semiconductor Layer

According to another aspect an organic semiconductor layer may comprises at least one triazine compound of formula 1 and/or formula 1a.

According to one embodiment the organic semiconductor layer may comprises at least one triazine compound of formula 1 and/or 1a and further comprises a metal, metal salt or organic alkali metal complex, preferably alkali metal complex, more preferably LiQ or alkali borate.

According to one embodiment the organic semiconductor layer may comprises at least one triazine compound of formula 1 and/or 1a and further comprises a metal, metal salt or organic metal complex, preferably an organic monovalent or divalent metal complex, more preferably LiQ or alkali borate.

According to one embodiment the organic semiconductor layer may comprises at least one triazine compound of formula 1 and/or 1a and LiQ.

According to one embodiment the organic semiconductor layer may comprises at least one triazine compound of formula 1 and/or 1a and alkali borate.

According to one embodiment, wherein at least one organic semiconductor layer is arranged between the emission layer and the cathode, preferably between the auxiliary electron transport layer and the cathode.

In another embodiment, the organic semiconductor layer is arranged between the emission layer and the electron transport layer.

According to one embodiment, the organic semiconductor layer is arranged between the first and second emission layer. The organic semiconductor layer can be an electron transport layer, an emission layer, a hole blocking layer, a charge generation layer and/or an electron injection layer, preferably an electron transport layer or a charge generation layer, and more preferred an electron transport layer.

According to one embodiment, the organic semiconductor layer can be arranged between a photoactive layer and a cathode layer, preferably between an emission layer or light-absorbing layer and the cathode layer, preferably the organic semiconductor layer is an electron transport layer.

According to one embodiment, the organic semiconductor layer may comprise at least one alkali halide or alkali organic complex.

An organic semiconductor layer comprises a triazine compound according to formula 1 and/or 1a or 1a is essentially non-emissive or non-emitting.

Organic Electronic Device

An organic electronic device according to the invention comprises at least one organic semiconductor layer, wherein at least one organic semiconductor layer comprises a triazine compound according to formula 1 and/or 1a.

An organic electronic device according to one embodiment, which comprises at least one organic semiconductor layer that comprises a triazine compound according to formula 1 and/or 1a, wherein this layer is essentially non-emissive or non-emitting.

According to one embodiment, the organic electronic device may comprises at least one organic semiconductor layer comprising triazine compound of formula 1 and/or 1a that is an electron transport layer, an emission layer, a hole blocking layer, a charge generation layer and/or an electron injection layer, preferably an electron transport layer or a charge generation layer, more preferred an electron transport layer.

An organic electronic device according to one embodiment may include a substrate, an anode layer, an organic semiconductor layer comprising triazine compound of formula 1 and/or 1a, and a cathode layer.

The organic electronic device according to according to one embodiment may comprises at least one organic semiconductor layer, wherein the organic semiconductor layer comprising triazine compound of formula 1 and/or 1a is arranged between a photoactive layer and a cathode layer, preferably between an emission layer or light-absorbing layer and the cathode layer, preferably the organic semiconductor layer is an electron transport layer The organic electronic device according to according to one embodiment may comprises at least one organic semiconductor layer comprising triazine compound of formula 1 and/or 1a, wherein the at least one organic semiconductor layer further comprises at least one alkali halide or alkali organic complex.

An organic electronic device according to one embodiment comprises at least one organic semiconductor layer comprising at least one triazine compound of formula 1 and/or 1a, at least one anode layer, at least one cathode layer and at least one emission layer, wherein the organic semiconductor layer comprising at least one triazine compound of formula 1 and/or 1a is preferably arranged between the emission layer and the cathode layer.

An organic electronic device according to one embodiment comprises at least one organic semiconductor layer comprising at least one triazine compound of formula 1 and/or 1a and further comprises at least one alkali halide or alkali organic complex.

An organic electronic device according to one embodiment comprises at least one organic semiconductor layer, at least one anode layer, at least one cathode layer and at least one emission layer, wherein the organic semiconductor layer comprising at least one triazine compound of formula 1 and/or 1a is preferably arranged between the emission layer and the cathode layer. Preferably the at least one organic semiconductor layer is an electron transport layer.

An organic light-emitting diode (OLED) according to the invention may include an anode, a hole transport layer (HTL), an emission layer (EML), an electron transport layer (ETL) comprising at least one triazine compound of formula 1 and/or 1a, and a cathode, which are sequentially stacked on a substrate. In this regard, the HTL, the EML, and the ETL are thin films formed from organic compounds.

An organic electronic device according to one embodiment can be a light emitting device, thin film transistor, a battery, a display device or a photovoltaic cell, and preferably a light emitting device. A light emitting device can be an OLED. According to one embodiment the device comprising the organic semiconductor layer may be arranged as follows:
   arranged between a first and a second electrode, or
   in direct contact with the auxiliary ETL, or
   in direct contact with the EML, or
   in direct contact with the ETL, or
   in direct contact with the cathode, or
   between two emission layers.

According to one embodiment the OLED may have the following layer structure, wherein the layers having the following order:
an anode layer, a hole injection layer, optional a first hole transport layer, optional a second hole transport layer, an emission layer, an electron transport layer comprising triazine compound of formula 1 and/or 1a according to the invention, an electron injection layer, and a cathode layer.

According to another aspect of the present invention, there is provided a method of manufacturing an organic electronic device, the method using:
   at least one deposition source, preferably two deposition sources and more preferred at least three deposition sources.
   The methods for deposition that can be suitable comprise:
   deposition via vacuum thermal evaporation;
   deposition via solution processing, preferably the processing is selected from spin-coating, printing, casting; and/or
   slot-die coating.

According to various embodiments of the present invention, there is provided a method using:
   a first deposition source to release the triazine compound of formula 1 and/or 1a according to the invention, and
   a second deposition source to release the alkali halide or alkali organic complex, preferably a lithium halide or lithium organic complex;
the method comprising the steps of forming the electron transport layer stack; whereby for an organic light-emitting diode (OLED):

the first electron transport layer is formed by releasing the triazine compound of formula 1 and/or 1a according to the invention from the first deposition source and the alkali halide or alkali organic complex, preferably a lithium halide or lithium organic complex from the second deposition source.

According to various embodiments of the present invention, the method may further include forming on the anode electrode an emission layer and at least one layer selected from the group consisting of forming a hole injection layer, forming a hole transport layer, or forming a hole blocking layer, between the anode electrode and the first electron transport layer.

According to various embodiments of the present invention, the method may further include the steps for forming an organic light-emitting diode (OLED), wherein
   on a substrate a first anode electrode is formed,
   on the first anode electrode an emission layer is formed,
   on the emission layer an electron transport layer stack is formed, preferably a first electron transport layer is formed on the emission layer and a second electron transport layer is formed on the first electron transport layer and the second electron transport layer comprises a triazine compound of formula 1 and/or 1a,
   and finally a cathode electrode is formed,
   optional a hole injection layer, a hole transport layer, and a hole blocking layer, formed in that order between the first anode electrode and the emission layer,
   optional an electron injection layer is formed between the electron transport layer stack and the cathode electrode.

According to various embodiments of the present invention, the method may further include forming an electron injection layer on a first electron transport layer. However, according to various embodiments of the OLED of the present invention, the OLED may not comprise an electron injection layer.

According to various embodiments, the OLED may have the following layer structure, wherein the layers having the following order:
an anode, first hole transport layer, second hole transport layer, emission layer, optional second electron transport layer, first electron transport layer comprising triazine compound of formula 1 and/or 1a according to the invention, optional a second electron transport layer, optional an electron injection layer, and a cathode.

According to another aspect of the invention, it is provided an electronic device comprising at least one organic light emitting device according to any embodiment described throughout this application, preferably, the electronic device comprises the organic light emitting diode in one of embodiments described throughout this application. More preferably, the electronic device is a display device.

Hereinafter, the embodiments are illustrated in more detail with reference to examples. However, the present disclosure is not limited to the following examples. Reference will now be made in detail to the exemplary aspects.
Preparation of Triazine Compounds of Formula 1 and 1a
   Triazine compounds of formula 1 and 1a may be prepared as described below. General synthesis scheme of triazine compounds of formula 1:

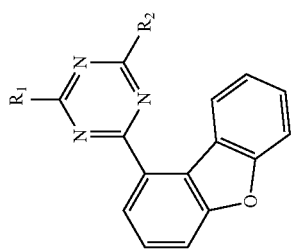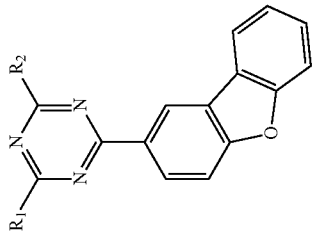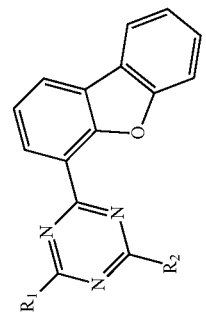
↑ R2-BPin or R2-B(OH)2, K2CO3, Pd(PPh3)4, H2O, THF or dioxane reflux
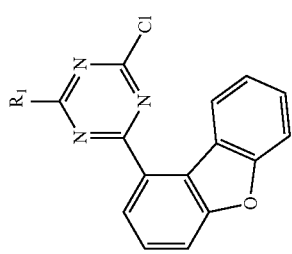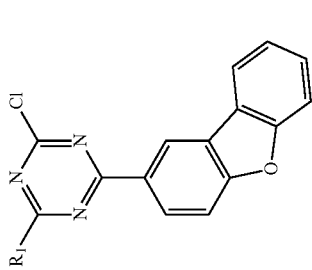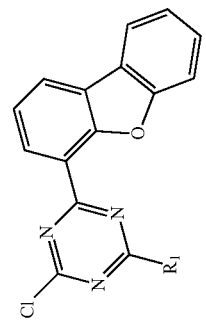
When R1 = Ph CAS: 1883265-3-4 | When R1 = Ph CAS: 1618107-00-8 | When R1 = Ph CAS: 1472729-25-1
↑ R1-BPin or R1-B(OH)2, K2CO3, Pd(PPh3)4, H2O, THF, PhMe reflux
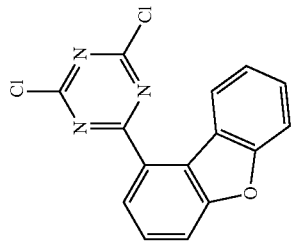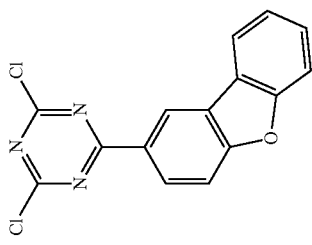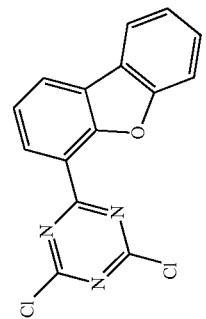
51800-19-2
↑ Following conditions from WO 2015053524 A1

Further Detailed General Synthesis Scheme of Triazine Compounds of Formula 1 and Formula 1a:

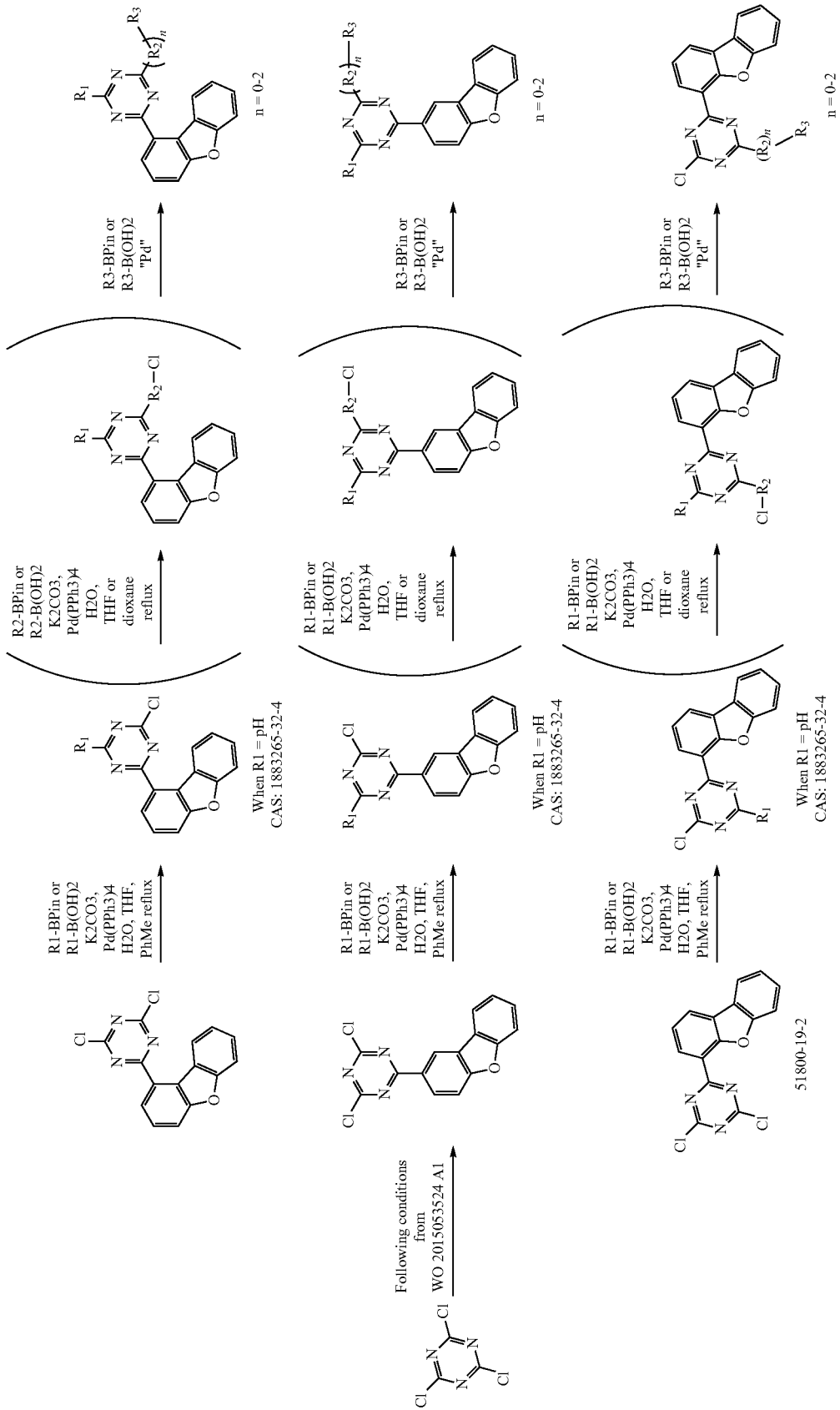

Molecules Synthesized:

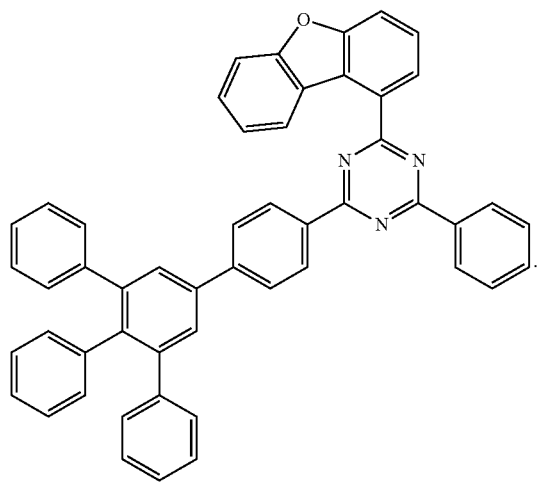

D1

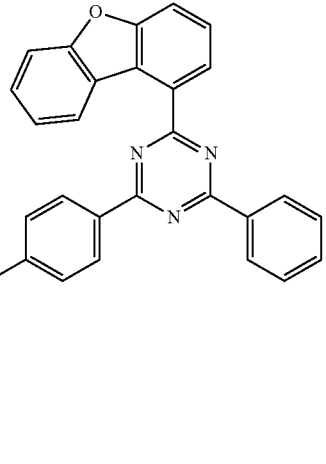

2-(3',5'-diphenyl-[1,1':4',1''-terphenyl]-4-yl)-4,4,5,5-tetramethyl-1,3,2-dioxaborolane

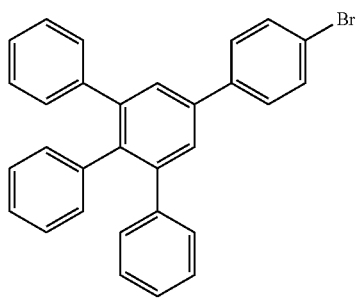

96376-80-6

→

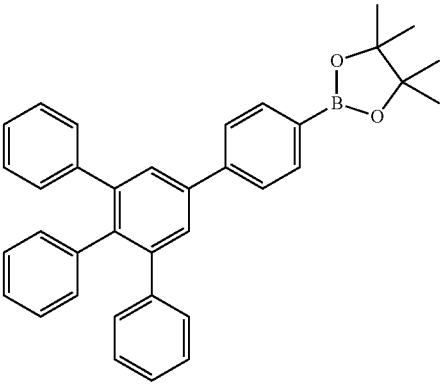 [SMILES: CC1(C)OB(c2ccc(-c3cc(-c4ccccc4)c(-c4ccccc4)c(-c4ccccc4)c3)cc2)OC1(C)C]

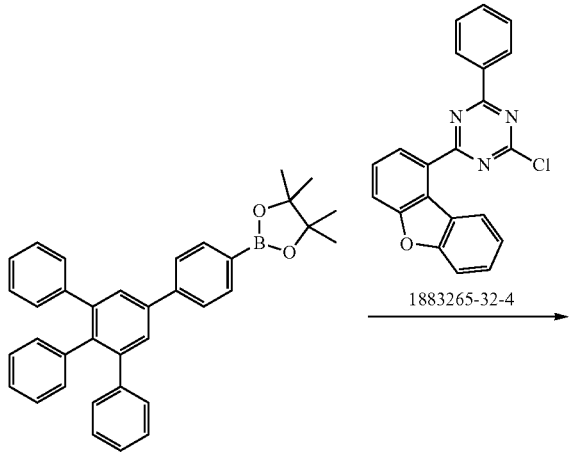

A flask was flushed with nitrogen and charged with 5'-(4-bromophenyl)-3'-phenyl-1,1':2',1''-terphenyl (11.0 g, 23.8 mmol), bis(pinacolato)diboron (6.7 g, 26.2 mmol), Pd(dppf)Cl$_2$ (1.0 g, 1.4 mmol), and potassium acetate (5.8 g, 59.6 mmol). Dry and deaerated DMF (110 mL) was added and the reaction mixture was heated to 80° C. under a nitrogen atmosphere for 22 hours. Subsequently, all volatiles were removed in vacuo, water and dichloromethane were added and the organic phase was washed with water four times. After drying over MgSO$_4$, the organic phase was filtered through a pad of Florisil. After rinsing with additional dichloromethane, the filtrate was concentrated to a minimal amount and precipitation was induced by addition of n-hexane. The precipitate was collected by suction filtration, washed with n-hexane and dried to yield 10.4 g (86%) of an off-white solid.

2-(dibenzo[b,d]furan-1-yl)-4-(3',5'-diphenyl-[1,1':4',1''-terphenyl]-4-yl)-6-phenyl-1,3,5-triazine [Compound D1]

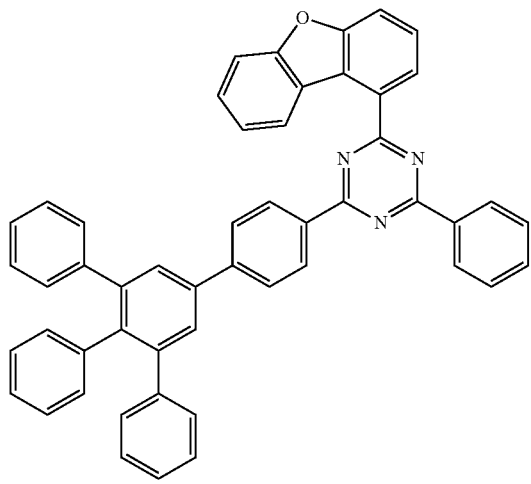 [SMILES: c1ccc(-c2nc(-c3ccc(-c4cc(-c5ccccc5)c(-c5ccccc5)c(-c5ccccc5)c4)cc3)nc(-c3cccc4oc5ccccc5c34)n2)cc1]

A flask was flushed with nitrogen and charged with 2-(3',5'-diphenyl-[1,1':4',1''-terphenyl]-4-yl)-4,4,5,5-tetramethyl-1,3,2-dioxaboro-lane (14.2 g, 28 mmol), 2-chloro-4-(dibenzo[b,d]furan-1-yl)-6-phenyl-1,3,5-triazine (10 g, 28 mmol), Pd(dppf)Cl$_2$ (0.61 g, 0.84 mmol), and K$_2$CO$_3$ (7.7 g, 56 mmol). A mixture of deaerated toluene/THF/water (4:1:1, 170 mL) was added and the reaction mixture was heated to reflux under a nitrogen atmosphere overnight. After cooling down to room temperature, the organic phase was removed and washed with brine and dried over MgSO$_4$. After filtration over a pad of Florisil and rinsing with additional toluene, the filtrate was concentrated to a minimal amount and an excess of n-hexane was added. The formed precipitate was isolated by suction filtration and washed with n-hexane. Further purification was achieved by recrystallization from toluene/cyclohexane 2:1. The obtained solid was filtered off and washed with methanol to afford 16 g (80%) of a white solid after drying. Final purification was achieved by sublimation. m/z=704 ([M+H]+).

The chemical structure, calculated HOMO, LUMO and dipole moment of compounds of formula 1, namely D1 and comparative example 1 simulated by DFT (B3LYP_Gaussian/6-31G*, gas phase) are shown in Table 1.

TABLE 1

| Compound | Structure | Dipole moment [Debye] | HOMO [eV] | LUMO [eV] |
|---|---|---|---|---|
| Comparative-1 | 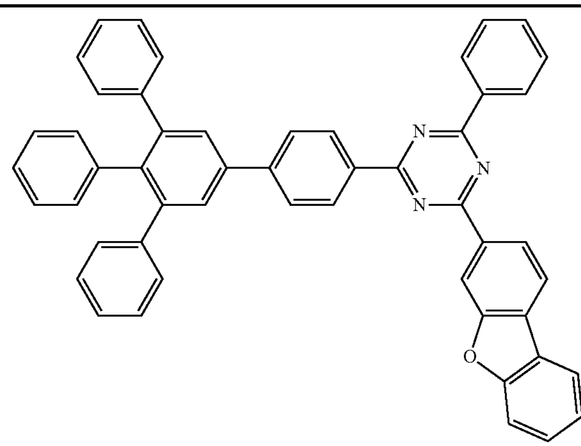 | 1.23 | −6.04 | −1.96 |
| D1 | 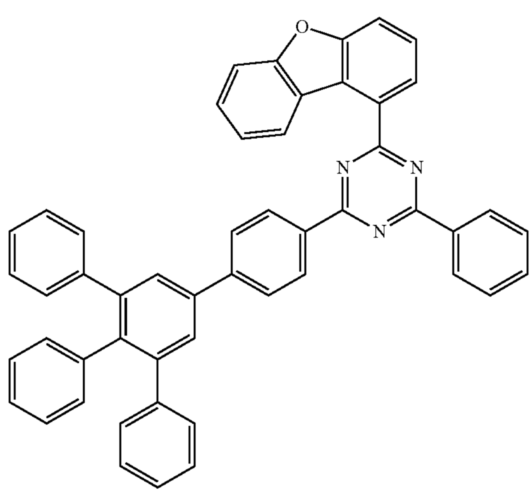 [SMILES: c1ccc(-c2nc(-c3ccc(-c4cc(-c5ccccc5)c(-c5ccccc5)c(-c5ccccc5)c4)cc3)nc(-c3cccc4oc5ccccc5c34)n2)cc1] | 1.71 | −5.84 | −1.96 |

The chemical structure, calculated HOMO, LUMO and dipole moment of compounds of formula 1a, namely D31 to D36 simulated by DFT (B3LYP_Gaussian/6-31G*, gas phase) are shown in Table 1A.

TABLE 1A

| Compound | Structure | HOMO [eV] | LUMO [eV] | Dipole moment [Debye] |
|---|---|---|---|---|
| D31 | 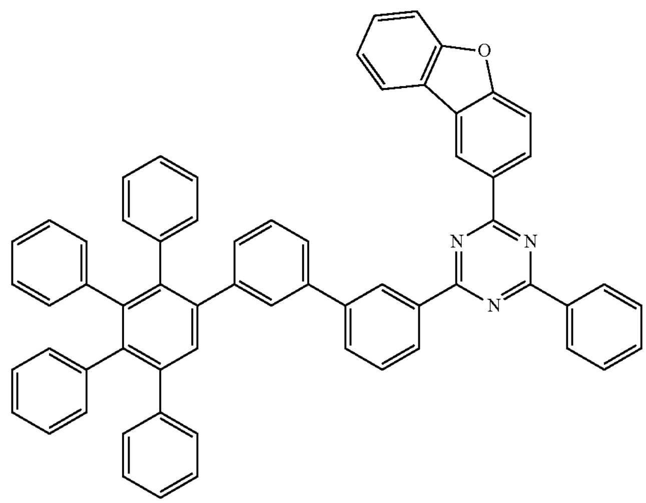 [SMILES: c1ccc(-c2nc(-c3cccc(-c4cccc(-c5cc(-c6ccccc6)c(-c6ccccc6)c(-c6ccccc6)c5-c5ccccc5)c4)c3)nc(-c3ccc4oc5ccccc5c4c3)n2)cc1] | −5.82 | −1.79 | 1.47 |
| D32 | 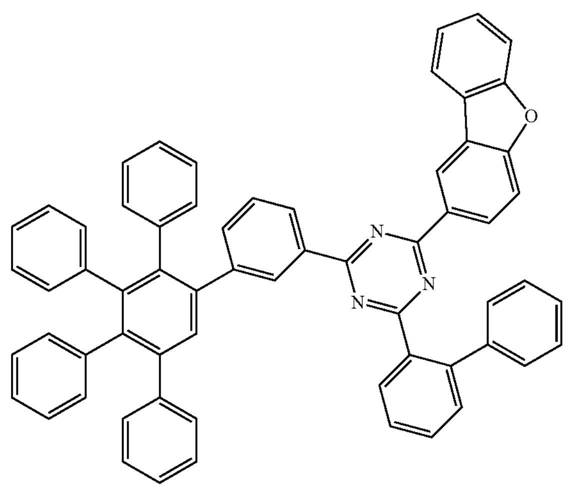 [SMILES: c1ccc(-c2ccccc2-c2nc(-c3cccc(-c4cc(-c5ccccc5)c(-c5ccccc5)c(-c5ccccc5)c4-c4ccccc4)c3)nc(-c3ccc4oc5ccccc5c4c3)n2)cc1] | −5.83 | −1.67 | 0.95 |
| D33 | 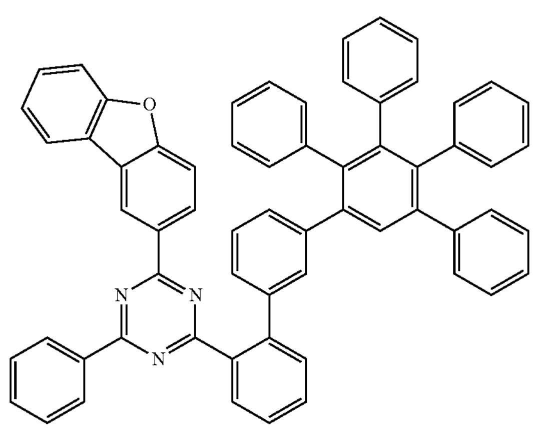 [SMILES: c1ccc(-c2nc(-c3ccc4oc5ccccc5c4c3)nc(-c3ccccc3-c3cccc(-c4cc(-c5ccccc5)c(-c5ccccc5)c(-c5ccccc5)c4-c4ccccc4)c3)n2)cc1] | −5.75 | −1.72 | 1.58 |

TABLE 1A-continued

| Compound | Structure | HOMO [eV] | LUMO [eV] | Dipole moment [Debye] |
|---|---|---|---|---|
| D34 | 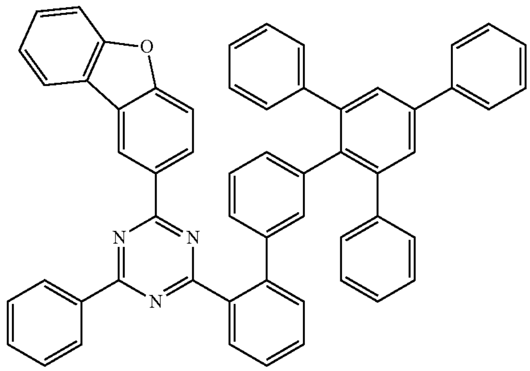 [SMILES: c1ccc(-c2cc(-c3ccccc3)c(-c3cccc(-c4ccccc4-c4nc(-c5ccccc5)nc(-c5ccc6oc7ccccc7c6c5)n4)c3)c(-c3ccccc3)c2)cc1] | −5.70 | −1.78 | 0.79 |
| D35 | 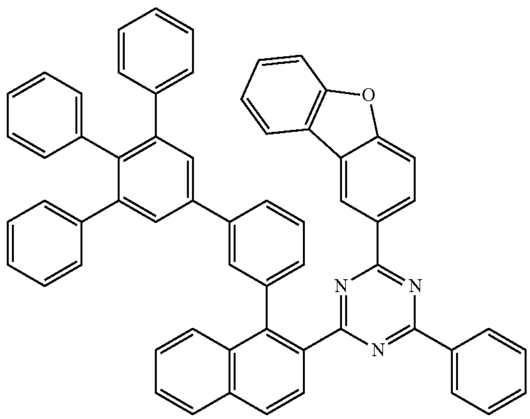 [SMILES: c1ccc(-c2nc(-c3ccc4oc5ccccc5c4c3)nc(-c3ccc4ccccc4c3-c3cccc(-c4cc(-c5ccccc5)c(-c5ccccc5)c(-c5ccccc5)c4)c3)n2)cc1] | −5.77 | −1.75 | 1.09 |
| D36 | 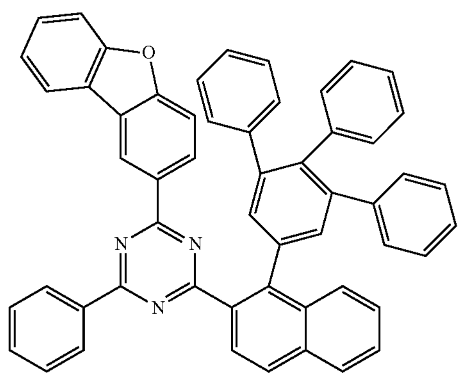 [SMILES: c1ccc(-c2nc(-c3ccc4oc5ccccc5c4c3)nc(-c3ccc4ccccc4c3-c3cc(-c4ccccc4)c(-c4ccccc4)c(-c4ccccc4)c3)n2)cc1] | −5.74 | −1.79 | 0.71 |

General Procedure for Fabrication of OLEDs

For the top emission OLED devices of example-1 and of the comparative example a substrate with dimensions of 150 mm×150 mm×0.7 mm was ultrasonically cleaned with a 2% aquatic solution of Deconex FPD 211 for 7 minutes and then with pure water for 5 minutes, and dried for 15 minutes in a spin rinse dryer. Subsequently, Ag was deposited as anode at a pressure of 10-5 to 10-7 mbar.

Then, HT-1 and HD-1 were vacuum co-deposited on the anode to form a HIL. Then, HT-1 was vacuum deposited on the HIL, to form an HTL. Then, HT-2 was vacuum deposited on the HTL to form an electron blocking layer (EBL).

Afterwards the emission layer was formed on the EBL by co-deposition of HOST-1 and EMITTER-1.

Then, the ET-1 was vacuum deposited onto the emission layer to form the hole blocking layer (HBL). Then, the electron transport layer was formed on the hole blocking layer by co-depositing a compound of formula (I) and LiQ for example-1. For the comparative example the electron transport layer was formed on the hole blocking layer by co-depositing the compound comparative-1 and LiQ.

Then, the electron injection layer is formed on the electron transporting layer by deposing Yb.

Ag:Mg is then evaporated at a rate of 0.01 to 1 Å/s at 10-7 mbar to form a cathode.

A cap layer of HT-1 is formed on the cathode.

The details of the layer stack in the top emission OLED devices are given below. A slash "/" separates individual layers. Layer thicknesses are given in squared brackets [ . . . ], mixing ratios in wt % given in round brackets ( . . . ):

Layer Stack Details:
 Ag [100 nm]/HT-1:HD-1 (92:8) [10 nm]/HT-1 [118 nm]/
HT-2 [5 nm]/H09:BD200 (97:3) [20 nm]/ET-1 [5 nm]/
Compound of formula (I): LiQ (1:1) [31 nm]/Yb [2 nm]/
Ag:Mg (90:10) [13 nm]/HT-1 [70 nm]

List of Compounds Used (See Table 2)

TABLE 2

|  | IUPAC name | Reference |
| --- | --- | --- |
| HT-1 | N-([1,1'-biphenyl]-4-yl)-9,9-dimethyl-N-(4-(9-phenyl-9H-carbazol-3-yl)phenyl)-9H-fluoren-2-amine [CAS 1242056-42-3] | US2016322581 |
| HT-2 | N,N-bis(4-(dibenzo[b,d]furan-4-yl)phenyl)-[1,1':4',1''-terphenyl]-4-amine [CAS 1198399-61-9] | JP2014096418 |
| HD-1 | 4,4',4''-((1E,1'E,1''E)-cyclopropane-1,2,3-triylidenetris(cyanomethanylylidene))tris(2,3,5,6-tetrafluorobenzonitrile) [CAS 1224447-88-4] | US2008265216 |
| HOST-1 | H09 (Fluorescent-blue host material) | Commercially available from Sun Fine Chemicals, Inc, S. Korea |
| EMITTER-1 | BD200 (Fluorescent-blue emitter material) | Commercially available from Sun Fine Chemicals, Inc, S. Korea |
| ET-1 | 2-(3'-(9,9-dimethyl-9H-fluoren-2-yl)-[1,1'-biphenyl]-3-yl)-4,6-diphenyl-1,3,5-triazine [CAS 1955543-57-3] | WO 2016105141 |
| Comparative-1 | 2-(dibenzo[b,d]furan-3-yl)-4-(3',5'-diphenyl-[1,1':4',1''-terphenyl]-4-yl)-6-phenyl-1,3,5-triazine | — |
| LiQ | 8-Hydroxyquinolinolato-lithium [CAS 850918-68-2] | WO2013079217 |

Properties of compound D1 of formula (1) and of comparative compound of Comparative-1, see Table 3.

TABLE 3

| Compound name | Chemical Structure | mp [° C.] | Tg [° C.] | T$_{RO}$ [° C.] |
| --- | --- | --- | --- | --- |
| Comparative-1 | 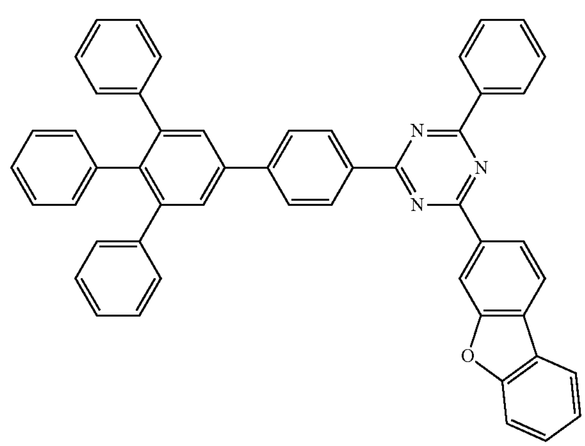 [SMILES: c1ccc(-c2nc(-c3ccc(-c4cc(-c5ccccc5)c(-c5ccccc5)c(-c5ccccc5)c4)cc3)nc(-c3ccc4c(c3)oc3ccccc34)n2)cc1] | 285 | 147 | 272 |

TABLE 3-continued

| Compound name | Chemical Structure | mp [° C.] | Tg [° C.] | $T_{RO}$ [° C.] |
|---|---|---|---|---|
| D1 | 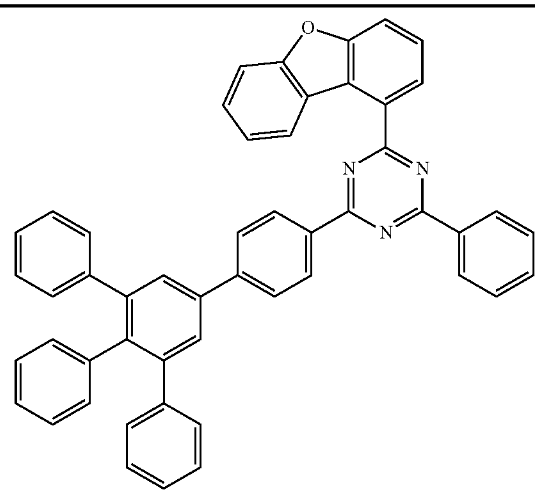 | 216 | 135 | 253 |

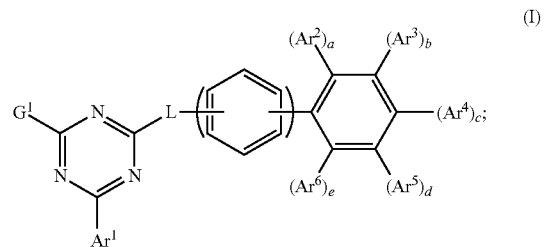

Performance of an organic electroluminescent device comprising the compounds of formula (1) as a matrix material in the electron transport layer, see table 4.

TABLE 4

| OLED device examples | Matrix material | n-additive | Operating voltage at 10 mA/cm² (V) | CEff at 10 mA/cm² (cd/A) | LT97 at 30 mA/cm² (hours) |
|---|---|---|---|---|---|
| Comparative example | Comparative-1 | LiQ | 3.56 | 6.48 | 112 |
| Example-1 | D1 | LiQ | 3.71 | 6.89 | 131 |

Dipole moment, Dipole moment range (max-min), HOMO and LUMO energy levels of compounds D1, D11 and D12, simulated by DFT (B3LYP_Gaussian/6-31G*, gas phase) are shown in table 5.

TABLE 5

| | Dipole moment [Debye] | Dipole moment range max-min [Debye] | HOMO [eV] | LUMO [eV] |
|---|---|---|---|---|
| D1 | 1.68 to 1.71 | 0.03 | −5.84 | −1.96 |
| D11 | 0.58 to 1.52 | 0.94 | −5.82 | −1.90 |
| D12 | 0.75 to 0.85 | 0.10 | −5.80 | −1.90 |

TECHNICAL EFFECT OF THE INVENTION

As can be seen in Table 1 that the HOMO energy level (eV) of the compositions of examples 1 according to formula 1 and/or 1a are lower than of the comparative example 1.

In summary, higher CEff at 10 mA/cm² and improved lifetime as shown in table 4 may be achieved when the organic semiconductor layer comprises a triazine compound of formula 1 and/or 1a of compound D1. High performance may be achieved for a wide range of alkali organic complexes While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

The invention claimed is:

1. A triazine compound according to formula I:

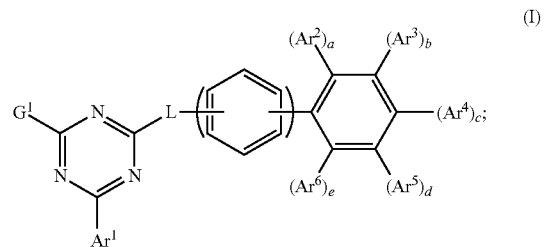

(I)

wherein formula I for L=phenylene and formula I is represented by formula 1:

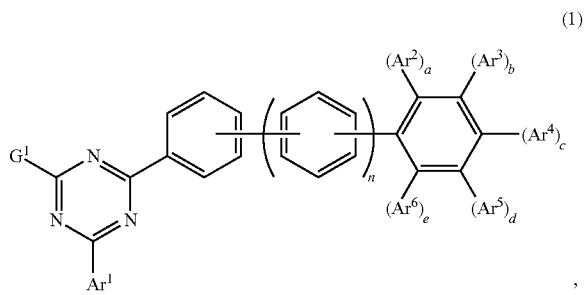

(1)

and wherein formula I for L=naphthylene and formula I is represented by formula 1a:

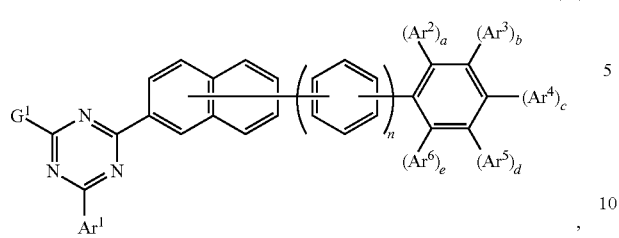
(1a)

wherein
G¹ has the formula 2:

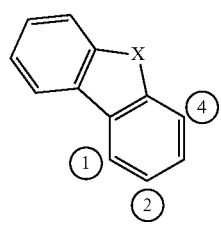
(2)

wherein
G¹ of formula 2 is linked to formula 1 to one position, selected from the positions marked by "①" and "②";
X is O, S or Se;
a, b, c, d, e are selected from 0 or 1, wherein 3≤a+b+c+d+e≤5;
n is selected from 0, 1 or 2,
Ar¹ is selected from H, $C_1$ to $C_{16}$ alkyl, substituted or unsubstituted $C_6$ to $C_{40}$ aryl, substituted or unsubstituted $C_3$ to $C_{40}$ heteroaryl, wherein
the substituents of the substituted $C_6$ to $C_{40}$ aryl and substituted $C_3$ to $C_{40}$ heteroaryl are selected from $C_1$ to $C_{16}$ alkyl, $C_1$ to $C_{16}$ alkoxy, $C_3$ to $C_{16}$ branched alkyl, $C_3$ to $C_{16}$ cyclic alkyl, $C_3$ to $C_{16}$ branched alkoxy, $C_3$ to $C_{16}$ cyclic alkoxy, partially or perfluorinated $C_1$ to $C_{16}$ alkyl, partially or perfluorinated $C_1$ to $C_{16}$ alkoxy, partially or perdeuterated $C_1$ to $C_{16}$ alkyl, partially or perdeuterated $C_1$ to $C_{16}$ alkoxy, $C_6$ to $C_{24}$ aryl, $C_3$ to $C_{25}$ heteroaryl, —PX(R¹)₂, D, F or CN, wherein
R¹ is independently selected from $C_1$ to $C_{16}$ alkyl, $C_1$ to $C_{16}$ alkoxy, partially or perfluorinated $C_1$ to $C_{16}$ alkyl, partially or perfluorinated $C_1$ to $C_{16}$ alkoxy, partially or perdeuterated $C_1$ to $C_{16}$ alkyl, partially or perdeuterated $C_1$ to $C_{16}$ alkoxy, $C_6$ to $C_{18}$ aryl, $C_3$ to $C_{25}$ heteroaryl;
Ar², Ar³, Ar⁴, Ar⁵ and Ar⁶ are independently selected from substituted or unsubstituted $C_6$ to $C_{12}$ aryl or substituted or unsubstituted $C_4$ to $C_{10}$ heteroaryl, wherein
the substituent of the substituted $C_6$ to $C_{12}$ aryl or substituted $C_4$ to $C_{10}$ heteroaryl is selected from $C_1$ to $C_6$ alkyl, $C_1$ to $C_6$ alkoxy, partially or perdeuterated $C_1$ to $C_6$ alkyl, partially or perdeuterated $C_1$ to $C_6$ alkoxy, partially or perfluorinated $C_1$ to $C_6$ alkyl, partially or perfluorinated $C_1$ to $C_6$ alkoxy, D, F, or CN.

2. The triazine compound of formula 1 according to claim 1, wherein X is selected from O or S.

3. The triazine compound of formula 1 according to claim 1, wherein
Ar¹ is selected from $C_1$ to $C_{12}$ alkyl, substituted or unsubstituted $C_6$ to $C_{24}$ aryl or substituted or unsubstituted $C_3$ to $C_{36}$ heteroaryl, wherein
the substituents of the substituted $C_6$ to $C_{24}$ aryl and substituted $C_3$ to $C_{36}$ heteroaryl are selected from $C_1$ to $C_{12}$ alkyl, $C_1$ to $C_{12}$ alkoxy, partially or perfluorinated $C_1$ to $C_{12}$ alkyl, partially or perfluorinated $C_1$ to $C_{16}$ alkoxy, partially or perdeuterated $C_1$ to $C_{12}$ alkyl, partially or perdeuterated $C_1$ to $C_{16}$ alkoxy, $C_6$ to $C_{18}$ aryl, $C_3$ to $C_{25}$ heteroaryl, D, F or CN.

4. The triazine compound of formula 1 according to claim 1, wherein
Ar¹ is selected from unsubstituted $C_6$ to $C_{24}$ aryl.

5. The triazine compound of formula 1 according to claim 1, wherein Ar¹ is independently selected from B1 to B3, B3a, B4 to B77,
wherein
a) B1 to B6 are substituted or unsubstituted non-heteroaryl groups:

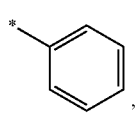
(B1)

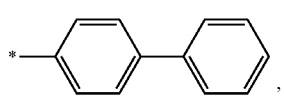
(B2)

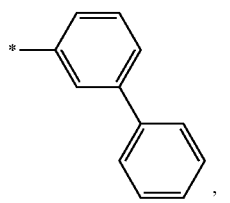
(B3)

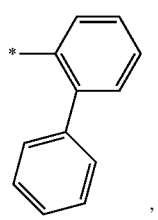
(B3a)

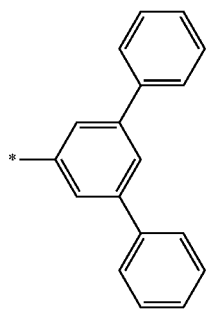
(B4)

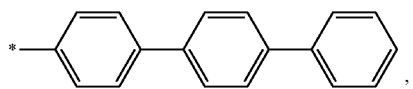
(B5)

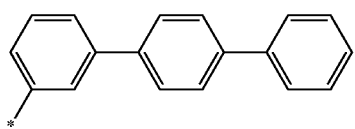
(B6)
or
b) B7 to B23 are substituted or unsubstituted annelated non-heteroaryl groups:
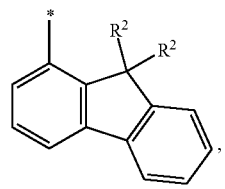
(B7)
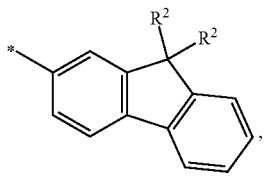
(B8)
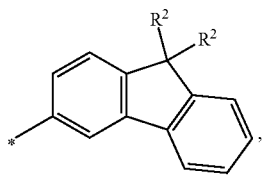
(B9)
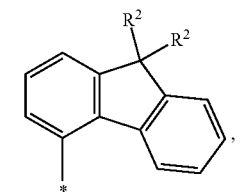
(B10)
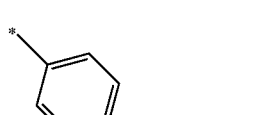
(B11)
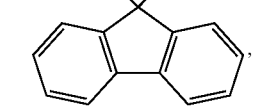
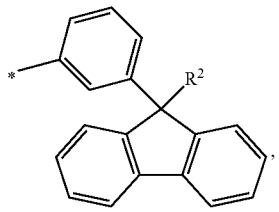
(B12)
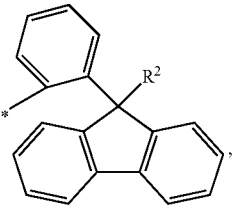
(B13)
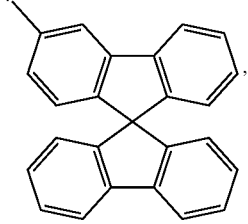
(B14)
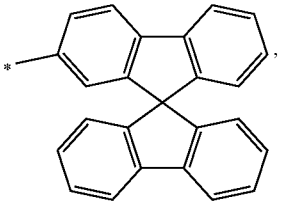
(B15)
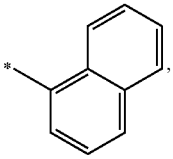
(B16)
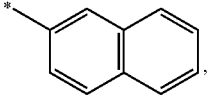
(B17)
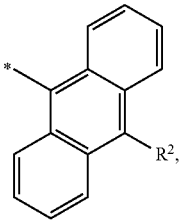
(B18)
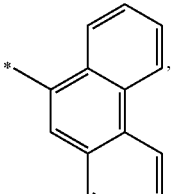
(B19)
(B20)

-continued
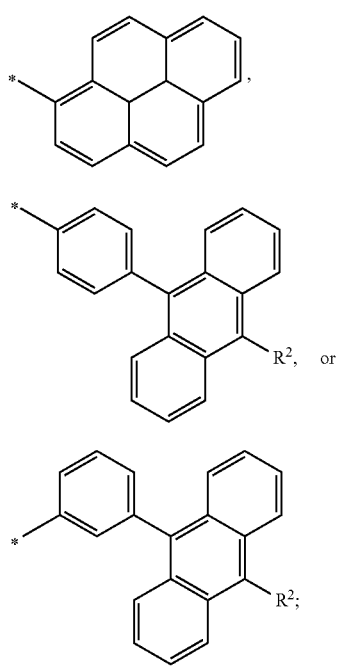
(B21), (B22), (B23)
or
c) B24 to B31 are dibenzofurane/dibenzothiophene group:
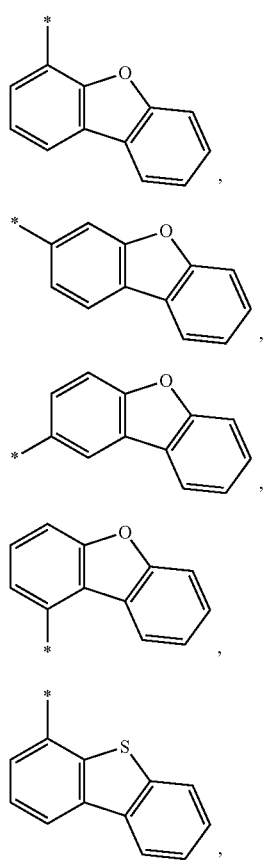
(B24), (B25), (B26), (B27), (B28)
(B29)
(B30)
(B31)
or
d) B32 to B34 are unsubstituted pyridine groups:
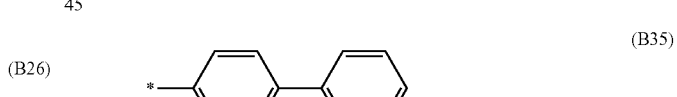
(B32), (B33), (B34)
or
e) B35 to B62 are unsubstituted or substituted hetero arylene groups:
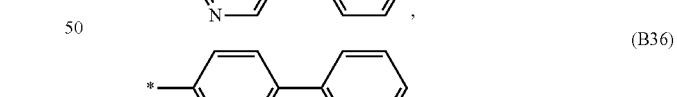
(B35)
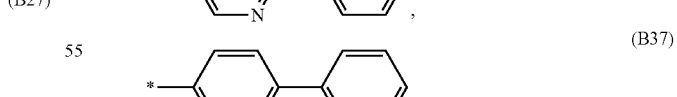
(B36)
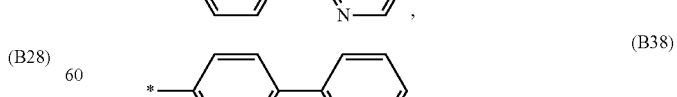
(B37)
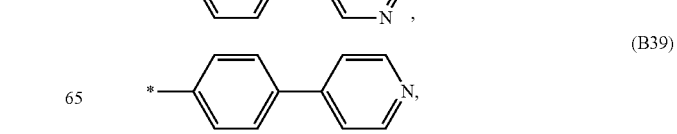
(B38), (B39)

-continued
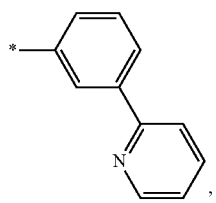 (B40)
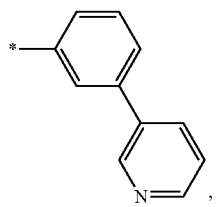 (B41)
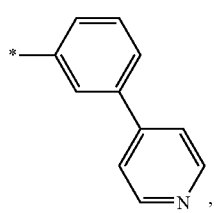 (B42)
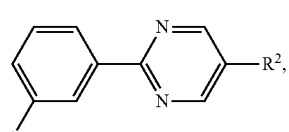 (B43)
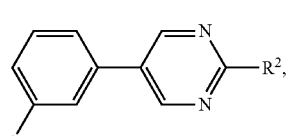 (B44)
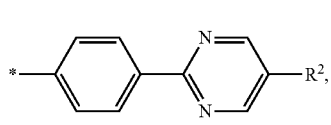 (B45)
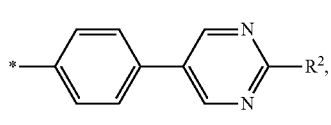 (B46)
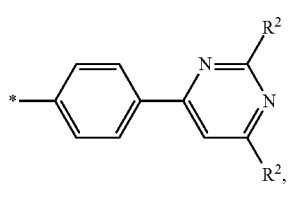 (B47)
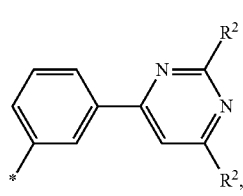 (B48)
-continued
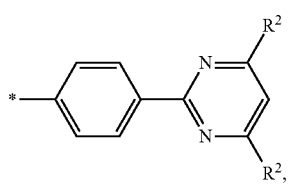 (B49)
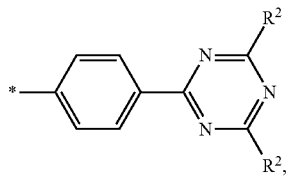 (B50)
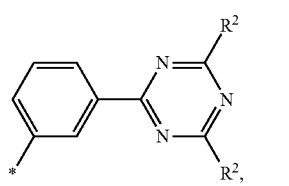 (B51)
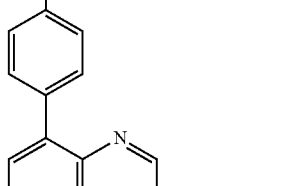 (B52)
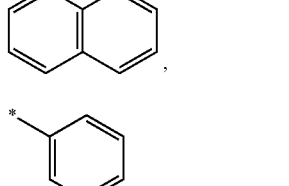 (B53)
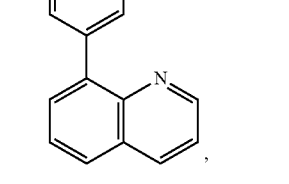 (B54)
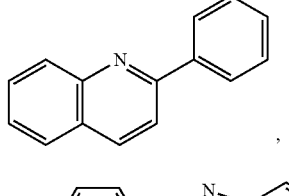 (B55)
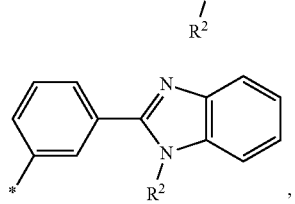 (B56)

-continued
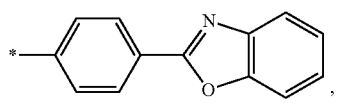
(B57)
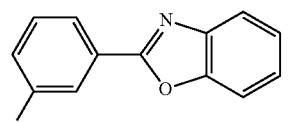
(B58)
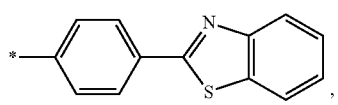
(B59)
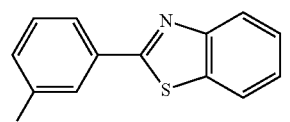
(B60)
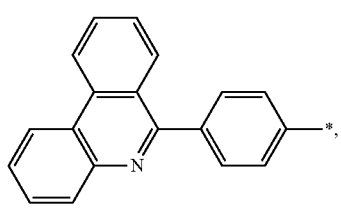
(B61)
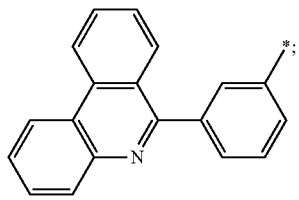
(B62)
or
f) B63 to B65 unsubstituted annelated hetero arylene groups:
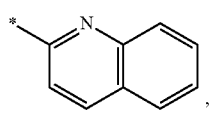
(B63)
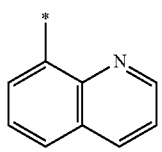
(B64)
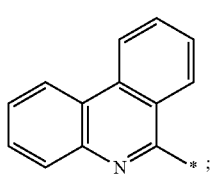
(B65)
or
g) B66 and B67 are nitrile substituted phenyl groups
(B66)
(B67)
or
h) B68 to B70 are nitrile substituted biphenyl groups
(B68)
(B69)
(B70)
or
i) B71 to B77 are carbazole groups
(B71)
(B72)
(B73)

-continued (B74)

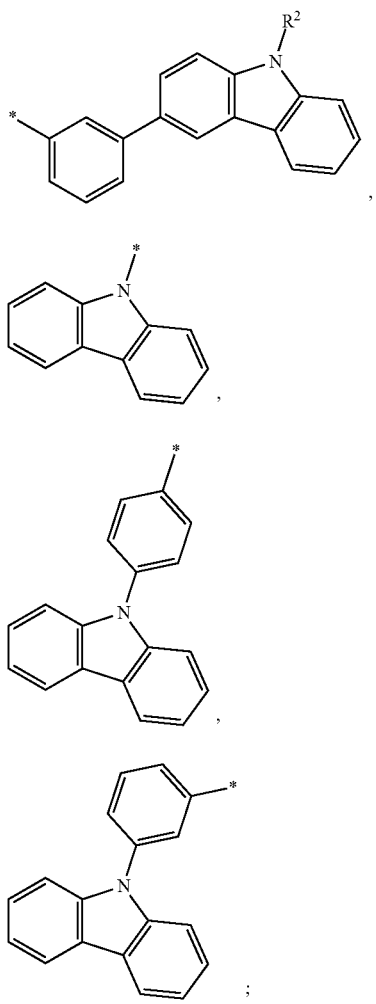

(B75)

(B76)

(B77)

wherein the substituent $R^2$ is independently selected from H, $C_1$ to $C_{16}$ alkyl, partially or perfluorinated $C_1$ to $C_{16}$ alkyl, partially or perdeuterated $C_1$ to $C_{16}$ alkyl, $C_1$ to $C_{16}$ alkoxy, $C_3$ to $C_{16}$ branched alkyl, $C_3$ to $C_{16}$ cyclic alkyl, $C_3$ to $C_{16}$ branched alkoxy, $C_3$ to $C_{16}$ cyclic alkoxy, $C_6$ to $C_{24}$ aryl and $C_3$ to $C_{25}$ heteroaryl.

6. The triazine compound of formula 1 according to claim 1, wherein $Ar^1$ is independently selected from structures C1 to C5:

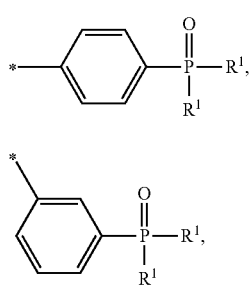

-continued

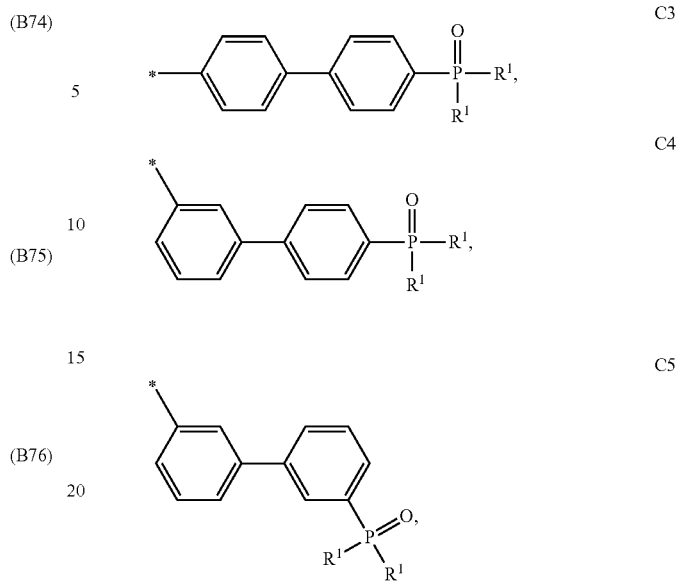

wherein $R^1$ is independently selected from $C_1$ to $C_{16}$ alkyl, $C_1$ to $C_{16}$ alkoxy, partially or perfluorinated $C_1$ to $C_{16}$ alkyl, partially or perfluorinated $C_1$ to $C_{16}$ alkoxy, partially or perdeuterated $C_1$ to $C_{16}$ alkyl, partially or perdeuterated $C_1$ to $C_{16}$ alkoxy, $C_6$ to $C_{18}$ aryl, $C_3$ to $C_{25}$ heteroaryl.

7. The triazine compound of formula 1 according to claim 1, wherein at least one to at most three substituents of $Ar^2$, $Ar^3$, $Ar^5$ and $Ar^6$ are independently selected from unsubstituted $C_6$ to $C_{12}$ aryl or unsubstituted $C_4$ to $C_{10}$ heteroaryl.

8. The triazine compound of formula 1 according to claim 1, wherein $Ar^4$ are independently selected from unsubstituted $C_6$ to $C_{12}$ aryl or unsubstituted $C_4$ to $C_{10}$ heteroaryl.

9. The triazine compound of formula 1 according to claim 1, wherein $Ar^4$ are independently selected from phenyl, biphenyl, naphthyl, pyridyl, quinolinyl, quinazolinyl.

10. The triazine compound of formula 1 according to claim 1, wherein n=0 or 1.

11. The triazine compound of formula 1 according to claim 1, wherein a, b, c, d and e are selected from the group of:

a=1, and at least two of b, c, d and e is 1; or
b=1, and at least two of a, c, d and e is 1; or
c=1, and at least two of a, b, d and e is 1; or
d=1, and at least two of a, b, c and e is 1; or
e=1, and at least two of a, b, c and d is 1; or
a=1, and at least three of b, c, d and e is 1; or
b=1, and at least three of a, c, d and e is 1; or
c=1, and at least three of a, b, d and e is 1; or
d=1, and at least three of a, b, c and e is 1; or
e=1, and at least three of a, b, c and d is 1; or
a, b, c, d and e are 1; with the provision that a, b, c, d or e if not otherwise stated is 0.

12. The triazine compound of formula 1 according to claim 1, wherein $G^1$ has the formula 2:

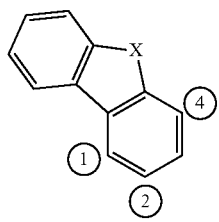
(2)
and wherein G¹ of formula 2 is linked to formula 1 at the position marked by "①".
13. The triazine compound of formula 1 according to claim 1, wherein the triazine compound is selected from D1 or D8 to D36:
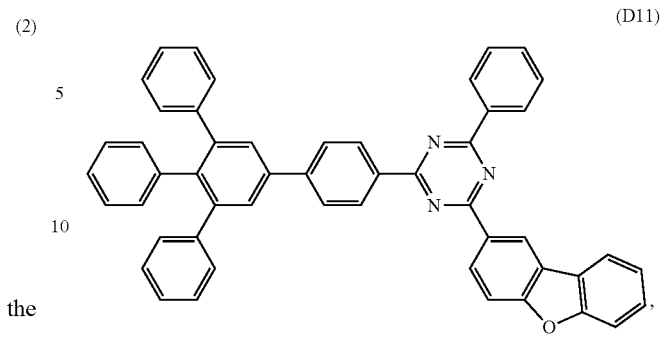
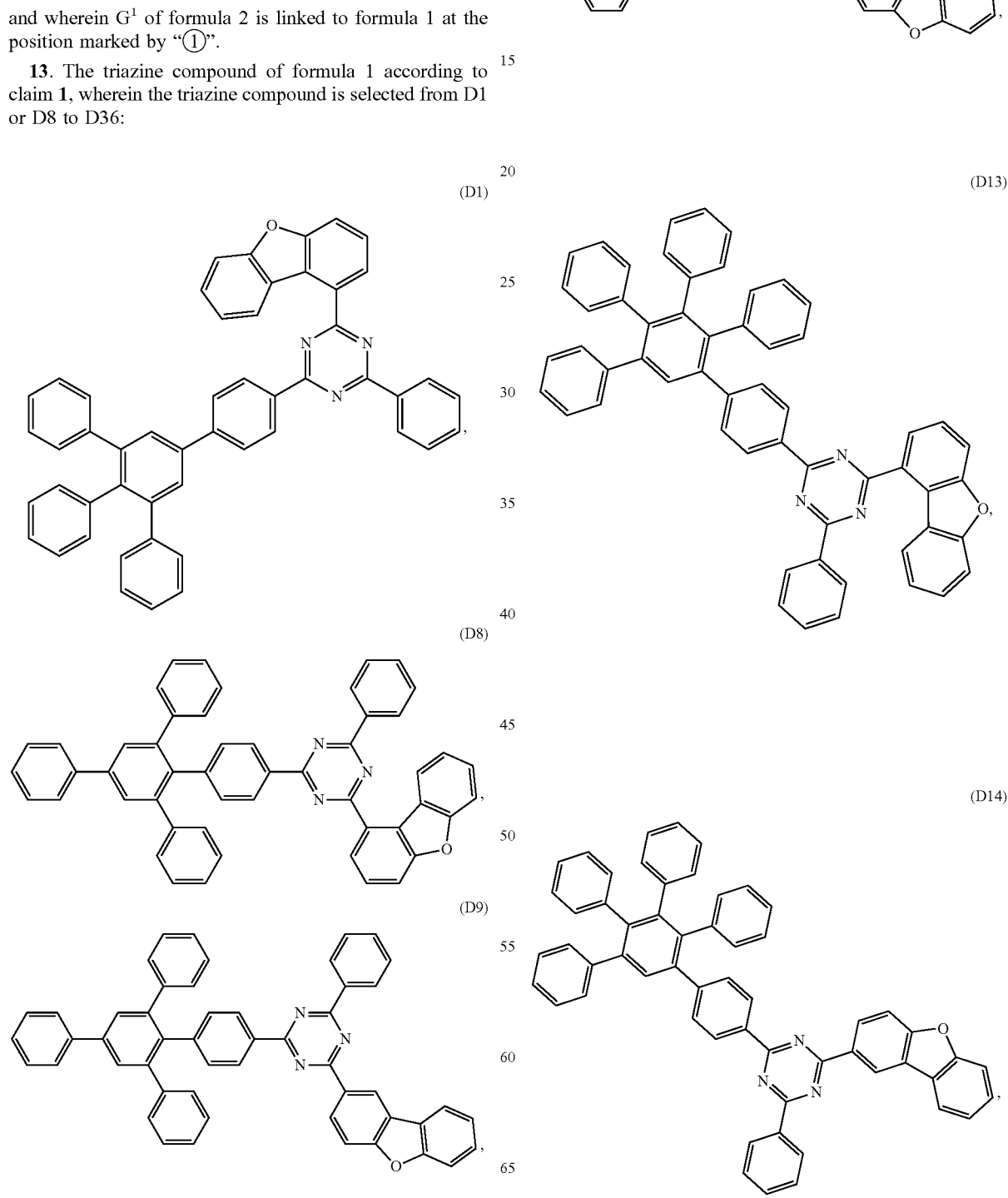

(D16)
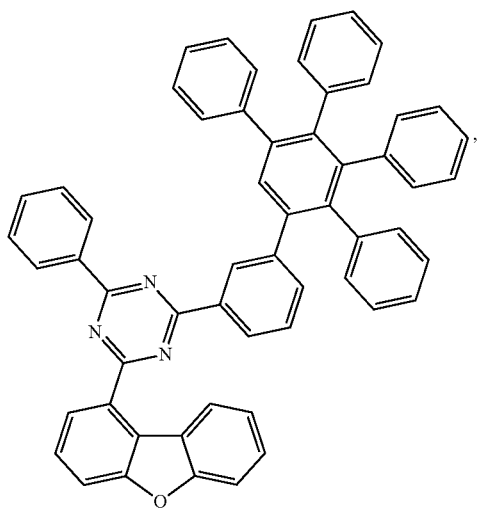
(D20)
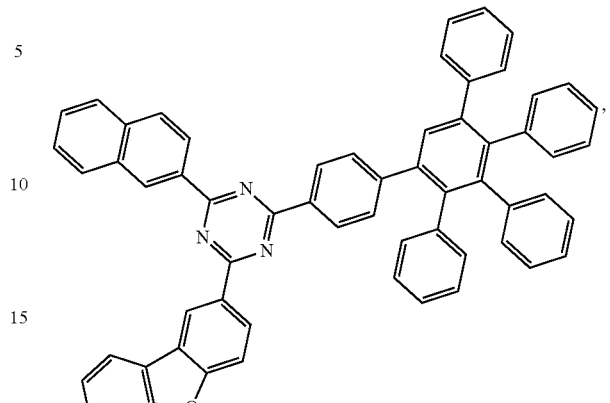
(D17)
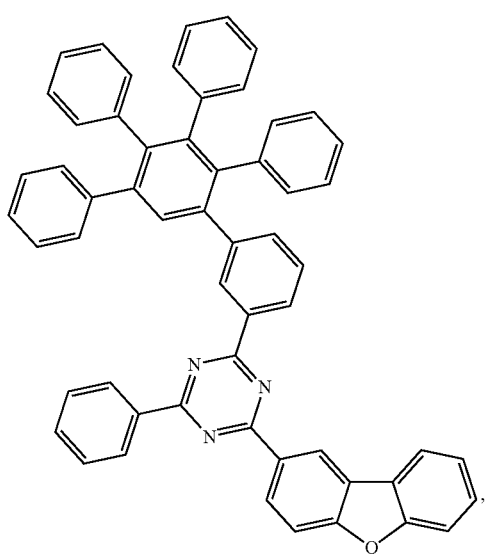
(D22)
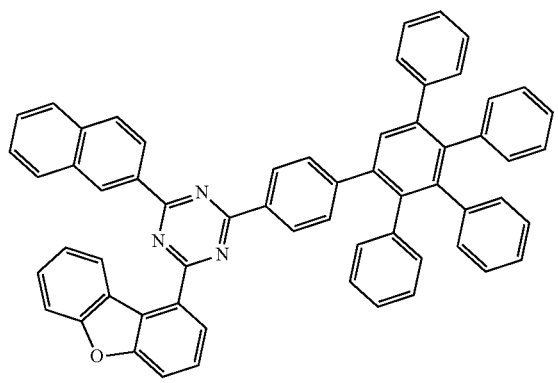
(D19)
(D23)
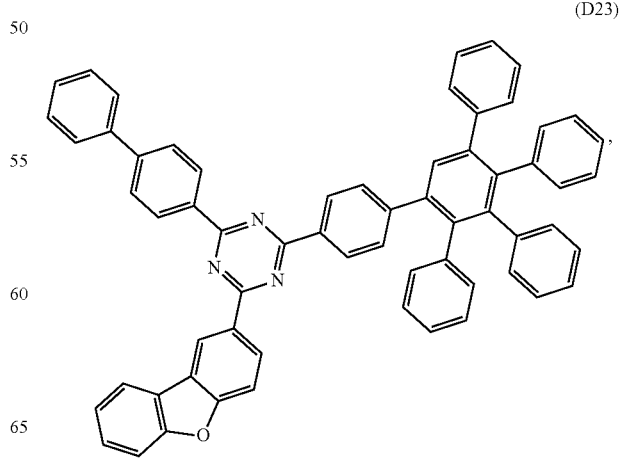

-continued
(D25)
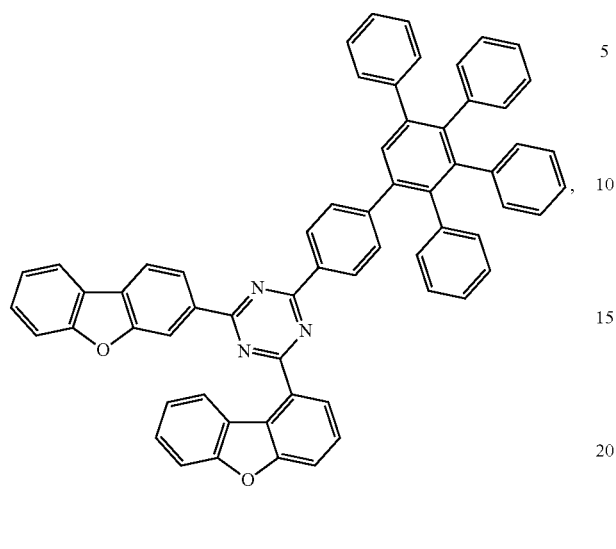
(D26)
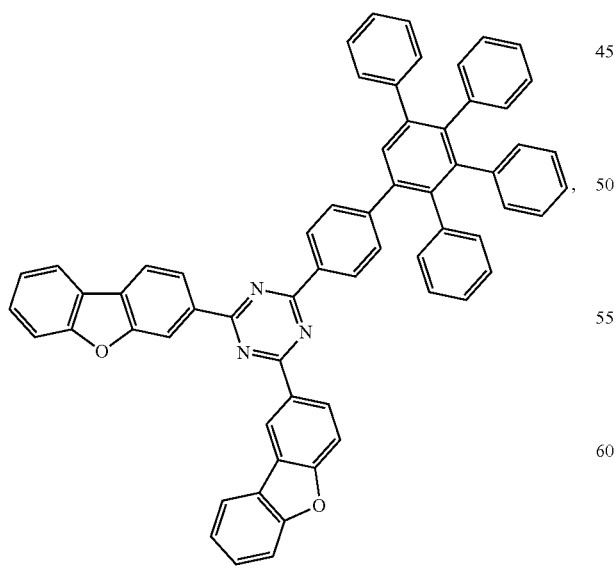
(D28)
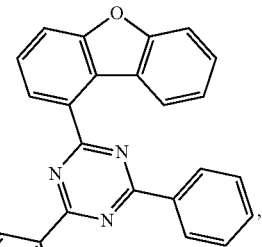
(D29)
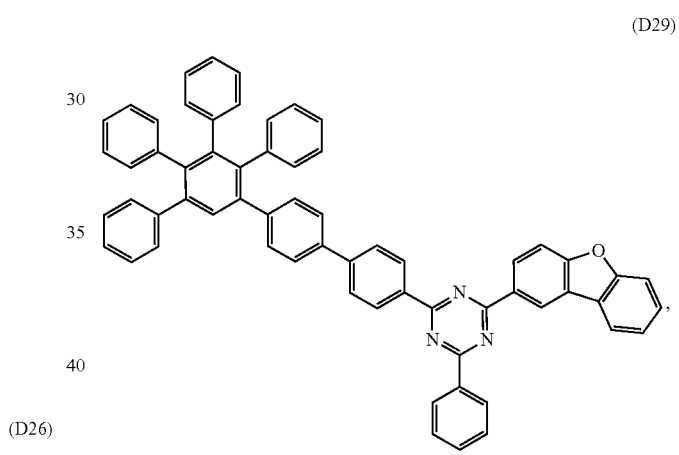
(D31)
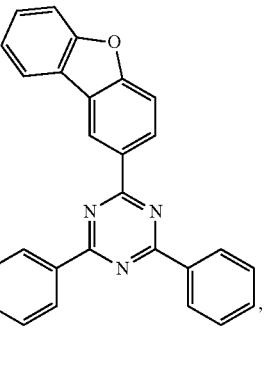

(D32)
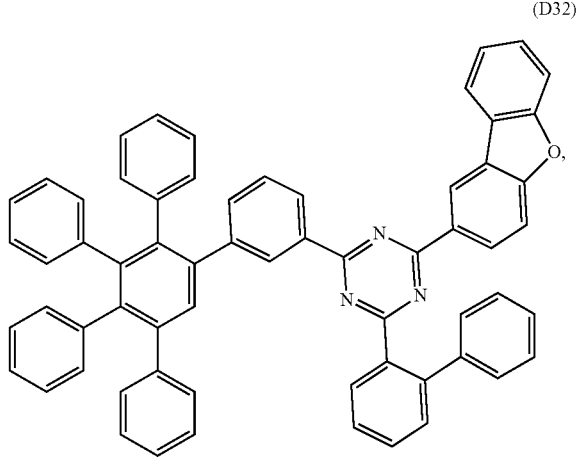

(D33)
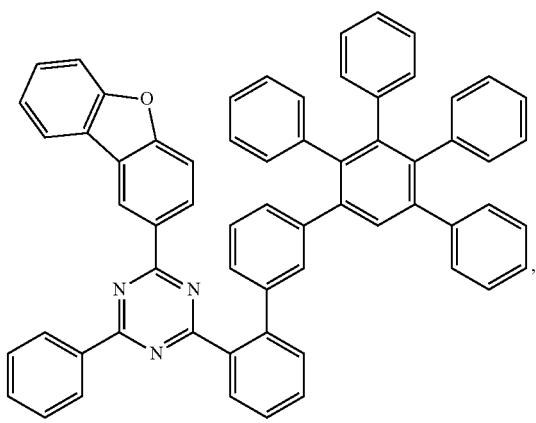

(D34)
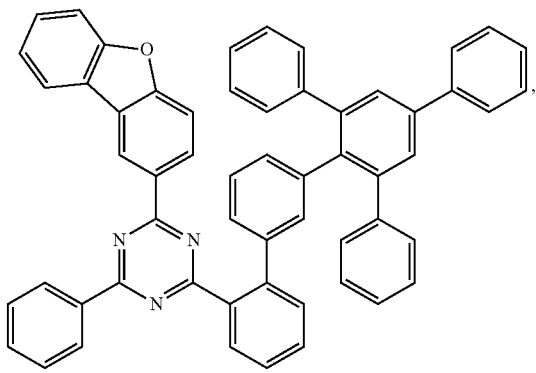

(D35)
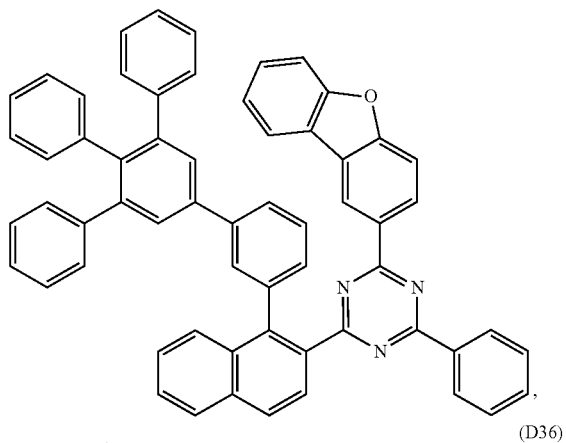

(D36)
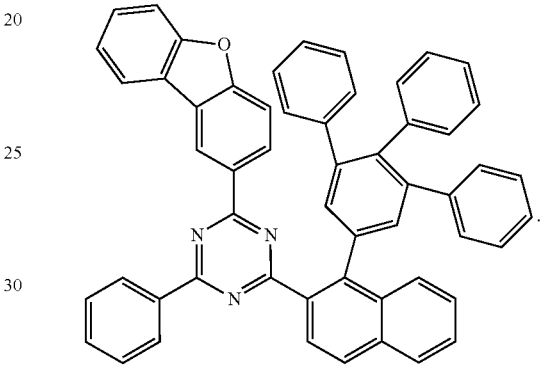

14. An organic semiconductor layer comprising at least one triazine compound of formula 1 according to claim 1.

15. The organic semiconductor layer according to claim 14, further comprises a metal, metal salt or organic metal complex.

16. An organic electronic device comprising an organic semiconductor layer according to claim 14, wherein at least one organic semiconductor layer comprises a triazine compound of formula 1 according to claim 1.

17. The organic electronic device according to claim 16, wherein the electronic device is a light emitting device, thin film transistor, a battery, a display device or a photovoltaic cell.

18. The triazine compound of formula 1 according to claim 1, wherein $Ar^3$ and/or $Ar^4$ are independently selected from unsubstituted $C_6$ to $C_{12}$ aryl, unsubstituted $C_4$ to $C_{10}$ heteroaryl and phenyl.

19. A triazine compound according to formula I:

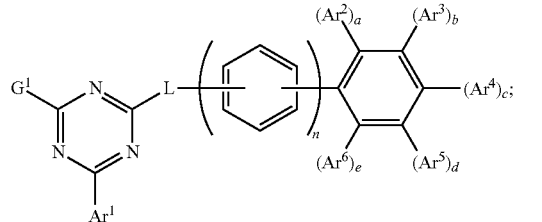

(I)

wherein formula I for L=phenylene and formula I is represented by formula 1:

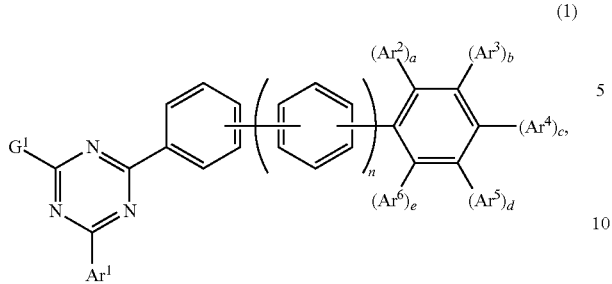

(1)

and
wherein formula I for L=naphthylene and formula I is represented by formula 1a:

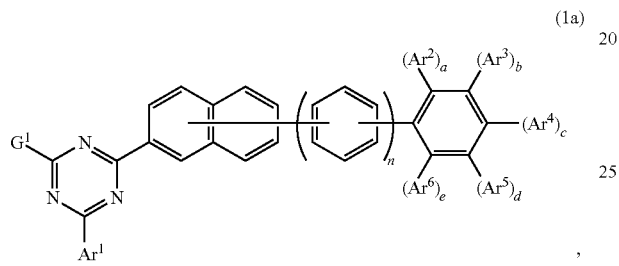

(1a)

wherein
$G^1$ has the formula 2:

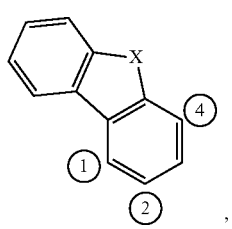

(2)

wherein $G^1$ of formula 2 is linked to formula 1 to one position, selected from the positions marked by "①" and "②";

X is O, S or Se;

a, b, c, d, e are selected from 0 or 1, wherein $2 \leq a+b+c+d+e \leq 5$;

n is selected from 0, 1 or 2, $Ar^1$ is selected from H, $C_1$ to $C_{16}$ alkyl, substituted or unsubstituted $C_6$ to $C_{40}$ aryl, substituted or unsubstituted $C_3$ to $C_{40}$ heteroaryl, wherein the substituents of the substituted $C_6$ to $C_{40}$ aryl and substituted $C_3$ to $C_{40}$ heteroaryl are selected from $C_1$ to $C_{16}$ alkyl, $C_1$ to $C_{16}$ alkoxy, $C_3$ to $C_{16}$ branched alkyl, $C_3$ to $C_{16}$ cyclic alkyl, $C_3$ to $C_{16}$ branched alkoxy, $C_3$ to $C_{16}$ cyclic alkoxy, partially or perfluorinated $C_1$ to $C_{16}$ alkyl, partially or perfluorinated $C_1$ to $C_{16}$ alkoxy, partially or perdeuterated $C_1$ to $C_{16}$ alkyl, partially or perdeuterated $C_1$ to $C_{16}$ alkoxy, $C_6$ to $C_{24}$ aryl, $C_3$ to $C_{25}$ heteroaryl, $-PX(R^1)_2$, D, F or CN, wherein $R^1$ is independently selected from $C_1$ to $C_{16}$ alkyl, $C_1$ to $C_{16}$ alkoxy, partially or perfluorinated $C_1$ to $C_{16}$ alkyl, partially or perfluorinated $C_1$ to $C_{16}$ alkoxy, partially or perdeuterated $C_1$ to $C_{16}$ alkyl, partially or perdeuterated $C_1$ to $C_{16}$ alkoxy, $C_6$ to $C_{18}$ aryl, $C_3$ to $C_{25}$ heteroaryl;

$Ar^2$, $Ar^3$, $Ar^4$, $Ar^5$ and $Ar^6$ are independently selected from substituted or unsubstituted $C_6$ to $C_{12}$ aryl or substituted or unsubstituted $C_4$ to $C_{10}$ heteroaryl, wherein the substituent of the substituted $C_6$ to $C_{12}$ aryl or substituted $C_4$ to $C_{10}$ heteroaryl is selected from $C_1$ to $C_6$ alkyl, $C_1$ to $C_6$ alkoxy, partially or perdeuterated $C_1$ to $C_6$ alkyl, partially or perdeuterated $C_1$ to $C_6$ alkoxy, partially or perfluorinated $C_1$ to $C_6$ alkyl, partially or perfluorinated $C_1$ to $C_6$ alkoxy, D, F, or CN, and wherein $Ar^3$ and $Ar^5$ are not biphenyl.

* * * * *